(12) United States Patent
Sonntag et al.

(10) Patent No.: US 10,464,991 B2
(45) Date of Patent: Nov. 5, 2019

(54) IMMUNOTHERAPY AGAINST MELANOMA AND OTHER CANCERS

(71) Applicant: IMMATICS BIOTECHNOLOGIES GMBH, Tübingen (DE)

(72) Inventors: Annika Sonntag, Tuebingen (DE); Toni Weinschenk, Aichwald (DE); Andrea Mahr, Tuebingen (DE); Oliver Schoor, Tuebingen (DE); Jens Fritsche, Dusslingen (DE); Harpreet Singh, Houston, TX (US)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 111 days.

(21) Appl. No.: 15/848,523

(22) Filed: Dec. 20, 2017

(65) Prior Publication Data

US 2018/0193439 A1 Jul. 12, 2018

Related U.S. Application Data

(63) Continuation of application No. 15/638,786, filed on Jun. 30, 2017, now Pat. No. 9,901,629, which is a continuation of application No. 15/489,399, filed on Apr. 17, 2017, now Pat. No. 10,035,838.

(60) Provisional application No. 62/325,773, filed on Apr. 21, 2016.

(30) Foreign Application Priority Data

Apr. 21, 2016 (GB) .................................. 1606919.7

(51) Int. Cl.
| | |
|---|---|
| C07K 14/74 | (2006.01) |
| G16B 25/00 | (2019.01) |
| A61K 35/17 | (2015.01) |
| A61K 39/00 | (2006.01) |
| C07K 14/725 | (2006.01) |
| C07K 16/28 | (2006.01) |
| C12N 5/0783 | (2010.01) |
| C12N 15/115 | (2010.01) |
| C12Q 1/6886 | (2018.01) |
| G01N 33/574 | (2006.01) |
| A61K 38/04 | (2006.01) |
| A61P 37/04 | (2006.01) |
| A61P 35/00 | (2006.01) |
| A61K 38/17 | (2006.01) |
| C07K 7/06 | (2006.01) |

(52) U.S. Cl.
CPC ........ *C07K 14/70539* (2013.01); *A61K 35/17* (2013.01); *A61K 38/04* (2013.01); *A61K 38/1709* (2013.01); *A61K 39/0011* (2013.01); *A61P 35/00* (2018.01); *A61P 37/04* (2018.01); *C07K 7/06* (2013.01); *C07K 14/7051* (2013.01); *C07K 16/2833* (2013.01); *C12N 5/0636* (2013.01); *C12N 5/0638* (2013.01); *C12N 15/115* (2013.01); *C12Q 1/6886* (2013.01); *G01N 33/574* (2013.01); *G01N 33/57484* (2013.01); *G16B 25/00* (2019.02); *A61K 2039/5158* (2013.01); *A61K 2039/55511* (2013.01); *A61K 2039/55516* (2013.01); *A61K 2039/55522* (2013.01); *A61K 2039/55561* (2013.01); *A61K 2039/55588* (2013.01); *C12N 2310/16* (2013.01); *C12N 2502/11* (2013.01); *C12Q 2600/156* (2013.01); *C12Q 2600/158* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 2007/0271630 A1 | 11/2007 | Boukharov et al. | |
| 2008/0107668 A1 | 5/2008 | Philip et al. | |
| 2011/0229504 A1 | 9/2011 | Fristche | |
| 2019/0004037 A1* | 1/2019 | Zhang | G01N 33/54306 |

FOREIGN PATENT DOCUMENTS

| | | |
|---|---|---|
| CA | 2 343 602 A1 | 4/2001 |
| EP | 1760088 A1 | 3/2007 |
| WO | 01 53312 A1 | 7/2001 |

(Continued)

OTHER PUBLICATIONS

NCBI reference protein sequence for S100 calcium binding protein; Available from https://www.ncbi.nlm.nih.gov/protein/56205587?report=fasta [accessed Jan. 20, 2017].

(Continued)

*Primary Examiner* — Alana Harris Dent
(74) *Attorney, Agent, or Firm* — McBee Moore Woodward & Vanik IP, LLC

(57) ABSTRACT

A method of treating a patient who has melanoma includes administering to said patient a composition containing a population of activated T cells that selectively recognize cells in the patient that aberrantly express a peptide. A pharmaceutical composition contains activated T cells that selectively recognize cells in a patient that aberrantly express a peptide, and a pharmaceutically acceptable carrier, in which the T cells bind to the peptide in a complex with an MHC class I molecule, and the composition is for treating the patient who has melanoma. A method of treating a patient who has melanoma includes administering to said patient a composition comprising a peptide in the form of a pharmaceutically acceptable salt, thereby inducing a T-cell response to the melanoma.

20 Claims, 16 Drawing Sheets
Specification includes a Sequence Listing.

(56) References Cited

FOREIGN PATENT DOCUMENTS

WO 2004016225 A2 2/2004
WO 2013/151665 A2 10/2013
WO 2015/193359 A2 12/2015

OTHER PUBLICATIONS

Bandarchi et al. "From Melanocyte to Metastatic Malignant Melanoma", Dermatology Research and Practice, vol. (2010) article ID 583748.
Combined GB Search and Examination Report dated Jan. 23, 2017.
Sutmuller et al. J Immunology 165: 7308-7315, 2000.
Weinschenk, T. et al. "Integrated functional genomics approach for the design of patient-individual antitumor vaccines." Cancer Research, American Association for Cancer Research. vol. 62, No. 20. Oct. 15, 2002. pp. 5818-5827. XP002266492. ISSN: 0008-5472.
S Keijser et al. "Immunophenotypic markers to differentiate between benign and malignant melanocytic lesions." British Journal of Ophthalmology. vol. 90, No. 2. Jan. 19, 2006. pp. 213-217. DOI: 10.1136/bjo.2005.080390.
Vitaly Sviathoa et al. "Immunohistochemical analysis of the S100A1, S100B, CD44 and Bcl-2 antigens and the rate of cell proliferation asserted by Ki-67 antibody in benign and malignant melanocytic tumours." Melanoma Research. vol. 20, No. 2. Apr. 1, 2010. DOI: 10.1097/CMR.0b013e3283350554.
International Search Report for PCT/EP2017/059016, dated Aug. 23, 2017.

\* cited by examiner

Peptide: FLDVKELML (A*02)
SEQ ID NO: 1

Peptide: VLFKDPVSV (A*02)

SEQ ID NO: 3

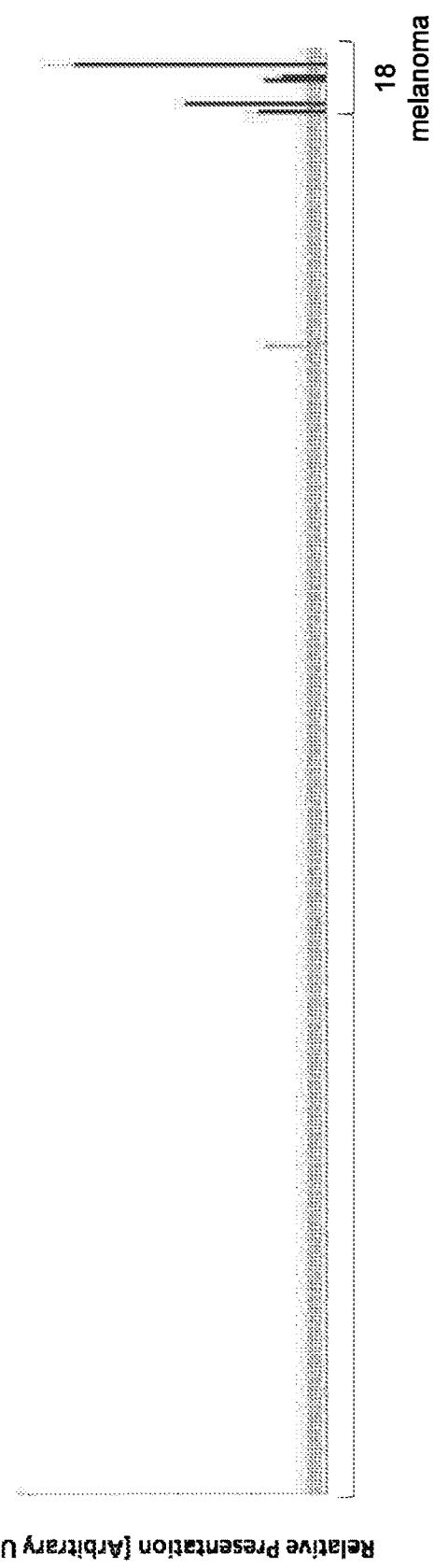

Peptide: NLQEKVPEL (A*02)

SEQ ID NO: 7

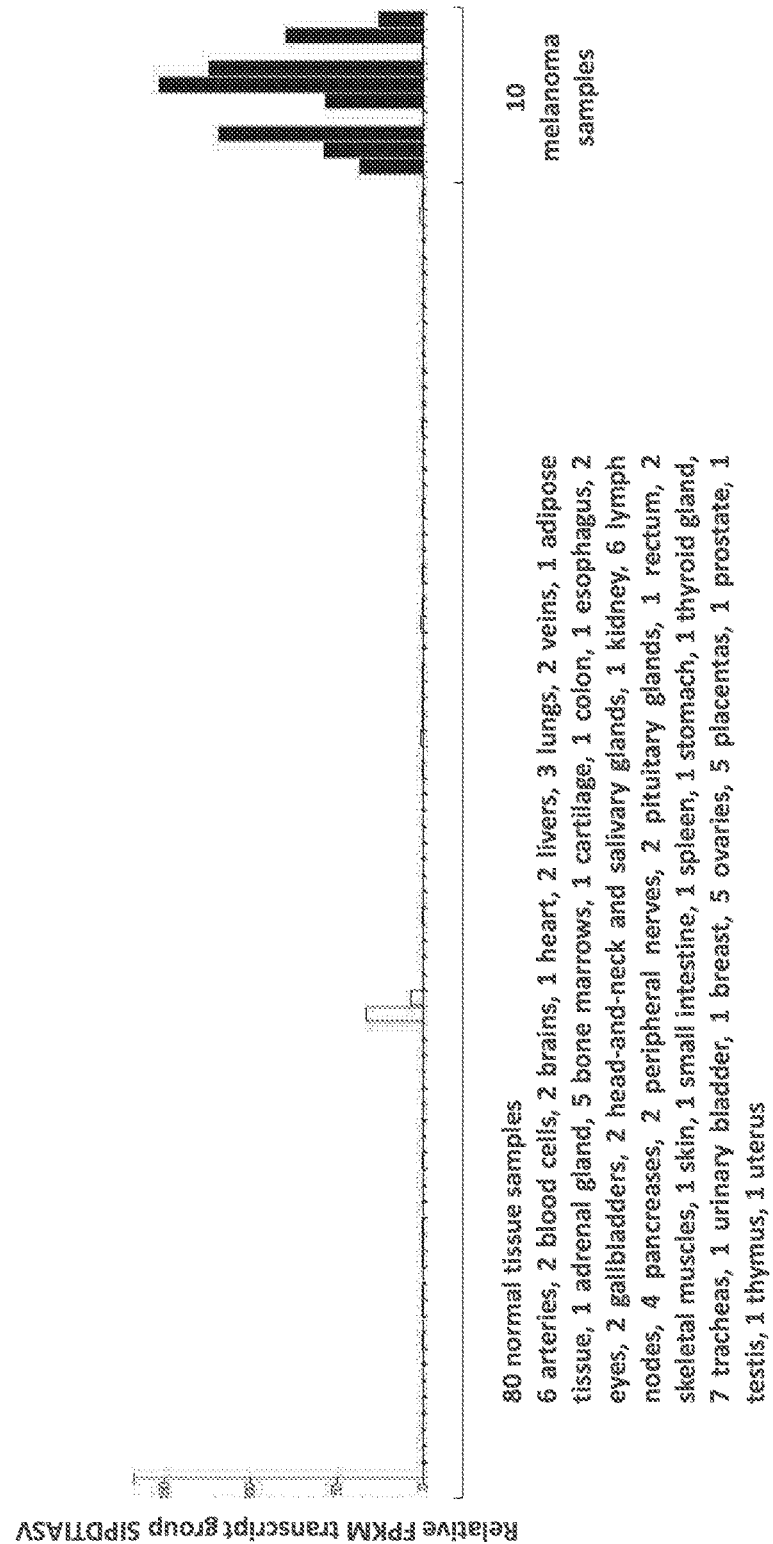

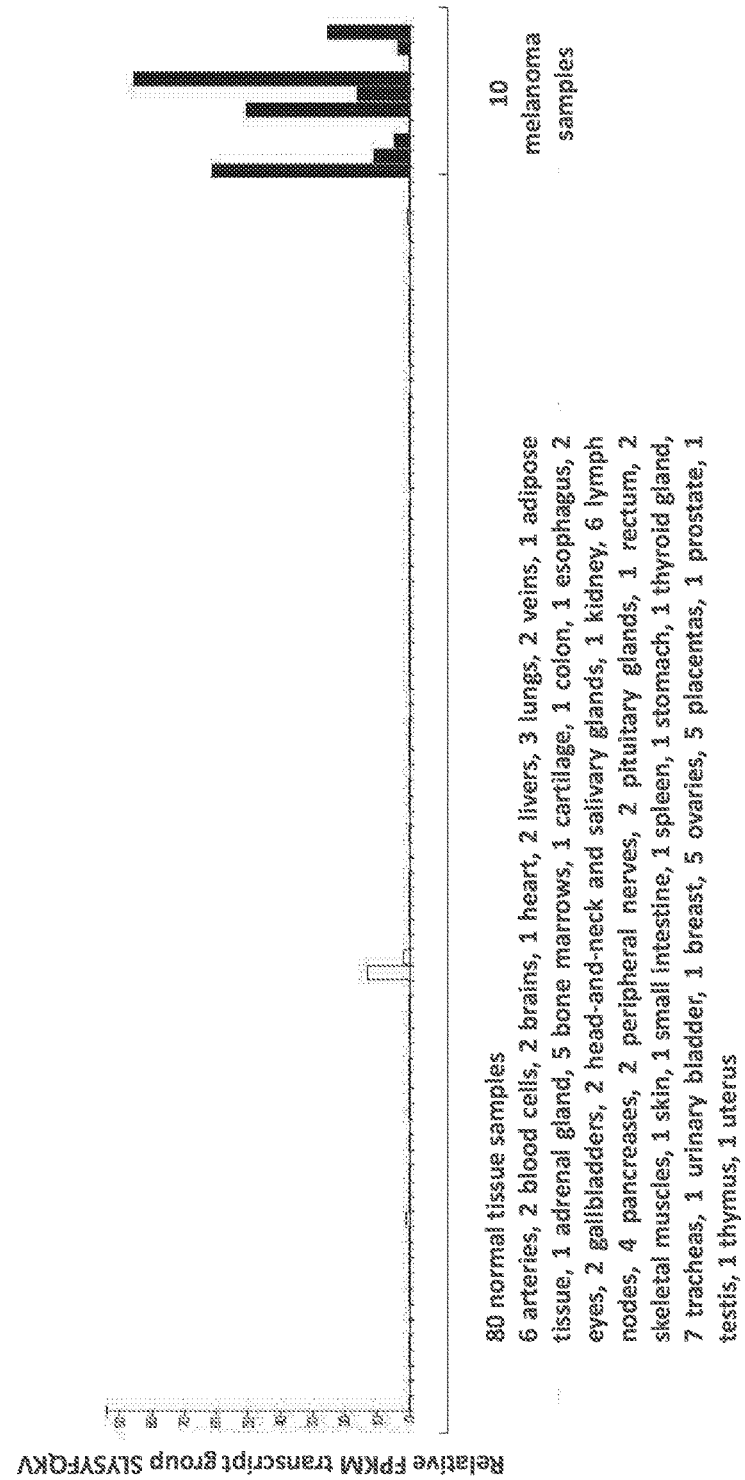

Gene: FMN1
Peptide: ALPPPPASI
SEQ ID NO: 39

IMMUNOTHERAPY AGAINST MELANOMA AND OTHER CANCERS

CROSS REFERENCE TO RELATED APPLICATIONS

This application is continuation of U.S. application Ser. No. 15/638,786, filed 30 Jun. 2017, which is continuation of U.S. application Ser. No. 15/489,399, filed 17 Apr. 2017, which claims the benefit of U.S. Provisional Application Ser. No. 62/325,773, filed 21 Apr. 2016, and Great Britain Application No. 1606919.7, filed 21 Apr. 2016, the content of each of these applications is herein incorporated by reference in their entirety.

This application also is related to PCT/EP2017/059016 filed 13 Apr. 2017, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-068003_ST25.txt" created on 20 Dec. 2017, and 52,262 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

Melanoma

Globally, melanoma is diagnosed with an incidence rate of 3.0 in 100,000, representing 1.7% of all cancer cases. In 2012, 232,000 women were diagnosed with melanoma. The mortality rate of 0.7 in 100,000 women is substantially lower than the incidence rate (Ferlay et al., 2013). The lifetime risk of getting melanoma is about 2.4% (1 in 40) for whites, 0.1% (1 in 1,000) for blacks, and 0.5% (1 in 200) for Hispanics. Although the average age at melanoma diagnosis is 62, it is one of the most common cancers in young adults (especially young women) (American Cancer Society, 2015).

For patients with localized melanoma, prognosis is good with adequate surgical excision which is reflected by the relatively low melanoma mortality rates (World Cancer Report, 2014). In line, the 5-year survival rate is more than 90% and 80% for stage I and II lesions, respectively (Kaufman et al., 2013).

Metastatic melanoma is however largely resistant to current therapies (World Cancer Report, 2014). The 5-year survival rate is 78-40% for stage IIIA-C and 15-20% for stage IV (American Cancer Society, 2015).

Besides sun-exposure, the risk to develop melanoma is influenced by other environmental factors such as age and sex as well as anatomical location and individual susceptibility. Ultraviolet-emitting tanning devices also increase the risk of malignant melanoma. In 20-40% of families with a melanoma history, CDKN2A mutations have been found (World Cancer Report, 2014).

Melanomas occur primarily in the skin—more than 95% of cases—but are also found in the mucous membranes of the mouth, nose, anus, and vagina and, to a lesser extent, the intestine. Furthermore, melanocytes are present in the conjunctiva, the retina, and the meninges. Melanoma can be subtyped histologically into superficial spreading melanoma, nodular melanoma, acral lentiginous melanoma, and lentigo maligna melanoma. Melanomas are classified according to the TNM classification. As recommended in the American Joint Committee on Cancer staging manual, melanoma patients are categorized into three groups: localized disease with no evidence of metastases (stage I-II), regional disease (stage III), and distant metastatic disease (stage IV) (World Cancer Report, 2014).

The standard therapy in melanoma is complete surgical resection with surrounding healthy tissue. If resection is not complete or not possible at all, patients receive primary radiation therapy, which can be combined with interferon-alpha administration in advanced stages (stages IIB/C and IIIA-C). In Germany no standard therapeutic regimen exists for the treatment of patients with late stage and metastasizing melanoma. Therefore, patients suffering from late stage and metastasizing melanoma should be treated in the context of a clinical study. Therapeutic options include mono-chemotherapy, poly-chemotherapy and targeted therapies with specific inhibitors. Dacarbazine, temozolamide and fotemustin are currently used in mono-chemotherapy trial. Different combinations of chemotherapeutics are investigated in poly-chemotherapy studies: the CarboTax regimen (carboplatin plus paclitaxel), the GemTreo regimen (gemcitabine plus treosulfan), the DVP regimen (dacarbazine plus vindesin plus cisplatin), the BHD regimen (carmustine plus hyroxyurea plus dacarbazine) and the BOLD regimen (bleomycin plus vincristine plus lomustine plus darcarbazine). Furthermore, chemotherapy in combination with ipilimumab and the administration of specific BRAF, c-KIT and N-RAS inhibitors to patients with mutations within the respective genes are currently evaluated in clinical trials (S3-Leitlinie Melanom, 2013).

Enhancing the anti-tumor immune responses appears to be a promising strategy for the treatment of advanced melanoma. In the United States the immune checkpoint inhibitor ipilimumab as well as the BRAF kinase inhibitors vemurafenib and dabrafenib and the MEK inhibitor trametinib are already approved for the treatment of advanced melanoma. Both approaches increase the patient's anti-tumor immunity—ipilimumab directly by reducing T cell inhibition and the kinase inhibitors indirectly by enhancing the expression of melanocyte differentiation antigens (Srivastava and McDermott, 2014). Vemurafenib has a response rate of 40-50% but with a median duration of only 5-6 months (World Cancer Report, 2014). Furthermore, the combination of vemurafenib with of cobimetinib, another MAPK pathway inhibitor targeting the kinase MEK received FDA approval (National Cancer Institute, 2015).

Several different vaccination approaches have already been evaluated in patients with advanced melanoma. So far, phase III trials revealed rather disappointing results and vaccination strategies clearly need to be improved.

Adoptive T cell transfer shows great promise for the treatment of advanced stage melanoma. In vitro expanded autologous tumor infiltrating lymphocytes as well as T cells harboring a high affinity T cell receptor for the cancer-testis antigen NY-ESO-1 had significant beneficial and low toxic effects upon transfer into melanoma patients. Unfortunately, T cells with high affinity T cell receptors for the melanocyte specific antigens MART1 and gp100 and the cancer-testis antigen MAGEA3 induced considerable toxic effects in clinical trials. Thus, adoptive T cell transfer has high therapeutic potential, but safety and tolerability of these treatments needs to be further increased (Phan and Rosenberg, 2013; Hinrichs and Restifo, 2013).

Only recently, the FDA approved the first oncolytic virus therapy, talimogene laherparepvec (T-VEC). The agency approved T-VEC for the treatment of some patients with metastatic melanoma that cannot be surgically removed (National Cancer Institute, 2015).

Considering the severe side-effects and expense associated with treating cancer, there is a need to identify factors that can be used in the treatment of cancer in general and melanoma in particular. There is also a need to identify factors representing biomarkers for cancer in general and melanoma in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens.

The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in the literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell- (CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated (longer) peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 237 or a variant sequence thereof which is at least 77%, preferably at least 88%, homologous (preferably at least 77% or at least 88% identical) to SEQ ID NO: 1 to SEQ ID NO: 237, wherein said variant binds to MHC and/or induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group consisting of SEQ ID NO: 1 to SEQ ID NO: 237 or a variant thereof, which is at least 77%, preferably at least 88%, homologous (preferably at least 77% or at least 88% identical) to SEQ ID NO: 1 to SEQ ID NO: 237, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 were identified from large listings as results of high-throughput screenings with high error rates or calculated using algorithms, but have not been associated with cancer at all before. The peptides in Table 3 are additional peptides that may be useful individually or in combination with the other peptides of the invention. The peptides in Table 4 are furthermore useful in the diagnosis and/or treatment of various other malignancies that involve an over-expression or over-presentation of the respective underlying polypeptide.

TABLE 1

Peptides according to the present invention.

| SEQ ID No | Sequence | Gene ID(s) | Official Gene Symbol(s) |
|---|---|---|---|
| 1 | FLDVKELML | 6271 | S100A1 |
| 2 | VLLGENVEL | 83872 | HMCN1 |
| 3 | VLFKDPVSV | 2134 | EXTL1 |
| 4 | KTWDQVPFSV | 6490 | PMEL |
| 5 | ILDEGHILQL | 83872 | HMCN1 |
| 6 | SIPDTIASV | 283652 | SLC24A5 |
| 7 | NLQEKVPEL | 200728 | TMEM17 |
| 8 | SIIPYLLEA | 89797 | NAV2 |
| 9 | SLAGLVLYV | 399694 | SHC4 |
| 10 | KMTQYITEL | 9915 | ARNT2 |
| 11 | TLIELLLPKL | 6773 | STAT2 |
| 12 | RLDDKTTNV | 5027 | P2RX7 |
| 13 | IQSETTVTV | 83872 | HMCN1 |
| 14 | VLYEMLYGL | 100533105, 23678, 6446 | C8orf44-SGK3, SGK3, SGK1 |
| 15 | VLYDPVVGC | 11180 | WDR6 |
| 16 | GLFPSNFVTA | 8027 | STAM |
| 17 | GVVHGVATV | 6622 | SNCA |
| 18 | SLADVVDTL | 55553, 6660 | SOX6, SOX5 |
| 19 | VLAVLGAVVAV | 3106, 3107 | HLA-B, HLA-C |
| 20 | VISPHGIASV | 5270 | SERPINE2 |
| 21 | FMYNFQLVTL | 2181 | ACSL3 |
| 22 | KLLELQELVL | 2801, 342096, 55149, 55889, 653641, 653643 | GOLGA6D, GOLGA2, MTPAP, GOLGA6A, GOLGA6C, GOLGA6B |
| 23 | FLGDPPPGL | 127703 | C1orf216 |
| 24 | SLVAILHLL | 55742 | PARVA |
| 25 | FIDPEQIQV | 101060422, 8515 | LOC101060422, ITGA10 |
| 26 | KIEDLIKYL | 11258 | DCTN3 |

TABLE 1-continued

Peptides according to the present invention.

| SEQ ID No | Sequence | Gene ID(s) | Official Gene Symbol(s) |
|---|---|---|---|
| 27 | TLWYVPLSL | 11332 | ACOT7 |
| 28 | IVDNTTMQL | 3421 | IDH3G |
| 29 | ILDDVAMVL | 58517 | RBM25 |
| 30 | VLFPMDLAL | 5784 | PTPN14 |
| 31 | FLPRKFPSL | 23246, 727967 | BOP1 |
| 32 | GLDIITNKV | 54802 | TRIT1 |
| 33 | SLYSYFQKV | 51151 | SLC45A2 |
| 34 | YLINFEIRSL | 57539 | WDR35 |
| 35 | ALFAAGANV | 116211, 255758 | TM4SF19 |
| 36 | SVNGFISTL | 3709, 3710 | ITPR2, ITPR3 |
| 37 | TLKEYLESL | 285190, 400966, 5903, 653489, 727851, 729540, 729857, 84220 | RANBP2, RGPD1, RGPD2, RGPD3, RGPD4, RGPD5, RGPD6, RGPD8 |
| 38 | KLGFGTGVNVYL | 55872 | PBK |
| 39 | ALPPPPASI | 342184 | FMN1 |
| 40 | LLSNTVSTL | 283652 | SLC24A5 |
| 41 | LLDDPTNAHFI | 2118 | ETV4 |
| 42 | VLKADVVLL | 259307 | IL4I1 |
| 43 | LLPDPLYSL | 9631 | NUP155 |
| 44 | FLYTYIAKV | 54763 | ROPN1 |
| 45 | FVYGEPREL | 392555, 51438 | MAGEC2 |
| 46 | VMSSTLYTV | 51151 | SLC45A2 |
| 47 | ALDSDPVGL | 25894 | PLEKHG4 |
| 48 | HLIGWTAFL | 51151 | SLC45A2 |
| 49 | ALLSQDFEL | 4241 | MFI2 |
| 50 | HLDQIFQNL | 6355 | CCL8 |
| 51 | LIDKIIEYL | 25914 | RTTN |
| 52 | NLDYAILKL | 374393 | FAM111B |
| 53 | ILDEEKFNV | 55127 | HEATR1 |
| 54 | LLDSGAFHL | 27304 | MOCS3 |
| 55 | NLDKLYHGL | 8318 | CDC45 |
| 56 | ILDELVKSL | 56852 | RAD18 |
| 57 | GILSFLPVL | 2213, 9103 | FCGR2B, FCGR2C |
| 58 | ILGDWSIQV | 135228 | CD109 |
| 59 | IIDDVMKEL | 79959 | CEP76 |
| 60 | ILPEAQDYFL | 80071 | CCDC15 |
| 61 | KLSVHVTAL | 89858 | SIGLEC12 |
| 62 | LLDTTQKYL | 54811 | ZNF562 |

TABLE 1-continued

Peptides according to the present invention.

| SEQ ID No | Sequence | Gene ID(s) | Official Gene Symbol(s) |
|---|---|---|---|
| 63 | SIDDSDPIV | 26046 | LTN1 |
| 64 | SLGPIMLTKI | 2086 | ERV3-1 |
| 65 | TTLGGFAKV | 196528 | ARID2 |
| 66 | VMFEYGMRL | 23279 | NUP160 |
| 67 | YVDSEGIVRM | 11169 | WDHD1 |
| 68 | FLAEAARSL | 79654 | HECTD3 |
| 69 | IIDDKPIGL | 9420 | CYP7B1 |
| 70 | LIDEAAQML | 85441 | HELZ2 |
| 71 | SLDEVAVSL | 144455 | E2F7 |
| 72 | TLLEVDAIVNA | 140733 | MACROD2 |
| 73 | ELDKIYETL | 51163 | DBR1 |
| 74 | GTIPLIESL | 160418 | TMTC3 |
| 75 | FMYAGQLTL | 79842 | ZBTB3 |
| 76 | QIDSIHLLL | 55102 | ATG2B |
| 77 | SIDDVVKKL | 6672 | SP100 |
| 78 | ALKDLVNLI | 23001 | WDFY3 |
| 79 | AVDNILLKL | 1763 | DNA2 |
| 80 | FADELSHLL | 79830 | ZMYM1 |
| 81 | FLDDGNQML | 79659 | DYNC2H1 |
| 82 | GIDDLHISL | 23224 | SYNE2 |
| 83 | GLDKVITVL | 9833 | MELK |
| 84 | GLDTILQNL | 79830 | ZMYM1 |
| 85 | GLLDVMYQV | 254251 | LCORL |
| 86 | HTLPHEIVVNL | 23195 | MDN1 |
| 87 | IIDPPLHGQLL | 80144 | FRAS1 |
| 88 | ILDGIIREL | 254065 | BRWD3 |
| 89 | ILDNSPAFL | 163786 | SASS6 |
| 90 | ILDYIHNGL | 84640 | USP38 |
| 91 | ILLDRLFSV | 54796, 646 | BNC1, BNC2 |
| 92 | KLPGFPTQDDEV | 51202 | DDX47 |
| 93 | LLAKAVQNV | 100271927, 10156 | RASA4, RASA4B |
| 94 | LLDAFSIKL | 23224 | SYNE2 |
| 95 | LLDALQHEL | 93323 | HAUS8 |
| 96 | LLDMSLVKL | 55038 | CDCA4 |
| 97 | NLDATVTAL | 22995 | CEP152 |
| 98 | NLPNTNSILGV | 57862 | ZNF410 |
| 99 | NLPSELPQL | 100137047, 100137049, 8681 | JMJD7 |

TABLE 1-continued

Peptides according to the present invention.

| SEQ ID No | Sequence | Gene ID(s) | Official Gene Symbol(s) |
|---|---|---|---|
| 100 | NLREILQNV | 253260 | RICTOR |
| 101 | NVDENVAEL | 51678 | MPP6 |
| 102 | RLPDQFSKL | 51735, 96459 | RAPGEF6 |
| 103 | SLDAVMPHL | 6477 | SIAH1 |
| 104 | SLDQIIQHL | 51750, 8771 | RTEL1 |
| 105 | SLKQTVVTL | 8924 | HERC2 |
| 106 | TLSEICEFI | 2297, 2306 | FOXD1, FOXD2 |
| 107 | TLVAFLQQV | 79659 | DYNC2H1 |
| 108 | TVIRPLPGL | 389524, 84163 | GTF2IRD2, GTF2IRD2B |
| 109 | VIDDLIQKL | 79659 | DYNC2H1 |
| 110 | VLDTLTKVL | 26292 | MYCBP |
| 111 | VLDVSFNRL | 2811 | GP1BA |
| 112 | VLPAVLTRL | 2175 | FANCA |
| 113 | VLYSLVSKI | 23335 | WDR7 |
| 114 | VVDDIVSKL | 10926 | DBF4 |
| 115 | YIDDVFMGL | 84002 | B3GNT5 |
| 116 | LMDETMKEL | 348 | APOE |
| 117 | KQQASQVLV | 5627 | PROS1 |
| 118 | TMIEICEKL | 10988 | METAP2 |
| 119 | SLGLGFISRV | 4644 | MYO5A |
| 120 | QLMEGKVVL | 27340 | UTP20 |
| 121 | FLEDLVPYL | 84342 | COG8 |
| 122 | YVDDFGVSV | 2132 | EXT2 |
| 123 | LLGEGIPSA | 85461 | TANC1 |
| 124 | FLPQKIIYL | 5721 | PSME2 |
| 125 | YLFAFLNHL | 23380, 57522, 9901 | SRGAP1, SRGAP3, SRGAP2 |
| 126 | SLIDFVVTC | 10457 | GPNMB |
| 127 | TLISDIEAVKA | 81619 | TSPAN14 |
| 128 | ALFPGDVDRL | 5834 | PYGB |
| 129 | VLPDDLSGV | 2771 | GNAI2 |
| 130 | GLVDVLYTA | 9710 | KIAA0355 |
| 131 | FVDPNGKISL | 8729 | GBF1 |
| 132 | FLDASGAKL | 9689 | BZW1 |
| 133 | ALDPAYTTL | 3172 | HNF4A |
| 134 | LLDEVLHTM | 4089 | SMAD4 |
| 135 | FLDDQETRL | 10906 | TRAFD1 |
| 136 | FAYDGKDYIAL | 3105, 3106, 3107 | HLA-C, HLA-B, HLA-A |

TABLE 1-continued

Peptides according to the present invention.

| SEQ ID No | Sequence | Gene ID(s) | Official Gene Symbol(s) |
|---|---|---|---|
| 137 | ILPSNLLTV | 5297 | PI4KA |
| 138 | YLDKTFYNL | 23325 | KIAA1033 |
| 139 | AVDATVNQV | 10130 | PDIA6 |
| 140 | RLEAYLARV | 10763 | NES |
| 141 | YVIDPIKGL | 5339 | PLEC |
| 142 | FVDGSAIQV | 26010 | SPATS2L |
| 143 | ILDDSALYL | 23130 | ATG2A |
| 144 | SVDEVEISV | 10598 | AHSA1 |
| 145 | TLPNIYVTL | 55102 | ATG2B |
| 146 | GVGPVPARA | 81533 | ITFG1 |
| 147 | ILDDQTNKL | 1601 | DAB2 |
| 148 | TLKDIVQTV | 54855 | FAM46C |
| 149 | YLDTFALKL | 401548 | SNX30 |
| 150 | KLFPSPLQTL | 111 | ADCY5 |
| 151 | FLGEPASYLYL | 6638 | SNRPN |
| 152 | IMEDFTTFL | 55601 | DDX60 |
| 153 | RLDEVSREL | 6238 | RRBP1 |
| 154 | TLGTATFTV | 5321 | PLA2G4A |
| 155 | GLAGFFASV | 2030 | SLC29A1 |
| 156 | ALMDTDGSGKLNL | 825 | CAPN3 |
| 157 | HLFETISQA | 5691 | PSMB3 |
| 158 | KLIPSIIVL | 719 | C3AR1 |
| 159 | TILATVPLV | 6720 | SREBF1 |
| 160 | ALDDISESI | 25996 | REXO2 |
| 161 | GLCDSIITI | 23788 | MTCH2 |
| 162 | TLDGNPFLV | 929 | CD14 |
| 163 | RLMANPEALKI | 2633 | GBP1 |
| 164 | ALFFQLVDV | 6185 | RPN2 |
| 165 | ALIEVLQPLI | 7453 | WARS |
| 166 | SIIPPLFTV | 6748 | SSR4 |
| 167 | KVLGDVIEV | 1410 | CRYAB |
| 168 | KLLAATLLL | 10673 | TNFSF13B |
| 169 | TLLESIQHV | 8924 | HERC2 |
| 170 | KLKEAVEAI | 8450 | CUL4B |
| 171 | KVSGVILSV | 1186 | CLCN7 |
| 172 | FLPAGIVAV | 11319 | ECD |
| 173 | ALDDIIYRA | 84668 | FAM126A |
| 174 | TLLEGLTEL | 8382 | NME5 |

TABLE 1-continued

Peptides according to the present invention.

| SEQ ID No | Sequence | Gene ID(s) | Official Gene Symbol(s) |
| --- | --- | --- | --- |
| 175 | VLDSVDVRL | 113189 | CHST14 |
| 176 | TLYEQEIEV | 23127 | GLT25D2 |
| 177 | ILWDTLLRL | 29954 | POMT2 |
| 178 | FAYDGKDYIA | 3105, 3106, 3107 | HLA-A, HLA-B, HLA-C |
| 179 | ALDDTVLQV | 337876 | CHSY3 |
| 180 | KLAEALYIA | 22938 | SNW1 |
| 181 | GLIDLEANYL | 222553 | SLC35F1 |
| 182 | SVALVIHNV | 10385 | BTN2A2 |
| 183 | FLDSLIYGA | 55974 | SLC50A1 |
| 184 | VLFSSPPVILL | 5621 | PRNP |
| 185 | ILADATAKM | 7094 | TLN1 |
| 186 | FLDHEMVFL | 100996782, 54797 | LOC100996782, MED18 |
| 187 | SLPRPTPQA | 1601 | DAB2 |

TABLE 2

Additional peptides according to the present invention

| SEQ ID No | Sequence | Gene ID(s) | Official Gene Symbol(s) |
| --- | --- | --- | --- |
| 188 | VVVDPIQSV | 10213 | PSMD14 |
| 189 | KALQFLEEV | 908 | CCT6A |
| 190 | RLVSLITLL | 57231 | SNX14 |
| 191 | YLDKMNNNI | 9686 | VGLL4 |
| 192 | KLFTQIFGV | 27434 | POLM |
| 193 | ALDEPTTNL | 10111 | RAD50 |
| 194 | TLDDIMAAV | 26057 | ANKRD17 |
| 195 | IAAGIFNDL | 5695 | PSMB7 |
| 196 | ALEPIDITV | 5885 | RAD21 |
| 197 | ALDSGFNSV | 84859 | LRCH3 |
| 198 | EVVDKINQV | 23224 | SYNE2 |
| 199 | AIHTAILTL | 5683 | PSMA2 |
| 200 | LLEEINHFL | 472 | ATM |
| 201 | SLIDRTIKM | 84928 | TMEM209 |
| 202 | RVAFKINSV | 91543 | RSAD2 |
| 203 | FLNEDISKL | 22989 | MYH15 |
| 204 | RMDEEFTKI | 728689, 8663 | EIF3C, EIF3CL |
| 205 | SLKSKVLSV | 122830 | NAA30 |
| 206 | LLYEDIPDKV | 22920 | KIFAP3 |

TABLE 2-continued

Additional peptides according to the present invention

| SEQ ID No | Sequence | Gene ID(s) | Official Gene Symbol(s) |
|---|---|---|---|
| 207 | VQIGDIVTV | 6205 | RPS11 |
| 208 | YSDDIPHAL | 3646 | EIF3E |
| 209 | SILDGLIHL | 55705 | IPO9 |
| 210 | LLPELRDWGV | 56931 | DUS3L |
| 211 | FLPFLTTEV | 55974 | SLC50A1 |
| 212 | LLKDSIVQL | 5573 | PRKAR1A |
| 213 | LLDPTNVFI | 119559 | SFXN4 |
| 214 | VLMEMSYRL | 55159 | RFWD3 |
| 215 | EVISKLYAV | 10694 | CCT8 |
| 216 | TLLHFLAEL | 1729 | DIAPH1 |
| 217 | NMMSGISSV | 1457 | CSNK2A1 |
| 218 | STLHLVLRL | 6233, 728590, 7311, 7314, 7316 | UBC, RPS27A, UBA52, UBB, RPS27AP11 |
| 219 | FLDSEVSEL | 64151 | NCAPG |
| 220 | SAAEPTPAV | 29803 | REPIN1 |
| 221 | SLLPTEQPRL | 65057 | ACD |
| 222 | LLSEIEEHL | 1653 | DDX1 |
| 223 | FLETNVPLL | 1495, 1496 | CTNNA2, CTNNA1 |
| 224 | ILDEPTNHL | 55324 | ABCF3 |
| 225 | VLFGAVITGA | 100507703, 3105 | LOC100507703, HLA-A |
| 226 | VLNEYFHNV | 1175 | AP2S1 |
| 227 | FLLEQEKTQAL | 11277, 84126 | TREX1, ATRIP |
| 228 | FLNLFNHTL | 28962 | OSTM1 |
| 229 | LLEPFVHQV | 51447 | IP6K2 |
| 230 | HLDEARTLL | 56254 | RNF20 |
| 231 | KMVGDVTGA | 10410, 10581, 8519 | IFITM2, IFITM1, IFITM3 |
| 232 | KILPDLNTV | 9875 | URB1 |
| 233 | QLYNQIIKL | 6731 | SRP72 |
| 234 | KVPEIEVTV | 2969, 2970 | GTF2I, GTF2IP1 |
| 235 | ALADLQEAV | 85461 | TANC1 |
| 236 | GLDSGFHSV | 4034 | LRCH4 |
| 237 | VLYNESLQL | 56254 | RNF20 |

TABLE 3

Peptides useful for, e.g., personalized cancer therapies

| SEQ ID No | Sequence | Gene ID(s) | Official Gene Symbol(s) |
|---|---|---|---|
| 238 | KLLDKPEQFL | 342184 | FMN1 |
| 239 | FLNDIFERI | 337873, 337874 | HIST2H2BC, HIST2H2BD |
| 240 | GLAEFQENV | 57405 | SPC25 |
| 241 | RLYTKLLNEA | 4651 | MYO10 |
| 242 | SLESKLTSV | 9289 | GPR56 |
| 243 | ALAGIVTNV | 11077 | HSF2BP |
| 244 | ILLEKSVSV | 80728 | ARHGAP39 |
| 245 | LLVDDSFLHTV | 253982 | ASPHD1 |
| 246 | TQDDYVLEV | 5793, 5803 | PTPRZ1, PTPRG |
| 247 | ALLNAILHSA | 25926 | NOL11 |
| 248 | GLFAGLGGAGA | 10916 | MAGED2 |
| 249 | KLQDGLLHI | 7076 | TIMP1 |
| 250 | RVLPPSALQSV | 9212 | AURKB |
| 251 | VLDGKVAVV | 6660 | SOX5 |
| 252 | YLLDMPLWYL | 7153 | TOP2A |
| 253 | KLDIKVETV | 55243 | KIRREL |
| 254 | FLMKNSDLYGA | 79801 | SHCBP1 |
| 255 | LLLGERVAL | 23475 | QPRT |
| 256 | VLLDTILQL | 11077 | HSF2BP |
| 257 | VLLNEILEQV | 64151 | NCAPG |
| 258 | FLKNELDNV | 10293 | TRAIP |
| 259 | GLDGIPFTV | 7205 | TRIP6 |
| 260 | QLIDYERQL | 11072 | DUSP14 |
| 261 | GLSEVLVQI | 57553 | MICAL3 |
| 262 | KLAVALLAA | 3576 | IL8 |
| 263 | YALDLSTFL | 8870 | IER3 |
| 264 | KVFDEVIEV | 8908 | GYG2 |
| 265 | ILYDLQQNL | 3783 | KCNN4 |
| 266 | YLAPENGYL | 6625 | SNRNP70 |
| 267 | LLTDNVVKL | 79810 | PTCD2 |
| 268 | ALADLSVAV | 3363 | HTR7 |
| 269 | ALNESLVEC | 55165 | CEP55 |
| 270 | KIWEELSVLEV | 4102, 4105 | MAGEA3, MAGEA6 |
| 271 | SLVQRVETI | 1894 | ECT2 |
| 272 | YLDPLWHQL | 2072 | ERCC4 |
| 273 | ALSELLQQV | 9816 | URB2 |
| 274 | RLHDENILL | 23322 | RPGRIP1L |
| 275 | SLLNQPKAV | 63967 | CLSPN |

TABLE 3-continued

Peptides useful for, e.g., personalized cancer therapies

| SEQ ID No | Sequence | Gene ID(s) | Official Gene Symbol(s) |
|---|---|---|---|
| 276 | FLDSQITTV | 255119 | C4orf22 |
| 277 | KTASINQNV | 81930 | KIF18A |
| 278 | SLITGQDLLSV | 51804 | SIX4 |
| 279 | VVAAHLAGA | 148113 | CILP2 |
| 280 | LLWPSSVPA | 246777, 79400 | SPESP1, NOX5 |
| 281 | GLLENSPHL | 25788 | RAD54B |
| 282 | LLIPFTIFM | 1237 | CCR8 |
| 283 | YTFSGDVQL | 4312 | MMP1 |
| 284 | TIGIPFPNV | 83990 | BRIP1 |
| 285 | YLMDDFSSL | 1293 | COL6A3 |
| 286 | GLNGFNVLL | 144455 | E2F7 |
| 287 | KISDFGLATV | 1111 | CHEK1 |
| 288 | ALLEQTGDMSL | 1063 | CENPF |
| 289 | ILAQDVAQL | 24137 | KIF4A |
| 290 | NVAEIVIHI | 83540 | NUF2 |
| 291 | LLDDIFIRL | 143570 | XRRA1 |
| 292 | ALGDKFLLRV | 4608 | MYBPH |
| 293 | FLDGRPLTL | 83734 | ATG10 |
| 294 | FLLAEDTKV | 10592 | SMC2 |
| 295 | FLPQPVPLSV | 57695 | USP37 |
| 296 | FTAEFLEKV | 79801 | SHCBP1 |
| 297 | GVDDAFYTL | 3845 | KRAS |
| 298 | KLQEEIPVL | 1062 | CENPE |
| 299 | NLLIDDKGTIKL | 983 | CDK1 |
| 300 | QIDDVTIKI | 64151 | NCAPG |
| 301 | RVIDDSLVVGV | 2187 | FANCB |
| 302 | TVLQELINV | 3832 | KIF11 |
| 303 | KLGDFGLLVEL | 9088 | PKMYT1 |
| 304 | VLLAQIIQV | 89797 | NAV2 |
| 305 | TLLKTIIKV | 57545 | CC2D2A |
| 306 | KMLDEILLQL | 5425 | POLD2 |
| 307 | ALAGGITMV | 790 | CAD |
| 308 | KLLSDPNYGV | 79188 | TMEM43 |
| 309 | MQKEITAL | 440915, 58, 59, 60, 644936, 70, 71, 72 | POTEKP, ACTA1, ACTA2, ACTB, ACTC1, ACTG1, ACTG2 |
| 310 | ALASVIKEL | 28981 | IFT81 |
| 311 | KLMDYIDEL | 85444 | LRRCC1 |

TABLE 3-continued

Peptides useful for, e.g., personalized cancer therapies

| SEQ ID No | Sequence | Gene ID(s) | Official Gene Symbol(s) |
|---|---|---|---|
| 312 | TAVGHALVL | 1293 | COL6A3 |
| 313 | LLLDTVTMQV | 22820 | COPG1 |
| 314 | SLFEWFHPL | 2519 | FUCA2 |
| 315 | KLSWDLIYL | 51148 | CERCAM |
| 316 | ALAELLHGA | 26470 | SEZ6L2 |
| 317 | NLAEELEGV | 10763 | NES |
| 318 | SIIEYLPTL | 79915 | ATAD5 |
| 319 | ALSSSQAEV | 3833 | KIFC1 |
| 320 | KIIGIMEEV | 2956 | MSH6 |
| 321 | YLPTFFLTV | 54898 | ELOVL2 |
| 322 | SLHFLILYV | 487, 488 | ATP2A1, ATP2A2 |
| 323 | VVDKTLLLV | 53838 | C11orf24 |
| 324 | SLANNVTSV | 131566 | DCBLD2 |
| 325 | VLVDDDGIKVV | 79022 | TMEM106C |
| 326 | ALSGTLSGV | 4174 | MCM5 |
| 327 | ALADKELLPSV | 84883 | AIFM2 |
| 328 | SLSQELVGV | 24149 | ZNF318 |
| 329 | VLAPRVLRA | 5954 | RCN1 |
| 330 | KMFFLIDKV | 4599 | MX1 |
| 331 | ALSQVTLLL | 392636 | AGMO |
| 332 | AVVEFLTSV | 29102 | DROSHA |
| 333 | RIPAYFVTV | 7407 | VARS |
| 334 | VLLDKIKNLQV | 1293 | COL6A3 |
| 335 | KLASMLETL | 112464 | PRKCDBP |
| 336 | YVDPVITSI | 4233 | MET |
| 337 | FLVDGSSAL | 1293 | COL6A3 |
| 338 | SLNKWIFTV | 339665 | SLC35E4 |

The present invention furthermore generally relates to the peptides according to the present invention for use in the treatment of proliferative diseases, such as, for example, acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, non-Hodgkin lymphoma, non-small cell lung cancer, ovarian cancer, pancreatic cancer, prostate cancer, renal cell cancer, small cell lung cancer, urinary bladder cancer and uterine cancer.

Particularly preferred are the peptides—alone or in combination—according to the present invention selected from the group consisting of SEQ ID NO: 1 to SEQ ID NO: 237. More preferred are the peptides—alone or in combination—selected from the group consisting of SEQ ID NO: 1 to SEQ ID NO: 34 (see Table 1), and their uses in the immunotherapy of melanoma, acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, non-Hodgkin lymphoma, non-small cell lung cancer, ovarian cancer, pancreatic cancer, prostate cancer, renal cell cancer, small cell lung cancer, urinary bladder cancer and uterine cancer, and preferably melanoma.

As shown in the following Tables 4A and 4B, many of the peptides according to the present invention are also found on other tumor types and can, thus, also be used in the immunotherapy of other indications. Also refer to FIGS. 1A-1J and Example 1.

TABLE 4A

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is here defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No. | Sequence | relevant organs/diseases |
|---|---|---|
| 1 | FLDVKELML | RCC, HCC, Uterine Cancer, Gallbladder Cancer, Bile Duct Cancer |
| 2 | VLLGENVEL | NHL, BRCA |
| 7 | NLQEKVPEL | PC, AML, BRCA, Uterine Cancer |
| 8 | SIIPYLLEA | Uterine Cancer |
| 10 | KMTQYITEL | Brain Cancer |
| 11 | TLIELLLPKL | CLL |
| 15 | VLYDPVVGC | CLL, NHL, AML, Uterine Cancer |
| 17 | GVVHGVATV | AML, Urinary bladder cancer |
| 18 | SLADVVDTL | Brain Cancer, CLL, NHL, Uterine Cancer |
| 19 | VLAVLGAVVAV | SCLC, RCC, BRCA, Uterine Cancer |
| 20 | VISPHGIASV | Brain Cancer, Uterine Cancer |
| 21 | FMYNFQLVTL | SCLC, Urinary bladder cancer |
| 22 | KLLELQELVL | NSCLC, Brain Cancer, CRC, BRCA, OC |
| 23 | FLGDPPPGL | CLL, NHL, AML, BRCA, Urinary bladder cancer, Uterine Cancer |
| 24 | SLVAILHLL | NHL, Gallbladder Cancer, Bile Duct Cancer |
| 27 | TLWYVPLSL | CLL, NHL, AML, Uterine Cancer |
| 29 | ILDDVAMVL | CLL, NHL |
| 30 | VLFPMDLAL | RCC |
| 31 | FLPRKFPSL | NSCLC, CRC, CLL, NHL, Esophageal Cancer, OC, Urinary bladder cancer, Uterine Cancer |
| 32 | GLDIITNKV | NHL |
| 36 | SVNGFISTL | AML |
| 57 | GILSFLPVL | CLL, NHL |
| 80 | FADELSHLL | AML |
| 116 | LMDETMKEL | NSCLC, Brain Cancer, HCC, NHL, BRCA, OC, Urinary bladder cancer, Gallbladder Cancer, Bile Duct Cancer |
| 118 | TMIEICEKL | NSCLC, AML, OC |
| 119 | SLGLGFISRV | BRCA |
| 120 | QLMEGKVVL | NHL |
| 121 | FLEDLVPYL | CLL, NHL, AML |
| 122 | YVDDFGVSV | AML |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is here defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No. | Sequence | relevant organs/diseases |
|---|---|---|
| 123 | LLGEGIPSA | Urinary bladder cancer, Uterine Cancer |
| 124 | FLPQKIIYL | GC, BRCA, OC, Uterine Cancer |
| 125 | YLFAFLNHL | AML, OC, Uterine Cancer |
| 126 | SLIDFVVTC | RCC, PC, NHL, OC, Uterine Cancer |
| 127 | TLISDIEAVKA | CLL, NHL, Urinary bladder cancer, Uterine Cancer |
| 128 | ALFPGDVDRL | Brain Cancer, GC, CRC, PC, PrC, BRCA, Esophageal Cancer, Urinary bladder cancer |
| 130 | GLVDVLYTA | NSCLC, RCC, Brain Cancer, BRCA, Esophageal Cancer, Uterine Cancer |
| 133 | ALDPAYTTL | HCC, CLL, NHL, AML, Uterine Cancer |
| 135 | FLDDQETRL | SCLC, CLL, OC |
| 138 | YLDKTFYNL | CRC, CLL, AML |
| 139 | AVDATVNQV | CLL, Uterine Cancer |
| 143 | ILDDSALYL | NHL, Uterine Cancer |
| 144 | SVDEVEISV | CLL |
| 145 | TLPNIYVTL | NHL, AML |
| 146 | GVGPVPARA | PC, AML, Urinary bladder cancer |
| 148 | TLKDIVQTV | CLL, NHL, BRCA |
| 150 | KLFPSPLQTL | SCLC, RCC, PrC, Gallbladder Cancer, Bile Duct Cancer |
| 151 | FLGEPASYLYL | NHL |
| 154 | TLGTATFTV | Urinary bladder cancer, Uterine Cancer |
| 155 | GLAGFFASV | HCC, NHL, BRCA, Esophageal Cancer, Urinary bladder cancer, Uterine Cancer |
| 157 | HLFETISQA | Urinary bladder cancer |
| 158 | KLIPSIIVL | AML |
| 159 | TILATVPLV | SCLC, NHL, AML, BRCA, Urinary bladder cancer, Uterine Cancer, Gallbladder Cancer, Bile Duct Cancer |
| 160 | ALDDISESI | Esophageal Cancer |
| 161 | GLCDSIITI | NSCLC, Brain Cancer, PC, NHL, BRCA, Uterine Cancer |
| 163 | RLMANPEALKI | NHL, OC, Urinary bladder cancer, Uterine Cancer |
| 164 | ALFFQLVDV | SCLC, RCC, AML, BRCA |
| 165 | ALIEVLQPLI | Urinary bladder cancer |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is here defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No. | Sequence | relevant organs/diseases |
|---|---|---|
| 166 | SIIPPLFTV | SCLC, PC, AML, BRCA, OC, Urinary bladder cancer |
| 167 | KVLGDVIEV | RCC, Brain Cancer |
| 168 | KLLAATLLL | RCC, AML, Esophageal Cancer |
| 169 | TLLESIQHV | SCLC, Brain Cancer, CRC, NHL, AML, BRCA, OC |
| 170 | KLKEAVEAI | RCC, CLL, NHL |
| 171 | KVSGVILSV | NHL, AML, BRCA |
| 172 | FLPAGIVAV | CLL, NHL, AML, Urinary bladder cancer, Uterine Cancer |
| 173 | ALDDIIYRA | CLL, NHL |
| 174 | TLLEGLTEL | OC, Uterine Cancer |
| 175 | VLDSVDVRL | RCC, AML |
| 176 | TLYEQEIEV | RCC, Brain Cancer, PC, PrC, NHL |
| 177 | ILWDTLLRL | RCC, AML, Gallbladder Cancer, Bile Duct Cancer |
| 178 | FAYDGKDYIA | BRCA, Esophageal Cancer, OC |
| 179 | ALDDTVLQV | SCLC, Esophageal Cancer |
| 180 | KLAEALYIA | PrC, BRCA, Esophageal Cancer, Urinary bladder cancer |
| 181 | GLIDLEANYL | Brain Cancer, CLL, Uterine Cancer |
| 182 | SVALVIHNV | NHL |
| 183 | FLDSLIYGA | AML, BRCA, Uterine Cancer |
| 184 | VLFSSPPVILL | NSCLC, Brain Cancer, PrC, CLL, NHL, Esophageal Cancer, Urinary bladder cancer |
| 186 | FLDHEMVFL | CLL, NHL, AML, Urinary bladder cancer |
| 187 | SLPRPTPQA | RCC |
| 189 | KALQFLEEV | GC, CRC, BRCA, Uterine Cancer |
| 190 | RLVSLITLL | CLL |
| 191 | YLDKMNNNI | NSCLC, RCC, Brain Cancer, PC, NHL, AML, BRCA, Esophageal Cancer, Urinary bladder cancer, Uterine Cancer, Gallbladder Cancer, Bile Duct Cancer |
| 192 | KLFTQIFGV | HCC |
| 193 | ALDEPTTNL | AML, Urinary bladder cancer, Gallbladder Cancer, Bile Duct Cancer |
| 194 | TLDDIMAAV | NSCLC, SCLC, RCC, Brain Cancer, CRC, CLL, NHL, AML, BRCA, Urinary bladder cancer, Uterine Cancer, Gallbladder Cancer, Bile Duct Cancer |
| 195 | IAAGIFNDL | CLL, AML |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is here defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No. | Sequence | relevant organs/diseases |
| --- | --- | --- |
| 196 | ALEPIDITV | BRCA |
| 197 | ALDSGFNSV | CLL, NHL, Uterine Cancer |
| 198 | EVVDKINQV | RCC |
| 199 | AIHTAILTL | CRC, BRCA |
| 203 | FLNEDISKL | RCC |
| 206 | LLYEDIPDKV | CLL, NHL, Esophageal Cancer, OC, Urinary bladder cancer |
| 207 | VQIGDIVTV | GC, AML, BRCA |
| 208 | YSDDIPHAL | AML |
| 209 | SILDGLIHL | CLL, NHL, AML |
| 210 | LLPELRDWGV | NHL |
| 211 | FLPFLTTEV | HCC, CLL, NHL, AML, OC, Uterine Cancer |
| 212 | LLKDSIVQL | RCC, CLL, Urinary bladder cancer |
| 213 | LLDPTNVFI | PrC, NHL, AML, Urinary bladder cancer |
| 214 | VLMEMSYRL | SCLC, RCC, CRC, CLL, NHL, AML, BRCA, Urinary bladder cancer, Gallbladder Cancer, Bile Duct Cancer |
| 215 | EVISKLYAV | BRCA, Urinary bladder cancer |
| 216 | TLLHFLAEL | CLL, NHL |
| 217 | NMMSGISSV | Brain Cancer, CRC, Urinary bladder cancer, Uterine Cancer, Gallbladder Cancer, Bile Duct Cancer |
| 218 | STLHLVLRL | RCC, GC, HCC, PC |
| 219 | FLDSEVSEL | NHL, AML, Urinary bladder cancer, Uterine Cancer |
| 220 | SAAEPTPAV | Gallbladder Cancer, Bile Duct Cancer |
| 221 | SLLPTEQPRL | NSCLC, SCLC, Brain Cancer, CRC, HCC, PrC, CLL, NHL, Esophageal Cancer, Urinary bladder cancer, Uterine Cancer, Gallbladder Cancer, Bile Duct Cancer |
| 222 | LLSEIEEHL | CLL |
| 223 | FLETNVPLL | Uterine Cancer, Gallbladder Cancer, Bile Duct Cancer |
| 224 | ILDEPTNHL | CLL |

TABLE 4A-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is here defined as higher presentation on the tumor sample as compared to the normal sample with highest presentation. Normal tissues against which over-presentation was tested were: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No. | Sequence | relevant organs/diseases |
|---|---|---|
| 225 | VLFGAVITGA | SCLC, Brain Cancer, HCC, PC, CLL, NHL, AML, BRCA, Esophageal Cancer, Urinary bladder cancer, Uterine Cancer |
| 226 | VLNEYFHNV | SCLC, HCC, BRCA, Esophageal Cancer, Urinary bladder cancer, Uterine Cancer |
| 227 | FLLEQEKTQAL | PrC, CLL, NHL, BRCA, Esophageal Cancer, OC |
| 228 | FLNLFNHTL | CLL |
| 229 | LLEPFVHQV | CLL, NHL, Urinary bladder cancer, Uterine Cancer |
| 230 | HLDEARTLL | CLL, NHL, AML, Uterine Cancer |
| 232 | KILPDLNTV | Brain Cancer, Urinary bladder cancer |
| 233 | QLYNQIIKL | CLL, NHL |
| 234 | KVPEIEVTV | NHL, AML, Uterine Cancer |
| 235 | ALADLQEAV | Brain Cancer, PrC, Uterine Cancer |
| 236 | GLDSGFHSV | PC, NHL, BRCA |
| 237 | VLYNESLQL | NHL |

NSCLC = non-small cell lung cancer,
SCLC = small cell lung cancer,
RCC = kidney cancer,
CRC = colon or rectum cancer,
GC = stomach cancer,
HCC = liver cancer,
PC = pancreatic cancer,
PrC = prostate cancer, leukemia,
BRCA = breast cancer,
OC = ovarian cancer,
NHL = non-Hodgkin lymphoma,
AML = acute myelogenous leukemia,
CLL = chronic lymphatic leukemia

TABLE 4B

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon,, esophagus, eye, gallbladder, heart, kidney, liver, lung, lymph node, white blood cells, pancreas, parathyroid gland, peripheral nerve, peritoneum, pituitary, pleura, rectum, salivary gland, skeletal muscle, skin, small intestine, spleen, stomach, thymus, thyroid gland, trachea, ureter, urinary bladder, vein.

| SEQ ID No | Sequence | Additional Entities |
|---|---|---|
| 1 | FLDVKELML | Brain Cancer, OC |
| 7 | NLQEKVPEL | HNSCC |
| 8 | SIIPYLLEA | HCC, CLL, NHL, HNSCC |
| 13 | IQSETTVTV | HNSCC |
| 14 | VLYEMLYGL | HNSCC |
| 15 | VLYDPVVGC | HNSCC |
| 16 | GLFPSNFVTA | CLL, BRCA, AML |
| 17 | GVVHGVATV | NHL |
| 19 | VLAVLGAVVAV | HCC, CLL, HNSCC |
| 20 | VISPHGIASV | Esophageal Cancer, HNSCC |
| 22 | KLLELQELVL | HNSCC |
| 23 | FLGDPPPGL | Gallbladder Cancer, Bile Duct Cancer, HNSCC |
| 24 | SLVAILHLL | NSCLC, OC, HNSCC |
| 27 | TLWYVPLSL | HNSCC |
| 28 | IVDNTTMQL | GC, AML |
| 30 | VLFPMDLAL | HNSCC |
| 31 | FLPRKFPSL | HNSCC |
| 37 | TLKEYLESL | HCC, Esophageal Cancer |
| 50 | HLDQIFQNL | GC |
| 52 | NLDYAILKL | GC |
| 54 | LLDSGAFHL | GC |
| 56 | ILDELVKSL | GC |
| 58 | ILGDWSIQV | HNSCC |
| 59 | IIDDVMKEL | AML |
| 62 | LLDTTQKYL | AML |
| 64 | SLGPIMLTKI | HCC |
| 68 | FLAEAARSL | HCC |
| 73 | ELDKIYETL | GC |
| 76 | QIDSIHLLL | GC |
| 78 | ALKDLVNLI | HCC |
| 79 | AVDNILLKL | GC |
| 82 | GIDDLHISL | GC |
| 84 | GLDTILQNL | GC, AML |
| 88 | ILDGIIREL | GC |
| 91 | ILLDRLFSV | HNSCC |
| 94 | LLDAFSIKL | GC |
| 100 | NLREILQNV | HCC |
| 102 | RLPDQFSKL | AML |
| 104 | SLDQIIQHL | AML |
| 105 | SLKQTVVTL | HCC |
| 109 | VIDDLIQKL | AML |
| 114 | VVDDIVSKL | GC, AML |
| 115 | YIDDVFMGL | GC |
| 120 | QLMEGKVVL | HNSCC |
| 122 | YVDDFGVSV | GC |
| 123 | LLGEGIPSA | HNSCC |
| 124 | FLPQKIIYL | NHL |
| 126 | SLIDFVVTC | NSCLC, HCC, HNSCC |
| 129 | VLPDDLSGV | HCC |
| 131 | FVDPNGKISL | Urinary bladder cancer, AML |
| 132 | FLDASGAKL | GC |

TABLE 4B-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon,, esophagus, eye, gallbladder, heart, kidney, liver, lung, lymph node, white blood cells, pancreas, parathyroid gland, peripheral nerve, peritoneum, pituitary, pleura, rectum, salivary gland, skeletal muscle, skin, small intestine, spleen, stomach, thymus, thyroid gland, trachea, ureter, urinary bladder, vein.

| SEQ ID No | Sequence | Additional Entities |
|---|---|---|
| 134 | LLDEVLHTM | GC |
| 135 | FLDDQETRL | HNSCC |
| 136 | FAYDGKDYIAL | RCC, Gallbladder Cancer, Bile Duct Cancer, NHL |
| 137 | ILPSNLLTV | HCC, CLL, Urinary bladder cancer, Uterine Cancer, AML, NHL |
| 141 | YVIDPIKGL | Esophageal Cancer |
| 142 | FVDGSAIQV | GC |
| 143 | ILDDSALYL | AML |
| 146 | GVGPVPARA | HCC, NHL |
| 148 | TLKDIVQTV | HCC |
| 150 | KLFPSPLQTL | Urinary bladder cancer |
| 151 | FLGEPASYLYL | HCC, BRCA, OC, Uterine Cancer |
| 153 | RLDEVSREL | GC |
| 159 | TILATVPLV | GC, HNSCC |
| 160 | ALDDISESI | GC, Uterine Cancer |
| 161 | GLCDSIITI | GC, CRC, HCC, HNSCC |
| 163 | RLMANPEALKI | HCC, HNSCC |
| 164 | ALFFQLVDV | HCC, HNSCC |
| 165 | ALIEVLQPLI | GC, HNSCC |
| 166 | SIIPPLFTV | HCC |
| 168 | KLLAATLLL | HCC |
| 169 | TLLESIQHV | HNSCC |
| 170 | KLKEAVEAI | HCC |
| 173 | ALDDIIYRA | HNSCC |
| 175 | VLDSVDVRL | GC |
| 178 | FAYDGKDYIA | RCC, HNSCC |
| 179 | ALDDTVLQV | HNSCC |
| 180 | KLAEALYIA | HNSCC |
| 182 | SVALVIHNV | RCC, GC, HCC |
| 184 | VLFSSPPVILL | HNSCC |
| 186 | FLDHEMVFL | Uterine Cancer |
| 189 | KALQFLEEV | HCC |
| 192 | KLFTQIFGV | SCLC |
| 193 | ALDEPTTNL | CRC, CLL, NHL |
| 195 | IAAGIFNDL | Gallbladder Cancer, Bile Duct Cancer |
| 198 | EVVDKINQV | GC |
| 203 | FLNEDISKL | HCC |
| 204 | RMDEEFTKI | AML |
| 205 | SLKSKVLSV | HCC |
| 206 | LLYEDIPDKV | RCC, HCC, HNSCC |
| 207 | VQIGDIVTV | HNSCC |
| 208 | YSDDIPHAL | Gallbladder Cancer, Bile Duct Cancer |
| 210 | LLPELRDWGV | HCC, CLL |
| 211 | FLPFLTTEV | SCLC, HNSCC |
| 212 | LLKDSIVQL | GC, HCC, AML, NHL |
| 213 | LLDPTNVFI | GC, OC, Esophageal Cancer, HNSCC |
| 214 | VLMEMSYRL | NSCLC, HNSCC |
| 215 | EVISKLYAV | RCC, GC, HCC |
| 217 | NMMSGISSV | BRCA, HNSCC |

TABLE 4B-continued

Peptides according to the present invention and their specific uses in other proliferative diseases, especially in other cancerous diseases. The table shows for selected peptides on which additional tumor types they were found and either over-presented on more than 5% of the measured tumor samples, or presented on more than 5% of the measured tumor samples with a ratio of geometric means tumor vs normal tissues being larger than 3. Over-presentation is defined as higher presentation on the tumor sample as compared to the normal sample with highest presentation. Normal tissues against which over-presentation was tested were: adipose tissue, adrenal gland, artery, bone marrow, brain, central nerve, colon,, esophagus, eye, gallbladder, heart, kidney, liver, lung, lymph node, white blood cells, pancreas, parathyroid gland, peripheral nerve, peritoneum, pituitary, pleura, rectum, salivary gland, skeletal muscle, skin, small intestine, spleen, stomach, thymus, thyroid gland, trachea, ureter, urinary bladder, vein.

| SEQ ID No | Sequence | Additional Entities |
|---|---|---|
| 219 | FLDSEVSEL | SCLC, GC |
| 220 | SAAEPTPAV | HCC |
| 221 | SLLPTEQPRL | HNSCC |
| 224 | ILDEPTNHL | Uterine Cancer |
| 225 | VLFGAVITGA | HNSCC |
| 226 | VLNEYFHNV | NHL, HNSCC |
| 227 | FLLEQEKTQAL | HNSCC |
| 230 | HLDEARTLL | GC |
| 232 | KILPDLNTV | HCC |
| 234 | KVPEIEVTV | GC, CLL, BRCA, OC, Gallbladder Cancer, Bile Duct Cancer |
| 236 | GLDSGFHSV | CLL, AML |
| 237 | VLYNESLQL | CLL, AML |

Thus, another aspect of the present invention relates to the use of at least one peptide according to the present invention according to any one of SEQ ID No. 1, 19, 30, 126, 130, 136, 150, 164, 167, 168, 170, 175, 176, 177, 178, 182, 187, 191, 194, 198, 203, 206, 212, 214, 215, and 218 for the—in one preferred embodiment combined—treatment of RCC.

Thus, another aspect of the present invention relates to the use of at least one peptide according to the present invention according to any one of SEQ ID No. 1, 8, 19, 37, 64, 68, 78, 100, 105, 116, 126, 129, 133, 135, 137, 146, 148, 151, 155, 161, 163, 164, 166, 168, 170, 182, 189, 192, 203, 205, 206, 210, 211, 212, 215, 218, 220, 221, 225, 226, and 232 for the—in one preferred embodiment combined—treatment of HCC.

Thus, another aspect of the present invention relates to the use of at least one peptide according to the present invention according to any one of SEQ ID No. 1, 7, 8, 15, 18, 19, 20, 23, 27, 31, 123, 124, 125, 126, 127, 130, 133, 137, 139, 143, 151, 154, 155, 159, 160, 161, 163, 172, 174, 181, 183, 186, 189, 191, 194, 197, 211, 217, 219, 221, 223, 224, 225, 226, 229, 230, 234, and 235 for the—in one preferred embodiment combined—treatment of uterine cancer.

Thus, another aspect of the present invention relates to the use of at least one peptide according to the present invention according to any one of SEQ ID No. 1, 23, 24, 116, 136, 150, 159, 177, 191, 193, 194, 195, 208, 214, 217, 220, 221, 223, and 234 for the—in one preferred embodiment combined—treatment of gallbladder cancer, and/or bile duct cancer.

Thus, another aspect of the present invention relates to the use of at least one peptide according to the present invention according to any one of SEQ ID No. 2, 8, 11, 15, 17, 18, 23, 24, 27, 29, 31, 32, 57, 116, 120, 121, 124, 126, 127, 133, 135, 136, 137, 138, 139, 143, 144, 145, 146, 148, 151, 155, 159, 161, 163, 169, 170, 171, 172, 173, 176, 181, 182, 184, 186, 190, 191, 193, 194, 195, 197, 206, 209, 210, 211, 212, 213, 214, 216, 219, 221, 222, 224, 225, 226, 227, 228, 229, 230, 233, 234, 236, and 237 for the—in one preferred embodiment combined—treatment of NHL.

Thus, another aspect of the present invention relates to the use of at least one peptide according to the present invention according to any one of SEQ ID No. 2, 7, 16, 19, 22, 23, 116, 119, 124, 128, 130, 148, 151, 155, 159, 161, 164, 166, 171, 178, 180, 183, 189, 191, 194, 196, 199, 207, 214, 215, 217, 225, 226, 227, 234 and 236 for the—in one preferred embodiment combined—treatment of BRCA.

Thus, another aspect of the present invention relates to the use of at least one peptide according to the present invention according to any one of SEQ ID No. 7, 126, 128, 146, 161, 166, 176, 191, 218, 225, and 236 for the—in one preferred embodiment combined—treatment of PC.

Thus, another aspect of the present invention relates to the use of at least one peptide according to the present invention according to any one of SEQ ID No. 7, 15, 16, 17, 23, 27, 28, 36, 59, 62, 80, 84, 102, 104, 109, 114, 118, 121, 122, 125, 131, 133, 137, 138, 143, 145, 146, 158, 159, 164, 166, 168, 169, 171, 172, 175, 177, 183, 186, 191, 193, 194, 195, 204, 207, 208, 209, 211, 212, 213, 214, 219, 225, 230, 234, 236, and 237 for the—in one preferred embodiment combined—treatment of AML.

Thus, another aspect of the present invention relates to the use of at least one peptide according to the present invention according to any one of SEQ ID No. 1, 10, 18, 20, 22, 116, 128, 130, 161, 167, 169, 176, 181, 184, 191, 194, 217, 221, 225, 232, and 235 for the—in one preferred embodiment combined—treatment of brain cancer.

Thus, another aspect of the present invention relates to the use of at least one peptide according to the present invention according to any one of SEQ ID No. 17, 21, 23, 31, 116, 123, 127, 128, 131, 137, 146, 150, 154, 155, 157, 159, 163, 165, 166, 172, 180, 184, 186, 191, 193, 194, 206, 212, 213, 214, 215, 217, 219, 221, 225, 226, 229, and 232 for the—in one preferred embodiment combined—treatment of urinary bladder cancer.

Thus, another aspect of the present invention relates to the use of at least one peptide according to the present invention according to any one of SEQ ID No. 19, 21, 135, 150, 159, 164, 166, 169, 179, 192, 194, 211, 214, 219, 221, 225, and 226 for the—in one preferred embodiment combined—treatment of SCLC.

Thus, another aspect of the present invention relates to the use of at least one peptide according to the present invention according to any one of SEQ ID No. 22, 24, 31, 116, 118, 126, 130, 161, 184, 191, 194, 214, and 221 for the—in one preferred embodiment combined—treatment of NSCLC.

Thus, another aspect of the present invention relates to the use of at least one peptide according to the present invention according to any one of SEQ ID No. 1, 22, 24, 31, 116, 118, 124, 125, 126, 135, 151, 163, 166, 169, 174, 178, 206, 211, 213, 227, and 234 for the—in one preferred embodiment combined—treatment of OC.

Thus, another aspect of the present invention relates to the use of at least one peptide according to the present invention according to any one of SEQ ID No. 20, 31, 37, 128, 130, 141, 155, 160, 168, 178, 179, 180, 184, 191, 206, 213, 221, 225, 226, and 227 for the—in one preferred embodiment combined—treatment of esophageal cancer.

Thus, another aspect of the present invention relates to the use of at least one peptide according to the present invention according to any one of SEQ ID No. 28, 50, 52, 54, 56, 73, 76, 79, 82, 84, 88, 94, 114, 115, 122, 124, 128, 132, 134, 142, 153, 159, 160, 161, 165, 175, 182, 189, 198, 207, 212, 213, 215, 218, 219, 230, and 234 for the—in one preferred embodiment combined—treatment of GC.

Thus, another aspect of the present invention relates to the use of at least one peptide according to the present invention according to any one of SEQ ID No. 22, 31, 128, 138, 161, 169, 189, 193, 194, 199, 214, 217, and 221 for the—in one preferred embodiment combined—treatment of CRC.

Thus, another aspect of the present invention relates to the use of at least one peptide according to the present invention according to any one of SEQ ID No. 128, 150, 176, 180, 184, 213, 221, 227, and 235 for the—in one preferred embodiment combined—treatment of PrC.

Thus, another aspect of the present invention relates to the use of at least one peptide according to the present invention according to any one of SEQ ID No. 7, 8, 13, 14, 15, 19, 20, 22, 23, 24, 27, 30, 31, 58, 91, 120, 123, 126, 135, 159, 161, 163, 164, 165, 169, 173, 178, 179, 180, 184, 206, 207, 211, 213, 214, 217, 221, 225, 226, and 227 for the—in one preferred embodiment combined—treatment of HNSCC.

Thus, another aspect of the present invention relates to the use of at least one peptide according to the present invention according to any one of SEQ ID No. 8, 16, 19, 137, 193, 210, 234, 236, and 237 for the—in one preferred embodiment combined—treatment of CLL.

Thus, another aspect of the present invention relates to the use of the peptides according to the present invention for the—preferably combined—treatment of a proliferative disease selected from the group of melanoma, acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, non-Hodgkin lymphoma, non-small cell lung cancer, ovarian cancer, pancreatic cancer, prostate cancer, renal cell cancer, small cell lung cancer, urinary bladder cancer and uterine cancer.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 237.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No. 237, preferably containing SEQ ID No. 1 to SEQ ID No. 34, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is a cellular therapy, a vaccine or a protein based on a soluble TCR or antibody.

The present invention further relates to a use according to the present invention, wherein said cancer cells are melanoma, acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, non-Hodgkin lymphoma, non-small cell lung cancer, ovarian cancer, pancreatic cancer, prostate cancer, renal cell cancer, small cell lung cancer, urinary bladder cancer and uterine cancer, and preferably melanoma cells.

The present invention further relates to biomarkers based on the peptides according to the present invention, herein called "targets" that can be used in the diagnosis of cancer, preferably melanoma. The marker can be over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

Both therapeutic and diagnostic uses against additional cancerous diseases are disclosed in the following more detailed description of the underlying expression products (polypeptides) of the peptides according to the invention.

ACOT7 has been found to be up-regulated in melanoma, where it may be involved in preventing lipotoxicity (Sumantran et al., 2015).

ACSL3 encodes for acyl-CoA synthetase long-chain family member 3. ACSL3 is over-expressed in lung cancer and based on preclinical investigation is a promising new therapeutic target in lung cancer (Pei et al., 2013). The up-regulated expression of ACSL3 can serve as a potential biomarker of estrogen receptor-specific breast cancer risk (Wang et al., 2013b).

APOE is involved in cholesterol transport and may be important in enabling tumor cell to fulfill their high cholesterol requirements. It was found to be over-expressed in various types of cancer such as gastric cancer, anaplastic thyroid carcinoma, prostate cancer and colorectal cancer (Yasui et al., 2005; Ito et al., 2006; Sakashita et al., 2008; Shi et al., 2015b; Kang et al., 2016; Yencilek et al., 2016). Elevated serum levels of APOE were shown to be associated with metastasis and poor prognosis in non-small cell lung cancer. Furthermore they have been suggested as a prognostic marker in breast cancer and as a marker to monitor the efficiency of chemotherapy in small cell lung cancer (Shi et al., 2016; Xu et al., 2016b; Luo et al., 2016).

Loss of ARID2 through inactivating mutations was related to tumor progression and recurrence in gastric cancer, hepatocellular carcinoma and non-small cell lung carcinoma (Manceau et al., 2013; You et al., 2015; Aso et al., 2015).

ARNT2 has been found to be over-expressed in non-small cell lung cancer, hepatocellular cancer, breast cancer and oral squamous cell carcinoma. It acts as a tumor suppressor during cancer progression because over-expression has been determined to increase overall survival and promote cell apoptosis (Qin et al., 2011a; Li et al., 2015d; Yang et al., 2015; Kimura et al., 2016).

ATG2B encodes autophagy related 2B, a protein essential for autophagosome formation and regulation of lipid droplet volume and distribution (Velikkakath et al., 2012). ATG2B frameshift mutations are common in gastric and colon carcinomas with high microsatellite instability (Kang et al., 2009).

ATM is a tumor suppressor which is frequently mutated in a broad range of human cancers including lung, colorectal, breast and hematopoietic cancers (Weber and Ryan, 2014). Loss of ATM has been associated with the increased risk of various cancers including, breast, colorectal, prostate, lung and pancreatic ductal adenocarcinoma (Swift et al., 1987; Geoffroy-Perez et al., 2001; Angele et al., 2004; Roberts et al., 2012; Grant et al., 2013; Russell et al., 2015). Studies have shown that IL-8 was able to rescue cell migration and invasion defects in ATM-depleted cells (Chen et al., 2015b). Low level of ATM protein was correlated with poor metastasis-free survival in breast cancer patients. In addition, miR-203 and miR-421 over-expression may be involved in ATM de-regulation in these patients (Bueno et al., 2014; Rondeau et al., 2015).

BNC1 was shown to be part of a ten-gene methylation signature which was hyper-methylated in colorectal adenomas and carcinomas (Patai et al., 2015). BNC1 was shown to be associated with prostate cancer since it was frequently methylated and thus inactivated in prostate cancer cell lines (Devaney et al., 2013). BNC1 was shown to be one of many potential targets that were aberrantly methylated in chronic lymphocytic leukemia, renal cell carcinoma and T-cell and B-cell childhood acute lymphoblastic leukemia (Tong et al., 2010; Morris et al., 2010; Dunwell et al., 2009). BNC1 was shown to play a role in the progression of primary breast tumors to brain metastases. Knock-down of BNC1 resulted in an increase of migratory and invasive potential of breast cancer cell lines. Thus, BNC1 may be useful as a prognostic marker and a novel therapeutic target (Pangeni et al., 2015). BNC1 was shown to be associated with TGF-β1 signaling (Feuerborn et al., 2015). BNC1 was shown to be associated with poorer survival in clear cell renal cell carcinoma and poorer prognosis in renal cell carcinoma (Morris et al., 2010; Ricketts et al., 2014). BNC1 was shown to be frequently methylated in stage I invasive pancreatic cancers. Thus, BNC1 serves as a potential biomarker to detect early-stage pancreatic cancer (Yi et al., 2013). BNC1 was shown to be up-regulated in squamous cell carcinomas of the head and neck (Boldrup et al., 2012). BNC1 was shown to be transcriptionally regulated by the p53-family member p63 in squamous cell carcinomas of the head and neck (Boldrup et al., 2012).

Several studies hit that BNC2 functions as a tumor suppressor gene in esophageal adenocarcinoma, ovarian cancer and glioblastoma. The gene is frequently deleted and/or expression is reduced (Nord et al., 2009; Akagi et al., 2009; Cesaratto et al., 2016). BNC2 was found to be down-regulated in hepatocellular carcinoma and also it was frequently deleted, which might be one important reason for its lower expression level (Wu et al., 2016).

BOP1 is associated with ovarian cancer and colorectal cancer (Wrzeszczynski et al., 2011; Killian et al., 2006). BOP1 was shown to be a target gene of Wnt/β-catenin which induced EMT, cell migration and experimental metastasis of colorectal cancer cells in mice. Thus, BOP1 may serve as a therapeutic target in the treatment of colorectal cancer metastasis (Qi et al., 2015). BOP1 is associated with hepatocellular carcinoma invasiveness and metastasis (Chung et al., 2011). BOP1 was described as a member of a molecular pathway associated with cell cycle arrest in a gastric cancer cell line upon treatment with mycophenolic acid, indicating a potential association of BOP1 with the anticancer activity of the drug (Dun et al., 2013a; Dun et al., 2013b). BOP1 may be a possible marker for rectal cancer (Lips et al., 2008). BOP1 was described as a potential oncogene in ovarian cancer (Wrzeszczynski et al., 2011). BOP1 was shown to be up-regulated in hepatocellular carcinoma (Chung et al., 2011). BOP1 was shown to be associated with microvascular invasion, shorter disease-free survival and metastasis in hepatocellular carcinoma (Chung et al., 2011). BOP1 was described as a subunit of the PeBoW complex, which is essential for cell proliferation and maturation of the large ribosomal subunit. Over-expression of BOP1 was shown to inhibit cell proliferation (Rohrmoser et al., 2007). Expression of an amino-terminally truncated form of BOP1 resulted in down-regulation of G(1)-specific Cdk2 and Cdk4 kinase complexes, retinoblastoma and cyclin A while Cdk inhibitors p21 and p27 were up-regulated. This led to an arrest in the G(1) phase (Pestov et al., 2001).

CAPN3 expression was found to be down-regulated in melanoma cells which play a role in the acquisition of a highly invasive phenotype (Huynh et al., 2009; Ruffini et al., 2013; Moretti et al., 2015). CAPN3 has been shown to complex with Digestive-organ-expansion-factor (Dev) and together mediate degradation of tumor suppressor p53 (Zhu et al., 2014b).

CCT6A is associated with testicular germ cell tumors and malignant melanomas (Tanic et al., 2006; Alagaratnam et al., 2011).

CCT8 was shown to be up-regulated in hepatocellular carcinoma (Huang et al., 2014c). CCT8 is associated with histologic grades, tumor size and poor prognosis of hepatocellular carcinoma (Huang et al., 2014c).

RPI-1 and dasatinib treatment target CD109 to inhibit cancer cell proliferation (Caccia et al., 2011). CD109 is over-expressed in nasopharyngeal carcinoma, laryngeal squamous cell carcinoma, non-small cell lung cancer, pancreatic cancer, myxofibrosarcoma, esophageal squamous cell carcinoma, head and neck cancer, and (triple-negative) breast cancer (Ni et al., 2012; Tao et al., 2014; Zhang et al., 2014a; Dong et al., 2015a; Emori et al., 2015; Haun et al., 2014; Hoover et al., 2015; Jia et al., 2016). CD109 might be used as prognostic biomarker in nasopharyngeal carcinoma, vulvar squamous cell carcinoma, triple-negative breast cancer, hepatocellular carcinoma, and gallbladder squamous cell/adenosquamous carcinoma. Secreted CD109 may be used as serum prognostic marker (Ye et al., 2016; Ozbay et al., 2013; Sakakura et al., 2014; Tao et al., 2014; Dong et al., 2015b; Jia et al., 2016). CD109 is expressed on a rare group of circulating endothelial cells which may be used as prognostic marker in glioblastoma (Mancuso et al., 2014; Cuppini et al., 2013). Reduced expression of CD109 promotes tumor growth. It was shown to be down-regulated in uterine carcinosarcoma (Ye et al., 2016; Semczuk et al., 2013). CD109 promotes hepatocellular carcinoma proliferation and is correlated with poor prognosis (Zong et al., 2016). CD109 over-expression is associated with surgical state, poor prognosis, and metastasis (Emori et al., 2013; Emori et al., 2015; Karhemo et al., 2012). CD109 inhibits TGF-beta1 signaling and promotes EGF signaling human glioblastoma cells (Man et al., 2012; Zhang et al., 2015).

CSNK2A1 has been shown to be involved in tumorigenesis by phosphorylating other proteins in breast cancer, colorectal cancer and gastric carcinoma. CSNK2A1 expression was shown to be an independent prognostic indicator for gastric carcinoma, breast cancer, and clear cell renal cell carcinoma (Kim et al., 2012; Bae et al., 2015; Kren et al., 2015; Rabjerg et al., 2016; Bae et al., 2016). CSNK2A1 has been suggested as a therapeutic target in chronic myeloid leukemia and glioblastoma. Inhibiting Casein Kinase II as part of a proposed novel BCR-ABL/CK2/PTEN pathway promotes PTEN reactivation, which promotes apoptosis induction in cancer cells (Lee et al., 2013; Zheng et al., 2013; Morotti et al., 2015). CSNK2A1 was shown to be frequently mutated in adult T-cell leukemia (Kataoka et al., 2015).

DYNC2H1 was shown to be up-regulated in glioblastoma multiforme (Yokota et al., 2006).

EIF3E might play a role in the carcinogenesis of oral squamous cell carcinoma (Yong et al., 2014). EIF3E is essential for proliferation and survival of glioblastoma cells (Sesen et al., 2014). EIF3E has an oncogenic role in breast cancer progression. Decreased EIF3E expression causes epithelial to mesenchymal transition in breast epithelial cells (Gillis and Lewis, 2013; Grzmil et al., 2010). EIF3E expression level is significantly increased in bladder cancer (Chen et al., 2011). EIF3E is involved in non-small lung carcinoma (Marchetti et al., 2001).

Expression of human endogenous retroviruses (HERV) env proteins such as ERV3-1 was shown to be significantly increased in the blood of primary breast cancer patients, suggesting the potential use of HERV env genes as a diagnosis marker for primary breast cancer (Rhyu et al., 2014). ERV3-1 was shown to be significantly over-expressed in less differentiated endometrial carcinoma, liver and lung tumor tissues (Strissel et al., 2012; Ahn and Kim, 2009). Loss of ERV3-1 mRNA expression was described as being associated with susceptibility to choriocarcinoma (Kato et al., 1988).

Epigenetic inactivation of EXTL1 has been found in leukemia and non-melanoma cancer cells. In contrast, high expression of EXTL1 was reported to be associated with poor prognosis in patients with multiple myeloma. EXTL1 was shown to have altered N-glycosylation in human aggressive breast cancer cell lines (Drake et al., 2012; Busse-Wicher et al., 2014). Deletion of EXTL1 was detected in several neuroblastoma and it was suggested as a tumor suppressor gene, but no clear evidence was found of EXTL1 being involved in the causal investigation of neuroblastoma (Mathysen et al., 2004).

FCGR2B is the pre-dominant Fc-receptor on B-cells and therefore a target for immunotherapy. Via activation of FCGR2B the monoclonal antibody Rituximab inhibits Kv1.3 channels that play an important role in modulating lymphocyte proliferation and apoptosis, and induces apoptosis in human B lymphoma cells (Shah et al., 2013; Rankin et al., 2006; Wang et al., 2012). FCGR2B polymorphisms have been found to correlate with clinical response to specific immunotherapy such as rituximab and idiotype vaccination in follicular lymphoma. Also, polymorphisms in FCGR2B have been associated with binding affinity of natural killer cells to trastuzumab, an antibody used in treatment of HER-positive breast cancer (Musolino et al., 2008; Weng et al., 2009; Norton et al., 2014). FCGR2B expression prevents the lysis of human metastatic melanoma cells by NK cell-mediated antibody-dependent cellular cytotoxicity, making it a marker of human metastatic melanoma (Cassard et al., 2008).

A correlation of FCGR2C polymorphisms and/or expression levels to the response to certain immunotherapies has been found in breast cancer, neck squamous cell carcinoma and metastatic renal cell carcinoma (Petricevic et al., 2013; Trivedi et al., 2016; Erbe et al., 2016).

A single nucleotide polymorphism in FMN1 is associated with an increased risk of prostate cancer (Lisitskaia et al., 2010).

The FLCN/FNIP1/FNIP2 complex regulates kidney cell proliferation rate and is functionally lost in the Birt-Hogg-Dube syndrome which is a hereditary hamartoma syndrome (Schmidt and Linehan, 2015b; Schmidt and Linehan, 2015a; Hasumi et al., 2016). FNIP1 is involved in invariant natural killer T cell development (Park et al., 2014). FNIP1 promotes lysosome recruitment and the Rag interactions of the tumor suppressor FLCN (Petit et al., 2013). FNIP1 is involved in mTORC1 activation via RagC/D (Linehan et al., 2010; Tsun et al., 2013). FNIP1 is involved in kidney tumor suppression and may be used as therapeutic target (Hasumi et al., 2015).

FOXD1 has been shown to be over-expressed in breast cancer, clear cell sarcoma of the kidney, gastric cancer and Hodgkin lymphoma. The over-expression may increase cell proliferation and has been suggested as a therapeutic target. In gastric cancer and hepatocellular carcinoma it has been found to be part of the transcriptional regulatory network, whose downstream target genes are involved in cancerogenesis (Nagel et al., 2014; Karlsson et al., 2014; Zhao et al., 2015b; Xu et al., 2016a; Chen et al., 2016). Up-regulated FOXD1 expression levels have been determined as a prognostic marker for poor outcome in non-small cell lung cancer (Nakayama et al., 2015).

FOXD2 was found to be highly expressed in prostate cancer and lymph node metastases (Heul-Nieuwenhuijsen et al., 2009). FOXD2 has been shown to be differently methylated in serrated adenocarcinoma compared to other colorectal cancer types, suggesting it as a biomarker to identify this particular type of colorectal cancer (Conesa-Zamora et al., 2015).

GBF1 has been identified as a host factor that enhances adenovirus cancer cell killing. Cancer cells are susceptible to oncolytic viruses, making them a cancer treatment option, and GBF1 knock-down or chemical inhibition enhances melanoma or epithelial cancer cell killing by adenovirus infection by triggering unfolded protein response (Prasad et al., 2014).

GNAI2 over-expression has been observed in ovarian cancer and hepatocellular carcinoma. More specifically, GNAI2 expression decreased in early stage ovarian cancer, while it increased in advanced cancers, implicating GNAI2 as a critical regulator of oncogenesis and an upstream driver of cancer progression in ovarian cancer (Peters et al., 2005; Raymond, Jr. et al., 2014). GNAI2 expression is regulated by microRNA-138, that is frequently de-regulated in various cancers like tongue squamous cell carcinoma and in turn GNAI2 is up-regulated. GNAI2 is also a functional target of miR-30d in hepatocellular carcinoma cells (Jiang et al., 2011; Yao et al., 2010).

In gastric cancer high GOLGA2 expression levels were found to have a positive correlation with the pathological differentiation and tumor node metastasis stage, and also predict shorter overall survival. Furthermore, GOLGA2 contributes to epithelial-mesenchymal transition by up-regulating the expression of SNAI1 (Zhao et al., 2015a). GOLGA2 expression is progressively lost in colorectal cancer and the loss disrupts the cells apical-basal polarity as well as front-rear polarity and may play affect other processes relevant for tumorigenesis (Baschieri and Farhan, 2015; Baschieri et al., 2015). GOLGA2 has been suggested as a therapeutic target, because down-regulation decreased angiogenesis and cell cancer invasion in tumorigenesis in lung cancer (Chang et al., 2012).

GOLGA6A is located on one of the regions which were found to inherit polymorphisms in Patients with Paget's disease of bone (Chung and Van, 2012). GOLGA6A was identified as a fusion partner for PAX5 being an early player in leukemogenesis (Coyaud et al., 2010).

The HERC2/OCA2 region on chromosome 15q13.1 is one of several loci that predispose to cutaneous melanoma (Amos et al., 2011; Xiao et al., 2014). HERC2 regulates the stability of different DNA repair factors including CHK1, p53 and BRCA1 (Bekker-Jensen et al., 2010; Cubillos-Rojas et al., 2014; Zhu et al., 2014a; Peng et al., 2015).

HLA-B reduced expression has been associated with poorer survival in esophageal cancer. However, in gastric and colorectal cancer, the prognostic value of HLA-B remains conflicting and it can be both up- and down-regulated (Powell et al., 2012; Gallou et al., 2016).

HLA class I molecules are ligands for killer immunoglobulin like receptors (KIR), that negatively regulate NK cells and T cells and lack of KIR-HLA interactions have been associated with potent NK-mediated antitumor efficacy and increased survival in acute myeloid leukemia. In ovarian cancer and non-small cell lung cancer certain genotypes of HLA-C have an effect cancer development (Romagne et al., 2009; Wisniewski et al., 2012; Giebel et al., 2014). Reduced expression of HLA-C has been associated with poorer survival in esophageal cancer. However, in gastric and colorectal cancer the prognostic value of HLA-C remains conflicting and it can be both up- and down-regulated. In colorectal cancer most tumor cells mimic the HLA phenotypes of their normal counterparts to evade NK-mediated immunosurveillance (Gao et al., 2013; Powell et al., 2012; Doubrovina et al., 2003; Benevolo et al., 2007).

HMCN1 was found to be up-regulated in human soft tissue tumors and might represent a novel candidate biomarker and therapeutic target (Sarver et al., 2015). HMCN1 was found to be involved in skin development and epithelial morphogenesis and showed a down-regulated expression in multiple drug-resistant ovarian cancer cells (Januchowski et al., 2014; Westcot et al., 2015). Furthermore, HMCN1 is related to cell polarity and somatically mutated in gastric and colorectal cancers (Lee et al., 2015).

IDH3G was found to be differentially expressed in gastric cancer and might be associated with drug resistance (Zhou et al., 2015).

IL4I1 protein expression is very frequent in tumors. IL4I1 was detected in tumor-associated macrophages of different tumor entities, in neoplastic cells from lymphomas and in rare cases of solid cancers mainly mesothelioma (Carbonnelle-Puscian et al., 2009). IL4I1 up-regulation in human Th17 cells limits their T-cell receptor (TCR)-mediated expansion by blocking the molecular pathway involved in the activation of the IL-2 promoter and by maintaining high levels of Tob1, which impairs entry into the cell cycle (Santarlasci et al., 2014).

IPO9 encodes the protein importin 9, which acts as a scaffolding protein and is important in regulating cellular function in both the immune system and the nervous system, by activating signaling pathways like the Ras/Erk pathway or by enhancing mitochondria-mediated apoptosis (Murrin and Talbot, 2007; Wang et al., 2002).

De-regulation of ITGA10 has been shown to be a downstream effect of the de-regulation of other cancer genes like ERG in leukemia, miR-375 in lung cancer or EPHB4 in prostate cancer (Mertens-Walker et al., 2015; Mochmann et al., 2014; Jin et al., 2015). ITGA10 has been found to be under-expressed in solid osteoblasts that have frequent inactivation of the pRb pathway (Engel et al., 2013).

Single nucleotide polymorphism in the ITPR2 gene were correlated with risk of renal cell carcinoma in a Chinese population. Likewise, two common variants in linkage disequilibrium, rs718314 and rs1049380 in the ITPR2 gene were identified as novel susceptibility loci for renal cell carcinoma. Moreover, over-expression of ITPR2 was observed in normal acute myeloid leukemia patients compared to healthy persons (Wu et al., 2012; Shi et al., 2015a; Zhang et al., 2016b). In normal acute myeloid leukemia, elevated levels of ITPR2 expression was associated with shorter overall survival and event-free survival (Shi et al., 2015a).

ITPR3 is over-expressed in several cancer types including colorectal, gastric and breast cancer and directly related to cancer progression and the aggressiveness of the tumor (Shibao et al., 2010; Mound et al., 2013; Sakakura et al., 2003). Akt can protect cells in an ITPR3-dependent manner from apoptosis through reducing the Ca2+ release from the endoplasmatic reticulum (Marchi et al., 2012).

Researchers have observed that the levels of mRNA expression for the KIFAP3 gene were significantly reduced in tumorous tissue samples relative to non-cancerous renal cortex tissue samples. Others reported over-expression of KIFAP3 protein in breast cancers. Another group has shown that the expression of the KIFAP3 gene was significantly changed between breast cancer cells treated with recombinant bromelain and the control cells (Gotoh et al., 2014; Fouz et al., 2014; Telikicherla et al., 2012).

MACROD2 showed somatic alterations (often intragenic deletions) in liver cancer, colorectal cancer, gastric cancer and esophageal squamous cell carcinoma (Briffa et al., 2015; Tada et al., 2010; van den Broek et al., 2015; Hu et al., 2016; Fujimoto et al., 2016). MACROD2 increases p300 binding to estrogen response elements in a subset of estrogen receptor-alpha (ER) regulated genes and shows an increased expression in primary breast tumors where it is associated with worse overall survival (Mohseni et al., 2014). The MACROD2 gene was found to be deleted in various cancer types, but a tumor suppressor role of MACROD2 could not be established (Rajaram et al., 2013). MACROD2 plays a role in MARylation and is able to 'read' and 'erase' this modification on target proteins (Feijs et al., 2013).

Over-expression of MAGEC2 increases the level of cyclin E and promotes G1-S transition and cell proliferation (Hao et al., 2015). MAGEC2 promotes proliferation and resistance to apoptosis in Multiple Myeloma suggesting that MAGEC2-specific immunotherapies have the potential to eradicate the most malignant cells (Lajmi et al., 2015). MAGEC2, an epithelial-mesenchymal transition inducer, is associated with breast cancer metastasis. Multivariate analyses showed that MAGEC2 expression was an independent risk factor for patient overall survival and metastasis-free survival (Yang et al., 2014).

The above mentioned increased expression of METAP2 and the anti-cancer effect of METAPA2 inhibitors has been studied in various cancers, including non-small cell lung cancer, pilocytic astrocytoma, colon and colorectal cancer and neuroblastoma (Morowitz et al., 2005; Selvakumar et al., 2009; Ho et al., 2013; Shimizu et al., 2016).

Although the exact biological functions of MFI2 remain elusive, a growing number of roles have been attributed to the protein, including iron transport/metabolism, angiogenesis, proliferation, cellular migration and tumorigenesis. MFI2 over-expressing tumors have been suggested as targets that are sensitive to antibody-drug conjugates (Dunn et al., 2006; Smith et al., 2006; Suryo et al., 2012). MIF2 levels have been shown to be significantly increased at the plasma level of colorectal cancer, making it a potential serological marker. It may also be involved in transformation from benign tumor to malignancy and is a marker of an invasive tumor phenotype (Shin et al., 2014; Dus-Szachniewicz et al., 2015).

It has been reported that MTCH2 is a suppressed by miR-135b, that is up-regulated in breast cancers and it seems that miR-135b and its targets, MID1 and MTCH2, are relevant coordinators of mammary gland tumor progression (Arigoni et al., 2013). MTCH2 seems to be involved in rapid ABT-737 induced apoptosis in lymphoma and primary leukemia cells. ABT-737 induces MTCH2, resulting in mitochondrial matrix swelling and rupture of the outer mitochondrial membrane (Vogler et al., 2008).

Antibodies to poly(A) polymerase were observed in serum samples from human patients with leukemia, polycythemia vera and Wilms tumor (Stetler et al., 1981).

MYO5A was shown to be associated with a novel trafficking pathway in melanoma that promotes tumor resistance through Akt2/MYO5A activation (Fernandez-Perez et al., 2013). MYO5A was up-regulated in invasive non-functioning pituitary adenomas and may thus serve as a useful marker of tumor invasiveness (Galland et al., 2010). MYO5A mRNA expression was increased in a number of highly metastatic cancer cell lines and metastatic colorectal cancer tissues. Furthermore, suppression of MYO5A in those cancer cells impede their migration and metastasis capabilities both in vitro and in vivo (Lan et al., 2010). MYO5A was shown to be applicable in a four-gene model for the identification occult nodal metastasis in oral squamous cell carcinoma (Mendez et al., 2011).

NAA30 plays an important role in growth and survival of glioblastoma-initiating cells possibly by regulating hypoxia response (HIF1α), levels of p-MTOR (Ser2448) and the p53 pathway (Mughal et al., 2015). NAA30 is differentially expressed during development or in carcinomas of higher eukaryotes and is thus suggested to be more highly expressed in cells undergoing rapid protein synthesis (Polevoda and Sherman, 2003).

NAV2 encodes a member of the neuron navigator gene family, which may play a role in cellular growth and migration. NAV2 was shown to be specifically expressed in a group of colon cancers and treatment of colon-cancer cells with antisense oligonucleotides for NAV2 induced apoptosis (Ishiguro et al., 2002).

In liver cancer cells the loss of p53 has been shown to be responsible for NES expression and in breast cancer NES contributes to cancer development by enhancing Wnt/beta-catenin activation (Zhao et al., 2014; Tschaharganeh et al., 2014). Increased NES expression has been reported in various tumor cells, including pancreatic ductal adenocarcinoma, malignant melanoma, uterine, prostate, breast and liver cancers. NES expression correlates with aggressive features, metastasis and is a biomarker for poor prognosis. Furthermore, NES may be a marker for newly synthesized tumor vessels and has also been suggested as a therapeutic target to inhibit tumor angiogenesis (Ishiwata et al., 2011; Su et al., 2013; Matsuda et al., 2016; Hope et al., 2016).

NMES is highly expressed in testis and some types of human cancer, like pancreatic cancer and breast cancer, and is associated with innate resistance to gemcitabine in pancreatic cancer cells (Parris et al., 2010; Li et al., 2012a; Li et al., 2012b).

NUP160-SLC43A3 is a recurrent fusion oncogene in angiosarcoma and associated with tumor progression (Shimozono et al., 2015).

The P2RX7 system is an important pro-apoptosis modulator in epithelial cells and plays a role in chemoprevention in papillomas and epithelial cancers. Statins, cholesterol-lowering drugs, may reduce the invasiveness and risk of aggressive prostate cancer via P2RX7. Also, P2X7 single-nucleotide polymorphisms could be exploited as diagnostic biomarkers for the development of tailored therapies (Fu et al., 2009; Gorodeski, 2009; Ghalali et al., 2014; Roger et al., 2015; De et al., 2016). P2RX7 expression levels are elevated in primary bone tumors as well as in other malignancies such as multiple myeloma, neuroblastoma, breast, and prostate cancer. There is evidence that P2RX7 triggers NFATc1, PI3K/Akt, ROCK, and VEGF pathways in osteoblasts promoting tumor development (Adinolfi et al., 2012). P2RX7 is a potential prognostic marker in hepatocellular carcinoma, where high peritumoral P2X7 expression indicates unfavorable overall survival (Liu et al., 2015a).

PARVA is over-expressed in colorectal cancer, where it correlates significantly with tumor invasion, lymph node metastasis, and disease stage, as well as with the over-expression of integrin-linked kinase, p-AKT, and nuclear β-catenin and the down-regulation of E-cadherin (Bravou et al., 2015). Over-expression of PARVA promoted tumorigenicity, angiogenesis and metastasis of lung adenocarcinoma by influencing ILK signaling and a subsequent phosphorylation of Akt and GSK3beta (Huang et al., 2015). PARVA was frequently over-expressed in ovarian cancer, non-small cell lung carcinoma, prostate cancer and human hepatocellular carcinoma, where its over-expression positively correlated with tumor size, stage, and metastasis by enhancing survivin protein, β-catenin, and mammalian target of rapamycin pathways and suppressing p53 (Orr et al., 2012; Davidson et al., 2013; Augustin et al., 2013; Ng et al., 2013; Seydi et al., 2015). Furthermore, it was shown that PARVA is frequently regulated by phosphorylation in breast cancer cells leading to matrix degradation and cell invasion via regulation of Rho GTPase signaling (Pignatelli et al., 2012). PARVA was found to be up-regulated in prostate cancer and invasive lobular carcinoma being able to form an IPP complex with integrin-linked kinase and PINCH, that functions as a signaling platform for integrins (Kim et al., 2015b; Aakula et al., 2016; Ito et al., 2014).

PBK promotes lung cancer resistance to EGFR tyrosine kinase inhibitors by phosphorylating and activating c-Jun (Li et al., 2016b). Over-expression of PBK confers malignant phenotype in prostate cancer via the regulation of E2F1 (Chen et al., 2015a). Targeting PBK decreases growth and survival of glioma initiating cells in vitro and attenuates tumor growth in vivo (Joel et al., 2015). PBK inhibitor induces complete tumor regression in xenograft models of human cancer through inhibition of cytokinesis (Matsuo et al., 2014).

Elevated levels of PI4KA were observed in hepatocellular carcinoma versus normal liver tissue. In addition, the PI4KA gene was detected in pancreatic cancer cell line (Ishikawa et al., 2003; Ilboudo et al., 2014). Patients suffering from hepatocellular carcinoma with higher PI4KA mRNA concentrations had a higher risk of tumor recurrence as well as shorter disease-specific survival (Ilboudo et al., 2014). Recently, PI4KA has been identified to be involved in cell proliferation and resistance to cisplatin treatment in a medulloblastoma cell line. Others have revealed that PI4KA plays a crucial role in invasion and metastasis in pancreatic cancer (Ishikawa et al., 2003; Guerreiro et al., 2011).

PLA2G4A expression is up-regulated in colorectal cancer, bladder carcinoma, which provides COX-2 with arachidonic acid, resulting in increased prostaglandin levels. Up-regulation may occur due to prolonged inflammatory conditions (Osterstrom et al., 2002; Dong et al., 2005; Parhamifar et al., 2005; Shi et al., 2006). In gastric cancer increased PLA2G4A and COX-2 expression were both associated with unfavorable survival and PLA2G4A might serve as a promising target for future therapeutic approaches to gastric cancer combined with COX-2 inhibitors. Also, inhibition of PLA2G4A may sensitize tumors to radiation therapy (Linkous et al., 2009; Zhang et al., 2013).

PLEC encodes the plakin family member plectin, a protein involved in the cross-linking and organization of the cytoskeleton and adhesion complexes (Bouameur et al., 2014). PLEC is over-expressed in colorectal adenocarcinoma, head and neck squamous cell carcinoma and pancreatic cancer (Lee et al., 2004; Katada et al., 2012; Bausch et al., 2011).

PMEL was described as a target for anti-body drug conjugate therapy in melanoma (Chen et al., 2012). PMEL was shown to be associated with paclitaxel and cisplatin resistance in melanoma (Hertzman et al., 2013). PMEL was described as one out of nine proteins applicable in a targeted selected reaction monitoring assay which provides potential advancements in the diagnosis of malignant melanoma (Welinder et al., 2014a).

POLM is an error-prone DNA repair enzyme that is prone to induce template/primer misalignments and mis-incorporation. High expression levels are thought to be involved in somatic hyper-mutation in a Burkitt's lymphoma-derived B cell line (Ruiz et al., 2004; Fernandez and Albar, 2012).

Some researchers have observed a significant increase in PRKAR1A expression in undifferentiated thyroid carcinomas compared to normal thyroid tissue and differentiated thyroid tumors. On the contrary, down-regulation of PRKAR1A expression was reported in a subset of odontogenic tumors. Another group revealed that PRKAR1A could be involved in the pathogenesis of odontogenic myxomas as well as in sporadic adrenocortical adenomas (Bertherat et al., 2003; Perdigao et al., 2005; Ferrero et al., 2015; Sousa et al., 2015).

PSMA2 is differentially expressed in plasma cells of multiple myeloma and immunoglobulin light chain amyloidosis (Abraham et al., 2005). PSMA2 is down-regulated in methotrexate-resistant breast cancer MCF-7 cells (Chen et al., 2014c).

PSMB7 expression is increased in most cancer types, along with other constitutive proteasome genes. In breast cancer and colorectal cancer high PSMB7 expression has been reported as an unfavorable prognostic marker. In hepatocellular carcinoma and breast cancer it may contribute to chemotherapy resistance (Rho et al., 2008; Munkacsy et al., 2010; Tan et al., 2014; Rouette et al., 2016).

PTPN14 induces TGF-beta signaling, regulates endothelial-mesenchymal transition, and organogenesis (Wyatt and Khew-Goodall, 2008). PTPN14 is down-regulated in cholangiocarcinoma and is inversely correlated with clinical-pathological features and survival (Wang et al., 2015d; Wang et al., 2015c). PTPN14 inhibits trafficking of soluble and membrane-bound proteins, resulting in prevention of metastasis (Belle et al., 2015). PTPN14 negatively regulates the oncoprotein Yes-associated protein (YAP), a key protein in the Hippo pathway, which is responsible for organ size and tumorigenesis (Liu et al., 2013; Huang et al., 2013; Lin et al., 2013). Loss-of-function mutations in PTPN14 are involved in neuroblastoma relapse, breast cancer, and colorectal cancer (Laczmanska and Sasiadek, 2011; Wang et al., 2004; Schramm et al., 2015; Wyatt and Khew-Goodall, 2008).

RAD21 is a component of the cohesin complex, crucial for chromosome segregation and DNA repair. RAD21 is over-expressed in gastrointestinal tumors, colorectal carcinoma, advanced endometrial cancer, prostate cancer and breast cancer (Atienza et al., 2005; Deb et al., 2014; Porkka et al., 2004; Supernat et al., 2012; Xu et al., 2014).

RAD50 forms the MRN complex with MRE11 and NBS1, a complex that binds to DNA and displays numerous enzymatic activities that are required for non-homologous joining of DNA ends and is important for double-strand break repair, cell cycle checkpoint activation, telomere maintenance and meiotic recombination. Mutations in this gene are the cause of Nijmegen breakage syndrome-like disorder (RefSeq, 2002). RAD50 deletion appears to be common in basal-like breast cancer and ovarian cancer and was associated with significantly better overall survival. Deletion often occurs together with deletions of BRCA1, RB1, TP53, PTEN and INPP4B, and RAD50 and INPP4B expression levels have a synergistic influence on breast cancer survival, possibly through their effects on treatment response (Weigman et al., 2012; Dai et al., 2015; Zhang et al., 2016a). In colorectal cancer over-expression of RAD50 may be involved in cancer progression. RAD50 becomes highly expressed if transcription factor BTF3 is over-expressed and over-expression in primary tumors seems to be related to early tumor stage, better differentiation, high inflammatory infiltration and p53 over-expression (Wang et al., 2013a; Gao et al., 2008). RAD50 has been found to be frequently mutated in hereditary breast and ovarian cancer, colorectal cancer and in metastatic non-small cell lung RAD50 mutation contributes to a curative response to systemic combination therapy (Al-Ahmadie et al., 2014; Rajkumar et al., 2015).

A RANBP2-ALK gene fusion is detectable in different cancer entities including leukemias and lymphomas (Lim et al., 2014; Chen and Lee, 2008; Maesako et al., 2014; Lee et al., 2014). RANBP2 sumoylates Topo II alpha in mitosis, and this modification is required for its proper localization to inner centromeres. Thereby, RANBP2 plays an important role in preventing chromosome segregation errors (Navarro and Bachant, 2008; Dawlaty et al., 2008).

Researchers have identified the RAPGEF6 as an upstream activator of Rap1 required for the maturation of adherent junctions in the lung carcinoma cells (Dube et al., 2008). Another group has demonstrated the formation of a complex between JAM-A, AF-6 and the RAPGEF6 in breast cancer cells and in primary cultures from breast cancer patients (McSherry et al., 2011).

RBM4, a splicing factor over-expressed in several entities, alternatively splices RGPD1 (Markus et al., 2016). CG-1521, an anti-proliferative cancer drug, up-regulates RGPD1 expression (Chatterjee et al., 2013).

RBM4, a splicing factor over-expressed in several entities, alternatively splices RGPD2 (Markus et al., 2016). NEAT1-RGPD2, RGPD2-FASN, and RGPD2-MALAT1 are fusion transcripts detected in primary breast cancer (Kim et al., 2015a). RGPD2 may be an ALK fusion partner in acute myelomonocytic leukemia (Lim et al., 2014). CG-1521, an anti-proliferative cancer drug, up-regulates RGPD2 expression (Chatterjee et al., 2013). RGPD3 encodes RANBP2-like and GRIP domain containing 3 which is located in a cluster of Ran-binding protein related genes on chromosome 2 which arose through duplication in primates. The encoded protein contains an N-terminal TPR (tetratricopeptide repeat) domain, two Ran-binding domains, and a C-terminal GRIP domain (golgin-97, RanBP2alpha, Imh1p and p230/golgin-245) domain (RefSeq, 2002). RGPD3 is a cancer gene with 3D HotMAPS regions in pancreatic adenocarcinoma (Tokheim et al., 2016). RGPD3 may be a target gene of HOXB7 (Heinonen et al., 2015). Dioscin alters RGPD3 expression in colon cancer cells (Chen et al., 2014a). A gene fusion transcript of ANAPC1 with RGPD3 has been reported in nasopharyngeal carcinoma (Chung et al., 2013). CG-1521, an anti-proliferative cancer drug, up-regulates RGPD3 expression (Chatterjee et al., 2013). RGPD3 is mutated in gastrotintestinal stromal tumors and meningiomas (Brastianos et al., 2013).

RGPD8 is predominantly altered in prostate cancer and glioma (Meszaros et al., 2016). RGPD8 is part of a run of homozygosity associated with thyroid cancer (Thomsen et al., 2016). CG-1521, an anti-proliferative cancer drug, up-regulates RGPD8 expression (Chatterjee et al., 2013).

As RICTOR is able to interact with mTOR, it is playing a major role in the PI3K/AKt/mTOR signaling pathway and was found to be up-regulated in various cancer types such as small cell lung cancer, large-cell neuroendocrine carcinoma of the lung, breast cancer pancreatic cancer and colorectal cancer (Suh et al., 2016; Morrison et al., 2016; Miyoshi et al., 2016; Visuttijai et al., 2016; Sticz et al., 2016; Driscoll et al., 2016; Sakre et al., 2016). RICTOR polymorphisms were found in non-small cell lung cancer and breast cancer and were related to the progression and metastasis of these cancers (Zhou et al., 2016; Wang et al., 2016b). RICTOR takes part in forming the PRICKLE1-MINK1-RICTOR complex, which is required for activation of AKT, regulation of focal adhesions and cancer cell migration (Daulat et al., 2016). RICTOR over-expression is associated with the carcinogenesis and progression of colorectal cancer and can be an independent indicator for evaluating the prognosis of colorectal cancer patients (Wang et al., 2016a).

ROPN1 is a cancer-testis antigen expressed in prostate cancer, acute myeloid leukemia, multiple myeloma and basal like breast cancer and has been suggested as a potential serological biomarker for prostate cancer. As a cancer-testis antigen it represents an attractive target for tumor immunotherapy (Chiriva-Internati et al., 2011; Atanackovic et al., 2011; Ivanov et al., 2013; Adeola et al., 2016).

S100A1 was found to be down-regulated in oral cancer and bladder tumors, but up-regulated in ovarian cancer and in gastric cancer up-regulation of S100A1 was caused by over-expression of prion protein PRNP (Hibbs et al., 2004; Liang et al., 2007; Yao et al., 2007; Tyszkiewicz et al., 2014). S100A1 may be a potentially powerful marker to differentiate subtypes of cancer. It can help distinguish chromophobe renal cell carcinoma from renal oncocytoma and is up-regulated in basal-type breast cancers compared to non-basal types. S100A1 may also serve as a marker for poor prognosis of endometrioid subtypes of cancer (Li et al., 2007; DeRycke et al., 2009; McKiernan et al., 2011).

SERPINE2 creates tumor-promoting conditions in the tumor microenvironment and regulates tumor matrix deposition in multiple ways. It also is involved in vascular mimicry (Smirnova et al., 2016). SERPINE2 is over-expressed in breast cancer, prostate cancer and testicular cancer and promotes the development of metastasis. In gastric cancer SERPINE2 up-regulation may contribute to the aggressive phenotype and has been suggested as a novel prognostic factor and as an anticancer target, e.g. through inhibition by monoclonal antibodies (Smirnova et al., 2016; Nagahara et al., 2010; Kousted et al., 2014; Wang et al., 2015b; Wagenblast et al., 2015). In prostate cancer SER- PINE2 expression appears to down-regulate distinct oncogenic pathways and inhibit hedgehog-signaling and angiogenesis (McKee et al., 2013; McKee et al., 2015).

SGK1 expression is rapidly up-regulated by glucocorticoid administration which may decrease chemotherapy effectiveness in ovarian cancer. In turn, the isoflavinoid Genistein has been found to have an inhibitory effect on colorectal cancer by reducing SGK1 expression (Melhem et al., 2009; Qin et al., 2015). Increased SGK1 expression has been found in several human tumors, including prostate carcinoma, non-small cell lung cancer and hepatocellular carcinoma. SGK1 has anti-apoptotic properties and regulates cell survival, proliferation and differentiation via phosphorylation of MDM2, which leads to the ubiquitination and proteasomal degradation of p53. Direct SGK1 inhibition can be effective in hepatic cancer therapy, either alone or in combination with radiotherapy (Lang et al., 2010; Abbruzzese et al., 2012; Isikbay et al., 2014; Talarico et al., 2015).

SGK3 function was shown to be associated with the oncogenic driver INPP4B in colon cancer and in breast cancer (Gasser et al., 2014; Guo et al., 2015). SGK3 was described as a down-stream mediator of phosphatidylinositol 3-kinase oncogenic signaling which mediates pivotal roles in oncogenic progress in various cancers, including breast cancer, ovarian cancer and hepatocellular carcinoma (Hou et al., 2015). SGK3 was described to serve as a hallmark interacting with numerous molecules in cell proliferation, growth, migration and tumor angiogenesis (Hou et al., 2015). SGK3 was shown to promote hepatocellular carcinoma growth and survival through inactivating glycogen synthase kinase 3 beta and Bcl-2-associated death promoter, respectively (Liu et al., 2012). SGK3 was shown to be associated with poor outcome in hepatocellular carcinoma patients (Liu et al., 2012). Thus, SGK3 may provide a prognostic biomarker for hepatocellular carcinoma outcome prediction and a novel therapeutic target (Liu et al., 2012). SGK3 was described as an important mediator of PDK1 activities in melanoma cells which contributes to the growth of BRAF-mutant melanomas and may be a potential therapeutic target (Scortegagna et al., 2015). SGK3 was described as an androgen receptor transcriptional target that promotes prostate cell proliferation through activation of p70 S6 kinase and up-regulation of cyclin D1 (Wang et al., 2014). Knock-down of SGK3 was shown to decrease LNCaP prostate cancer cell proliferation by inhibiting G1 to S phase cell cycle progression (Wang et al., 2014). SGK3 was shown to be associated with estrogen receptor expression in breast cancer and its expression was shown to be positively correlated with tumor prognosis (Xu et al., 2012).

It was shown that SHC4 represents an EGFR-binding partner and Grb2 platform and acts non-canonically to promote phosphorylation of select EGFR residues (Wills et al., 2014). SHC4 interacts with membrane receptors, is involved in central cascades including MAPK and Akt, and is unconventionally contributed to oxidative stress and apoptosis (Wills and Jones, 2012).

Transcription levels of SLC4A5 were found to be significantly higher in therapy resistant ovary carcinoma cells (PelzI et al., 2015). SLC4A5 represents a pigmentation gene that is involved in phenotypic traits including fair skin, light-colored eyes, and poor tanning ability, which are all linked to melanoma risk (Nan et al., 2009; Pho and Leachman, 2010).

SLC29A1 is a major transporter involved in gemcitabine and 5-fluorouracil intracellular uptake in chemotherapy and it was found to be up-regulated in gastric cancer and colorectal carcinoma. In pancreatic cancer it has been validated as a predictive marker for the benefit of gemcitabine therapy and has been suggested to be the same in cholangiocarcinoma (Shimakata et al., 2016; Hagmann et al., 2010; North et al., 2014; Nordh et al., 2014; Brandi et al., 2016; Kunicka et al., 2016). SLC29A1 has been identified as a marker to distinguish metastases of clear cell renal cell carcinoma to the adrenal from primary adrenal cortical neoplasms or normal adrenal (Li et al., 2015a).

SLC45A2 was shown to be highly enriched in melanoma cell lines (Bin et al., 2015). Single nucleotide polymorphisms in SLC45A2 were associated with cutaneous melanoma risk, as well as cutaneous basal cell carcinoma and squamous cell carcinoma (Antonopoulou et al., 2015; Stacey et al., 2009).

SNCA is widely expressed in a variety of brain tumors, such as medulloblastoma, neuroblastoma, pineoblastoma, and ganglioma and also in the peripheral cancers, including ovarian cancer and breast cancer. Determining the levels of SNCA expression in tissues may be a biomarker to detect metastatic melanoma (Fujita et al., 2007; Matsuo and Kamitani, 2010; Welinder et al., 2014b). The SNCA promotor is frequently hyper-methylated in colorectal cancers and adenomas and might be a suitable biomarker for early non-invasive detection (Lind et al., 2011; Li et al., 2015e).

Knock-down of SNRPN in the Daoy human medulloblastoma cell line was shown to reduce proliferation and colony formation ability, indicating that SNRPN may be a potential novel target for the development of pharmacological therapeutics in human medulloblastoma (Jing et al., 2015). Knock-down of SNRPN in the BxPC-3 pancreatic adenocarcinoma cell line was shown to reduce the proliferation ability and impaired cell colony formation. Its depletion was also shown to led to S phase cell cycle arrest and apoptosis (Ma et al., 2015). Depletion of SNRPN in BxPC-3 pancreatic adenocarcinoma cells was also shown to lead to S phase cell cycle arrest and apoptosis (Ma et al., 2015). Knock-down of SNRPN was shown to result in a significant decrease in both invasion and proliferation in specifically Caucasian prostate cancer cell lines (Devaney et al., 2015).

SNX14 is down-regulated upon rasV12/E1A transformation of mouse embryonic fibroblasts and may be associated with tumor development (Vasseur et al., 2005).

SOX5 is up-regulated in breast cancer cells and hepatocellular carcinoma. It induces epithelial to mesenchymal transition by transactivation of Twist1 (Moon et al., 2014; Wang et al., 2015a). SOX5 is expressed in glioma tissues, but not in normal adult tissues, except in testis. Additionally, antibodies against SOX5 were detected in sera from 8 of 27 glioma patients and patients who showed IgG responses against SOX5 exhibited significantly better survival periods than patients without SOX5 antibodies (Ueda et al., 2007). Together with other novel hypermethylated genes (AKR1B1, CHST10, ELOVL4, STK33, ZNF304) SOX5 was found as a potential methylation biomarker and therapeutic target of vincristine in colorectal carcinoma (Pei et al., 2014).

SOX6 encodes a member of the D subfamily of sex determining region y-related transcription factors that are characterized by a conserved DNA-binding and their ability to bind the minor groove of DNA. SOX6 is a transcriptional activator that is required for normal development of the central nervous system, chondrogenesis and maintenance of cardiac and skeletal muscle cells. It interacts with other family members to cooperatively activate gene expression (RefSeq, 2002). SOX6 functions as a tumor suppressor in myeloid leukemia, hepatocellular carcinoma and esophageal squamous cell carcinoma (ESCC). SOX6 was found to be frequently down-regulated in ESCC and down-regulation correlates with poor survival. The tumor-suppressive mechanism of SOX6 was associated with its role in G1/S cell-cycle arrest by up-regulating expressions of p53 and p21 and down-regulating expressions of cyclins (Qin et al., 2011b; Cantu et al., 2011; Guo et al., 2013). SOX-6 is considered a cancer-testis gene and was found to be expressed in a high percentage of human central nervous system tumors, including meningiomas and glioblastomas and could be the potential target of immunotherapy for central nervous system tumors (Lee et al., 2008).

SRGAP1 was shown to be associated with glioblastoma multiforme in the cell lines U87-IM3 and U251-IM3, familial forms of non-medullary thyroid carcinoma, papillary thyroid carcinoma and epithelial ovarian cancer (He et al., 2013; Chen et al., 2014b; Pereira et al., 2015; Koo et al., 2015).

SRGAP2 has been found to be up-regulated in an investigation of the molecular characteristics of recurrent triple-negative breast cancer and was associated with cell adhesion and motility (Tsai et al., 2015).

SRGAP3 expression is down-regulated in several breast cancer cell lines and SRGAP3 exhibits has tumor suppressor-like activity in all mammary epithelial cells, likely through its activity as a negative regulator of Rac1 (Lahoz and Hall, 2013). In pilocytic astrocytomas a tandem duplication at 3p25 was observed, which produces an in-frame oncogenic fusion between SRGAP3 and RAF1 hat may contribute to tumorigenesis (Jones et al., 2009).

The human ortholog of SSR4 was shown to be differentially expressed in the opossum melanoma cell lines TD6b and TD15L2 and up-regulated in tumors of advanced stages, implicating SSR4 as a candidate gene with potential functions that might be associated with ultraviolet-induced melanomagenesis and metastasis (Wang and VandeBerg, 2004). The mRNA level of SSR4 was shown to be enriched in the osteosarcoma cell lines OHS, SaOS-2 and KPDXM compared to normal osteoblast cells (Olstad et al., 2003).

STAM has been found to be over-expressed in locally advanced cervical cancer and in tumors in young patients with spinal ependymomas (Korshunov et al., 2003; Campos-Parra et al., 2016). STAM is a downstream target of ZNF331, a gene down-regulated in gastric cancer, which then leads to down-regulation of STAM as well (Yu et al., 2013). STAM has been associated with the unfavorable 11q deletion in chronic lymphocytic leukemia (Aalto et al., 2001).

STAT2 operates as a positive regulator in the transcriptional activation response elicited by IFNs (Steen and Gamero, 2012). STAT2 may regulate tumor cell response to interferons (Shodeinde et al., 2013). A link between STAT2 and tumorigenesis was observed in transgenic mice lacking STAT2 (Yue et al., 2015) or expressing constitutively IFN-α in the brain (Wang et al., 2003).

TANC1 was found to play a role in regenerating damaged muscle and is suggested to influence the development of late radiation-induced damage in prostate cancer patients (Fachal et al., 2014). Ectopic TANC1 expression in rhabdomyosarcoma (RMS) causes misregulated myoblast fusion proteins, which might represent candidates for targeted RMS therapy (Avirneni-Vadlamudi et al., 2012).

Families presenting with Oral-Facial-Digital syndrome type 6 (OFD6) have likely pathogenic mutations in TMEM17 causing ciliogenesis defects (Li et al., 2016a).

TMEM209 is widely expressed in lung cancer, in which it is localized to the nuclear envelope, Golgi apparatus, and the cytoplasm of lung cancer cells. Ectopic over-expression of TMEM209 promoted cell growth, whereas TMEM209 attenuation was sufficient to block growth (Fujitomo et al., 2012).

It was shown that TSPAN14 is significantly up-regulated in cancer cells treated with coumarin- and benzimidazole-containing compounds, which possess anti-tumor activity by inducing caspase-dependent apoptosis (Liu et al., 2015b). TSPAN14 was found to be up-regulated in grade 1 lung tumors, suggesting that structural changes of these genes could play a role in cancer promotion (Bankovic et al., 2010).

UTP20 expression is decreased in metastatic human breast tumor cell lines (Schwirzke et al., 1998; Goodison et al., 2003). UTP20 is expressed at high levels in gastric cancer tissues and premalignant lesions implicating the involvement of UTP20 in cell transformation (Xing et al., 2005).

VGLL4 acts as a tumor suppressor in gastric cancer, lung cancer and esophageal squamous cell carcinoma by negatively regulating the YAP-TEAD transcriptional complex and inhibiting YAP induced tumorigenesis. VGLL4 has been shown to be down-regulated during the progression of gastric cancer and esophageal squamous carcinoma (Zhang et al., 2014c; Jiao et al., 2014; Jiang et al., 2015; Li et al., 2015c). VGLL4 may also inhibit epithelial-mesenchymal transition in gastric cancer through the Wnt/beta signaling pathway (Li et al., 2015b).

WDFY3 was shown to be down-regulated in colorectal cancer (Piepoli et al., 2012).

It was shown that WDR35 is one of the key genes for chronic myeloid leukemia progression and is differentially methylated in acute lymphoblastic leukemia (Nordlund et al., 2012; Zhang et al., 2014b). WDR35 regulates cilium assembly by selectively regulating transport of distinct cargoes, is essential for the entry of many membrane proteins into the cilium and is mutated in several cargo transport mediated diseases (Fu et al., 2016). WDR35 expression is regulated by the CaMKK/AMPK/p38 MAPK pathway as well as by NF-kappaB (Harato et al., 2012; Huang et al., 2014b; Huang et al., 2014a).

WDR6 inhibits the colony formation of cervical cancer cells via regulation of the LKB1 pathway and stimulation of p27 promoter activity (Xie et al., 2007). WDR6 plays an important role in hepatocarcinogenesis and can be used as a detection marker of hepatocellular proliferative lesions (Yafune et al., 2013).

WDR7 expression is de-regulated by copy number alterations in gastric cancer and shows an elevated expression in numerous malignant cell lines (Junnila et al., 2010; Sanders et al., 2000).

ZBTB3 may play a critical role in cancer cell growth in human melanoma, lung carcinoma, and breast carcinoma via the ROS detoxification system (Lim, 2014). Suppression of ZBTB3 activates a caspase cascade, including caspase-9, -3, and PARP leading to cellular apoptosis and might therefore represent a potential target for selective cancer treatments (Lim, 2014).

ZMYM1 is a major interactor of ZNF131 which acts in estrogen signaling and breast cancer proliferation (Oh and Chung, 2012; Kim et al., 2016).

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, or 13 or longer, and in case of MHC class II peptides (elongated variants of the peptides of the invention) they can be as long as 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 5

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |

TABLE 5-continued

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86% (calculated from www.allelefrequencies.net).

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

percent identity=$100[1-(C/R)]$ wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 237 or a variant thereof which is 88% homologous to SEQ ID NO: 1 to SEQ ID NO: 237, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 237. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 237, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or -II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or -II is substantially changed, or is negatively affected, when compared to the non-modified peptide.

The amino acid residues that do not substantially contribute to interactions with the T-cell receptor can be modified by replacement with other amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 6

Variants and motif of the peptides according to SEQ ID NO: 1, 10, and 20

| | Position | | | | | | | | | |
|---|---|---|---|---|---|---|---|---|---|---|
| | 1 | 2 | 3 | 4 | 5 | 6 | 7 | 8 | 9 | 10 |
| SEQ ID No 1 | F | L | D | V | K | E | L | M | L | |
| Variant | | | | | | | | | V | |
| | | | | | | | | | I | |
| | | | | | | | | | A | |
| | | M | | | | | | | V | |
| | | M | | | | | | | I | |
| | | M | | | | | | | | |
| | | M | | | | | | | A | |
| | | A | | | | | | | V | |
| | | A | | | | | | | I | |
| | | A | | | | | | | | |
| | | A | | | | | | | A | |
| | | V | | | | | | | V | |
| | | V | | | | | | | I | |
| | | V | | | | | | | | |
| | | V | | | | | | | A | |
| | | T | | | | | | | V | |
| | | T | | | | | | | I | |
| | | T | | | | | | | | |
| | | T | | | | | | | A | |
| | | Q | | | | | | | V | |
| | | Q | | | | | | | I | |
| | | Q | | | | | | | | |
| | | Q | | | | | | | A | |
| SEQ ID No 10 | K | M | T | Q | Y | I | T | E | L | |
| Variant | | L | | | | | | | V | |
| | | L | | | | | | | I | |
| | | L | | | | | | | | |
| | | L | | | | | | | A | |
| | | | | | | | | | V | |
| | | | | | | | | | I | |
| | | | | | | | | | A | |
| | | A | | | | | | | V | |
| | | A | | | | | | | I | |
| | | A | | | | | | | | |
| | | A | | | | | | | A | |
| | | V | | | | | | | V | |
| | | V | | | | | | | I | |
| | | V | | | | | | | | |
| | | V | | | | | | | A | |
| | | T | | | | | | | V | |
| | | T | | | | | | | I | |
| | | T | | | | | | | | |
| | | T | | | | | | | A | |
| | | Q | | | | | | | V | |
| | | Q | | | | | | | I | |
| | | Q | | | | | | | | |
| | | Q | | | | | | | A | |
| SEQ ID No 20 | V | I | S | P | H | G | I | A | S | V |
| Variant | | L | | | | | | | | |
| | | L | | | | | | | | I |
| | | L | | | | | | | | L |
| | | L | | | | | | | | A |
| | | M | | | | | | | | |
| | | M | | | | | | | | I |
| | | M | | | | | | | | L |
| | | M | | | | | | | | A |
| | | A | | | | | | | | |
| | | A | | | | | | | | I |

TABLE 6-continued Variants and motif of the peptides according to SEQ ID NO: 1, 10, and 20

| Position |   |   |   |   |   |   |   |   |   |
|---|---|---|---|---|---|---|---|---|---|
| 1 | 2 | 3 | 4 | 5 | 6 | 7 | 8 | 9 | 10 |
|   | A |   |   |   |   |   |   |   | L |
|   | A |   |   |   |   |   |   |   | A |
|   | V |   |   |   |   |   |   |   |   |
|   | V |   |   |   |   |   |   |   | I |
|   | V |   |   |   |   |   |   |   | L |
|   | V |   |   |   |   |   |   |   | A |
|   | T |   |   |   |   |   |   |   |   |
|   | T |   |   |   |   |   |   |   | I |
|   | T |   |   |   |   |   |   |   | L |
|   | T |   |   |   |   |   |   |   | A |
|   | Q |   |   |   |   |   |   |   |   |
|   | Q |   |   |   |   |   |   |   | I |
|   | Q |   |   |   |   |   |   |   | L |
|   | Q |   |   |   |   |   |   |   | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 7.

TABLE 7

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 µM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 237.

"Consisting essentially of" shall mean that a peptide according to the present invention, in addition to the sequence according to any of SEQ ID NO: 1 to SEQ ID NO 237 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897, 445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidation, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (www.sigma-aldrich.com) provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention.

Another embodiment of the present invention relates to a non-naturally occurring peptide wherein said peptide consists or consists essentially of an amino acid sequence according to SEQ ID No: 1 to SEQ ID No: 237 and has been synthetically produced (e.g. synthesized) as a pharmaceutically acceptable salt. Methods to synthetically produce peptides are well known in the art. The salts of the peptides according to the present invention differ substantially from the peptides in their state(s) in vivo, as the peptides as generated in vivo are no salts. The non-natural salt form of the peptide mediates the solubility of the peptide, in particular in the context of pharmaceutical compositions comprising the peptides, e.g. the peptide vaccines as disclosed herein. A sufficient and at least substantial solubility of the peptide(s) is required in order to efficiently provide the peptides to the subject to be treated. Preferably, the salts are pharmaceutically acceptable salts of the peptides. These salts according to the invention include alkaline and earth alkaline salts such as salts of the Hofmeister series comprising as anions PO$_4^{3-}$, SO$_4^{2-}$, CH$_3$COO$^-$, Cl$^-$, Br$^-$, NO$_3$, ClO$_4^-$, I$^-$, SCN$^-$ and as cations NH$_4^+$, Rb$^+$, K$^+$, Na$^+$, Cs$^+$, Li$^+$, Zn$^{2+}$, Mg$^{2+}$, Ca$^{2+}$, Mn$^{2+}$, Cu$^{2+}$ and Ba$^{2+}$. Particularly salts are selected from (NH$_4$)$_3$PO$_4$, (NH$_4$)$_2$HPO$_4$, (NH$_4$)H$_2$PO$_4$, (NH$_4$)$_2$SO$_4$, NH$_4$CH$_3$COO, NH$_4$Cl, NH$_4$Br, NH$_4$NO$_3$, NH$_4$ClO$_4$, NH$_4$I, NH$_4$SCN, Rb$_3$PO$_4$, Rb$_2$HPO$_4$, RbH$_2$PO$_4$, Rb$_2$SO$_4$, Rb$_4$CH$_3$COO, Rb$_4$Cl, Rb$_4$Br, Rb$_4$NO$_3$, Rb$_4$ClO$_4$, Rb$_4$I, Rb$_4$SCN, K$_3$PO$_4$, K$_2$HPO$_4$, KH$_2$PO$_4$, K$_2$SO$_4$, KCH$_3$COO, KCl, KBr, KNO$_3$, KClO$_4$, KI, KSCN, Na$_3$PO$_4$, Na$_2$HPO$_4$, NaH$_2$PO$_4$, Na$_2$SO$_4$, NaCH$_3$COO, NaCl, NaBr, NaNO$_3$, NaClO$_4$, NaI, NaSCN, ZnCl$_2$ Cs$_3$PO$_4$, Cs$_2$HPO$_4$, CSH$_2$PO$_4$, Cs$_2$SO$_4$, CSCH$_3$COO, CsCl, CsBr, CSNO$_3$, CsClO$_4$, CSI, CsSCN, Li$_3$PO$_4$, Li$_2$HPO$_4$, LiH$_2$PO$_4$, Li$_2$SO$_4$, LiCH$_3$COO, LiCl, LiBr, LiNO$_3$, LiClO$_4$, LiI, LiSCN, Cu$_2$SO$_4$, Mg$_3$(PO$_4$)$_2$, Mg$_2$HPO$_4$, Mg(H$_2$PO$_4$)$_2$, Mg$_2$SO$_4$, Mg(CH$_3$COO)$_2$, MgCl$_2$, MgBr$_2$, Mg(NO$_3$)$_2$, Mg(ClO$_4$)$_2$, MgI$_2$, Mg(SCN)$_2$, MnCl$_2$, Ca$_3$(PO$_4$), Ca$_2$HPO$_4$, Ca(H$_2$PO$_4$)$_2$, CaSO$_4$, Ca(CH$_3$COO)$_2$, CaCl$_2$, CaBr$_2$, Ca(NO$_3$)$_2$, Ca(ClO$_4$)$_2$, CaI$_2$, Ca(SCN)$_2$, Ba$_3$(PO$_4$)$_2$, Ba$_2$HPO$_4$, Ba(H$_2$PO$_4$)$_2$, BaSO$_4$, Ba(CH$_3$COO)$_2$, BaCl$_2$, BaBr$_2$, Ba(NO$_3$)$_2$, Ba(ClO$_4$)$_2$, BaI$_2$, and Ba(SCN)$_2$. Particularly preferred are NH acetate, MgCl$_2$, KH$_2$PO$_4$, Na$_2$SO$_4$, KCl, NaCl, and CaCl$_2$, such as, for example, the chloride or acetate (trifluoroacetate) salts.

Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995) (cf. Example 1, FIGS. 1A to 1J).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural tumor-associated peptides (TUMAPs) recorded from melanoma samples (N=18 A*02-positive samples) with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from 18 melanoma patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from melanoma tissue samples were purified and HLA-associated peptides were isolated and analyzed by LC-MS (see examples). All TUMAPs contained in the present application were identified with this approach on primary melanoma samples confirming their presentation on primary melanoma.

TUMAPs identified on multiple melanoma and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Besides over-presentation of the peptide, mRNA expression of the underlying gene was tested. mRNA data were obtained via RNASeq analyses of normal tissues and cancer tissues (cf. Example 2, FIGS. 2A-2C). An additional source of normal tissue data was a database of publicly available RNA expression data from around 3000 normal tissue samples (Lonsdale, 2013). Peptides which are derived from proteins whose coding mRNA is highly expressed in cancer tissue, but very low or absent in vital normal tissues, were preferably included in the present invention.

The present invention provides peptides that are useful in treating cancers/tumors, preferably melanoma that over- or exclusively present the peptides of the invention. These peptides were shown by mass spectrometry to be naturally presented by HLA molecules on primary human melanoma samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy skin cells or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from melanoma, but not on normal tissues (see Example 1).

HLA-bound peptides can be recognized by the immune system, specifically T lymphocytes. T cells can destroy the cells presenting the recognized HLA/peptide complex, e.g. melanoma cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to a peptide-HLA molecule complex with a binding affinity (KD) of about 100 µM or less, about 50 µM or less, about 25 µM or less, or about 10 µM or less. More preferred are high affinity TCRs having binding affinities of about 1 µM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, an peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to the peptides according to the invention can be enhanced by methods well known in the art.

The present description further relates to a method of identifying and isolating a TCR according to the present description, said method comprising incubating PBMCs from HLA-A*02-negative healthy donors with A2/peptide monomers, incubating the PBMCs with tetramer-phycoerythrin (PE) and isolating the high avidity T-cells by fluorescence activated cell sorting (FACS)—Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with peptide of interest, incubating PBMCs obtained from the transgenic mice with tetramer-phycoerythrin (PE), and isolating the high avidity T-cells by fluorescence activated cell sorting (FACS)—Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient. In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed. In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced (Schmitt et al., 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion) (Schmitt et al., 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutic such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 237, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs).

In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly- (I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore, different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example, a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed, aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 237, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 237, or a variant thereof which is at least 88% homologous (preferably identical) to SEQ ID NO: 1 to SEQ ID NO: 237 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 237 or a variant thereof which is at least 88% homologous (preferably identical) to SEQ ID NO: 1 to SEQ ID NO: 237, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 237.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of melanoma.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, wherein the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 237 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are melanoma cells or other solid or hematological tumor cells such as acute myelogenous leukemia, breast cancer, bile duct cancer, brain cancer, chronic lymphocytic leukemia, colorectal carcinoma, esophageal cancer, gallbladder cancer, gastric cancer, hepatocellular cancer, non-Hodgkin lymphoma, non-small cell lung cancer, ovarian cancer, pancreatic cancer, prostate cancer, renal cell cancer, small cell lung cancer, urinary bladder cancer and uterine cancer.

The present invention further relates to particular marker proteins and biomarkers based on the peptides according to the present invention, herein called "targets" that can be used in the diagnosis and/or prognosis of melanoma. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a melanoma marker (poly)peptide, delivery of a toxin to a melanoma cell expressing a cancer marker gene at an increased level, and/or inhibiting the activity of a melanoma marker polypeptide) according to the invention.

Whenever possible, the antibodies of the invention may be purchased from commercial sources. The antibodies of the invention may also be generated using well-known methods. The skilled artisan will understand that either full length melanoma marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 237 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the melanoma marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating melanoma, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occur in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably, the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 237, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively eliciting high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore, such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, and vaccinia-infected target cells. In addition, plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 237.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual"

the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to levels of expression in normal tissues or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore, any molecule of the present invention may be used as medicament or in the manufacture of a medicament. The molecule may be used by itself or combined with other molecule(s) of the invention or (a) known molecule(s).

The present invention is further directed at a kit comprising:

(a) a container containing a pharmaceutical composition as described above, in solution or in lyophilized form;

(b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 μg) and preferably not more than 3 mg/mL/peptide (=1500 μg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably, the administration is s.c., and most preferably i.d. administration may be by infusion pump.

Since the peptides of the invention were isolated from melanoma, the medicament of the invention is preferably used to treat melanoma.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of melanoma patients with various HLA-A HLA-B and HLA-C alleles. It may contain MHC class I and MHC class II peptides or elongated MHC class I peptides. In addition to the tumor associated peptides collected from several melanoma tissues, the warehouse may contain HLA-A*02 and HLA-A*24 marker peptides. These peptides allow comparison of the magnitude of T-cell immunity induced by TUMAPS in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, melanoma samples from patients and blood from healthy donors were analyzed in a stepwise approach:

1. HLA ligands from the malignant material were identified by mass spectrometry
2. Genome-wide messenger ribonucleic acid (mRNA) expression analysis was used to identify genes over-expressed in the malignant tissue (melanoma) compared with a range of normal organs and tissues
3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues.
6. In order to assess, whether an induction of in vivo T-cell responses by the selected peptides may be feasible, in vitro immunogenicity assays were performed using human T cells from healthy donors as well as from melanoma patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients' tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germline variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from melanoma cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for melanoma. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immunosurveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

BRIEF DESCRIPTION OF THE DRAWINGS

The present invention will now be described in the following examples which describe preferred embodiments thereof, and with reference to the accompanying figures, nevertheless, without being limited thereto. For the purposes of the present invention, all references as cited herein are incorporated by reference in their entireties.

FIGS. 1A through 1J show the over-presentation of various peptides in normal tissues (white bars) and melanoma (black bars). FIG. 1A) Gene symbol: S100A1, Peptide: FLDVKELML (SEQ ID NO.: 1), Tissues from left to right: 4 adipose tissues, 5 adrenal glands, 24 blood cells, 15 blood vessels, 10 bone marrows, 14 brains, 7 breasts, 7 esophagi, 2 eyes, 3 gallbladders, 16 hearts, 17 kidneys, 20 large intestines, 23 livers, 49 lungs, 7 lymph nodes, 12 nerves, 2 ovaries, 8 pancreases, 6 parathyroid glands, 1 peritoneum, 5 pituitary glands, 7 placentas, 1 pleura, 3 prostates, 7 salivary glands, 5 skeletal muscles, 3 small intestines, 12 spleens, 5 stomachs, 5 testes, 2 thymi, 2 thyroid glands, 11 tracheas, 7 ureters, 8 urinary bladders, 6 uteri, 12 skins, 18 melanoma. FIG. 1B) Gene symbol: EXTL1, Peptide: VLFKDPVSV (SEQ ID NO.:3), Tissues from left to right: 4 adipose tissues, 5 adrenal glands, 24 blood cells, 15 blood vessels, 10 bone marrows, 14 brains, 7 breasts, 7 esophagi, 2 eyes, 3 gallbladders, 16 hearts, 17 kidneys, 20 large intestines, 23 livers, 49 lungs, 7 lymph nodes, 12 nerves, 2 ovaries, 8 pancreases, 6 parathyroid glands, 1 peritoneum, 5 pituitary glands, 7 placentas, 1 pleura, 3 prostates, 7 salivary glands, 5 skeletal muscles, 3 small intestines, 12 spleens, 5 stomachs, 5 testes, 2 thymi, 2 thyroid glands, 11 tracheas, 7 ureters, 8 urinary bladders, 6 uteri, 12 skins, 18 melanoma. FIG. 1C) Gene symbol: HMCN1, Peptide: IQSETTVTV (SEQ ID NO.: 13), Tissues from left to right: 4 adipose tissues, 5 adrenal glands, 24 blood cells, 15 blood vessels, 10 bone marrows, 14 brains, 7 breasts, 7 esophagi, 2 eyes, 3 gallbladders, 16 hearts, 17 kidneys, 20 large intestines, 23 livers, 49 lungs, 7 lymph nodes, 12 nerves, 2 ovaries, 8 pancreases, 6 parathyroid glands, 1 peritoneum, 5 pituitary glands, 7 placentas, 1 pleura, 3 prostates, 7 salivary glands, 5 skeletal muscles, 3 small intestines, 12 spleens, 5 stomachs, 5 testes, 2 thymi, 2 thyroid glands, 11 tracheas, 7 ureters, 8 urinary bladders, 6 uteri, 12 skins, 18 melanoma. FIG. 1D) Gene symbol: TMEM17, Peptide: NLQEKVPEL (SEQ ID NO.: 7), Samples from left to right: 14 cancer tissues (1 brain cancer, 1 breast cancer, 1 head-and-neck cancer, 3 lung cancers, 1 myeloid cells cancer, 1 ovarian cancer, 1 pancreas cancer, 4 melanomas, 1 uterus cancer). FIG. 1E) through 1J) show the over-presentation of various peptides in different cancer tissues (black dots). Upper part: Median MS signal intensities from technical replicate measurements are plotted as dots for single HLA-A*02 positive normal (grey dots) and tumor samples (black dots) on which the peptide was detected. Tumor and normal samples are grouped according to organ of origin, and box-and-whisker plots represent median, 25th and 75th percentile (box), and minimum and maximum (whiskers) of normalized signal intensities over multiple samples. Normal organs are ordered according to risk categories (blood cells, blood vessels, brain, liver, lung: high risk, grey dots; reproductive organs, breast, prostate: low risk, grey dots; all other organs: medium risk; grey dots). Lower part: The relative peptide detection frequency in every organ is shown as spine plot. Numbers below the panel indicate number of samples on which the peptide was detected out of the total number of samples analyzed for each organ (N=526 for normal samples, N=562 for tumor samples). If the peptide has been detected on a sample but could not be quantified for technical reasons, the sample is included in this representation of detection frequency, but no dot is shown in the upper part of the figure. Tissues (from left to right): Normal samples: blood cells; bloodvess (blood vessels); brain; heart; liver; lung; adipose (adipose tissue); adren.gl. (adrenal gland); bile duct; bladder; BM (bone marrow); cartilage; esoph (esophagus); eye; gallb (gallbladder); head & neck; kidney; large_int (large intestine); LN (lymph node); nerve; pancreas; parathyr (parathyroid gland); perit (peritoneum); pituit (pituitary); pleura; skel.mus (skeletal muscle); skin; small_int (small intestine); spleen; stomach; thyroid; trachea; ureter; breast; ovary; placenta; prostate; testis; thymus; uterus. Tumor samples: AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; GEJC: stomach cardia esophagus, cancer; HCC: hepatocellular carcinoma; HNSCC: head-and-neck cancer; MEL: melanoma; NHL: non-hodgkin lymphoma; NSCLC: non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer. FIG. 1E) Gene symbols: HLA-B, HLA-C, Peptide: VLAVLGAVVAV (SEQ ID NO.: 19), FIG. 1F) Gene symbol: PARVA, Peptide: SLVAILHLL (SEQ ID NO.: 24), FIG. 1G) Gene symbol: METAP2, Peptide: TMIEICEKL (SEQ ID NO.: 118), FIG. 1H) Gene symbol: UTP20, Peptide: QLMEGKVVL (SEQ ID NO.: 120), FIG. 1I) Gene symbol: SNRPN, Peptide: FLGEPASYLYL (SEQ ID NO.: 151), FIG. 1J) Gene symbol: IPO9, Peptide: SILDGLIHL (SEQ ID NO.: 209).

FIGS. 2A through 2C) show exemplary expression profiles of source genes of the present invention that are highly over-expressed or exclusively expressed in melanoma in a panel of normal tissues (white bars) and 10 melanoma samples (black bars). Tissues from left to right: 6 arteries, 2 blood cells, 2 brains, 1 heart, 2 livers, 3 lungs, 2 veins, 1 adipose tissue, 1 adrenal gland, 5 bone marrows, 1 cartilage, 1 colon, 1 esophagus, 2 eyes, 2 gallbladders, 2 head-and-neck and salivary glands, 1 kidney, 6 lymph nodes, 4 pancreases, 2 peripheral nerves, 2 pituitary glands, 1 rectum, 2 skeletal muscles, 1 skin, 1 small intestine, 1 spleen, 1 stomach, 1 thyroid gland, 7 tracheas, 1 urinary bladder, 1 breast, 5 ovaries, 5 placentas, 1 prostate, 1 testis, 1 thymus, 1 uterus, 10 melanoma. FIG. 2A) Gene symbol: SLC24A5, FIG. 2B) Gene symbol: SLC45A2, FIG. 2C) Gene symbol: FMN1.

EXAMPLES

Example 1

Figure 1A:
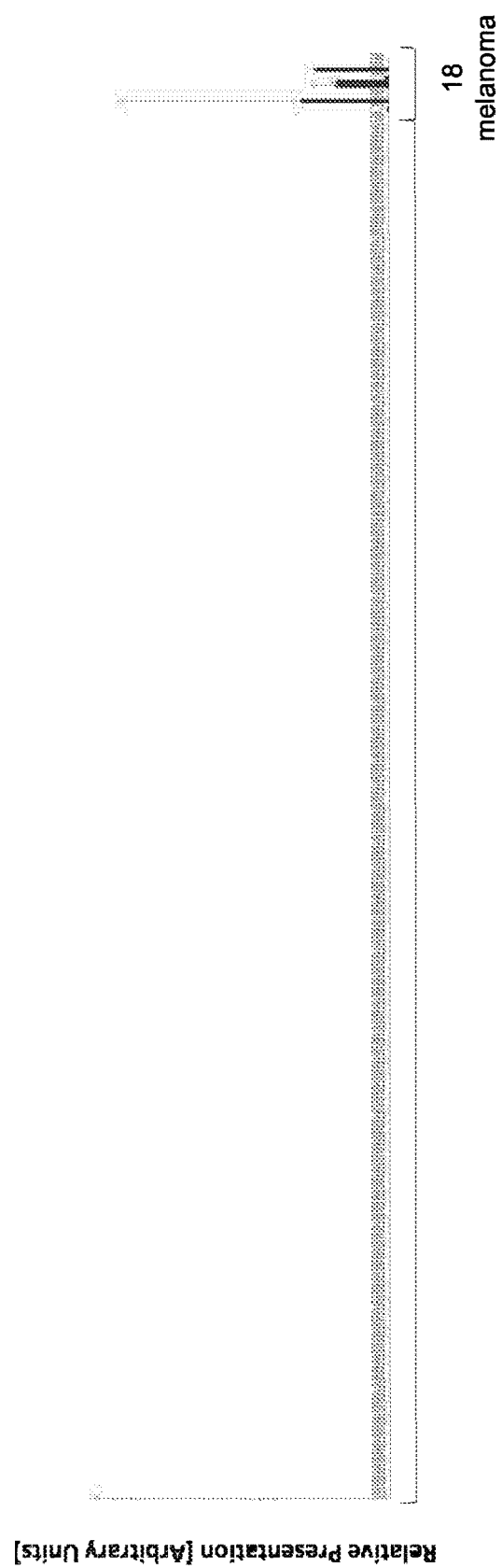
Figure 1B:
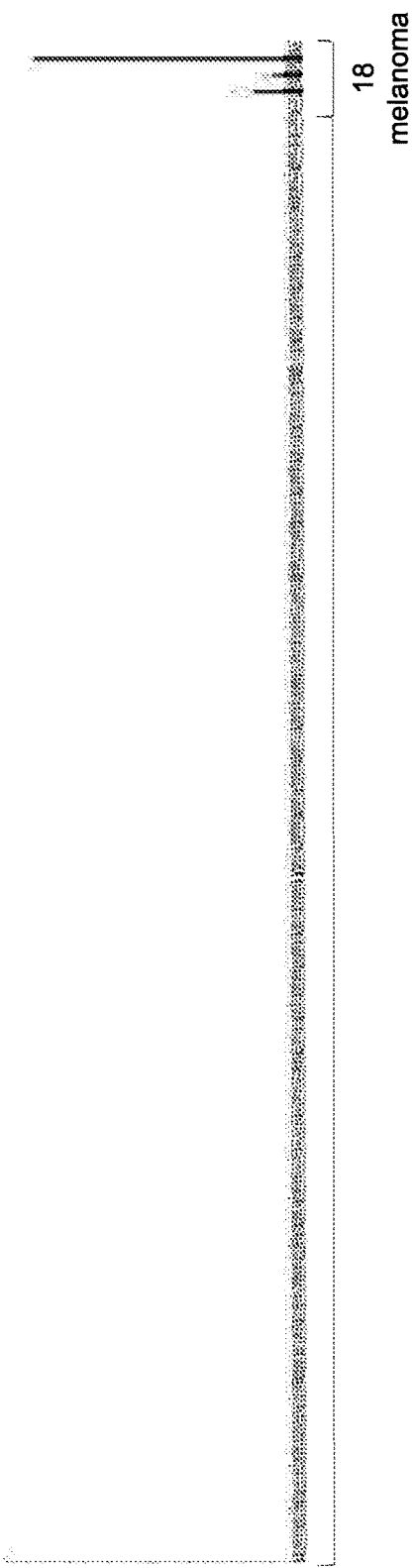
Figure 1D:
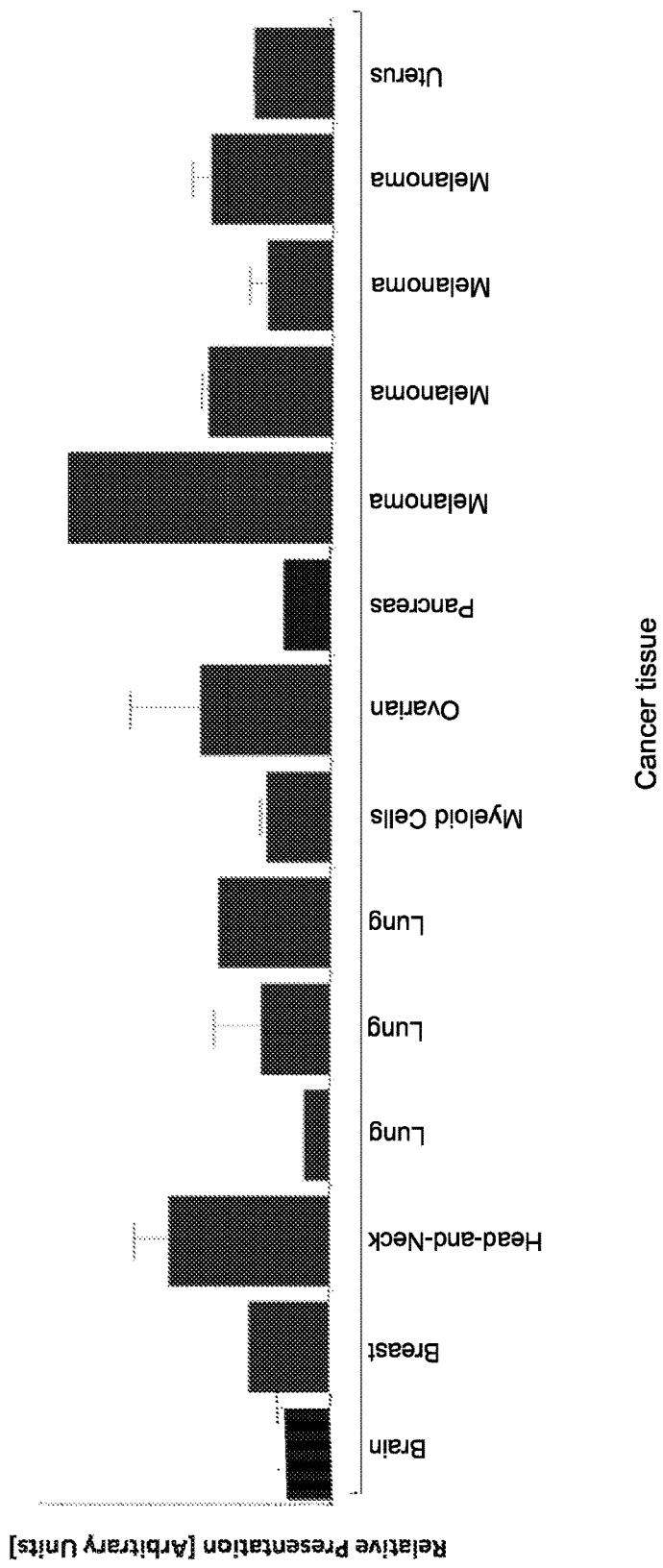
Figure 1E:
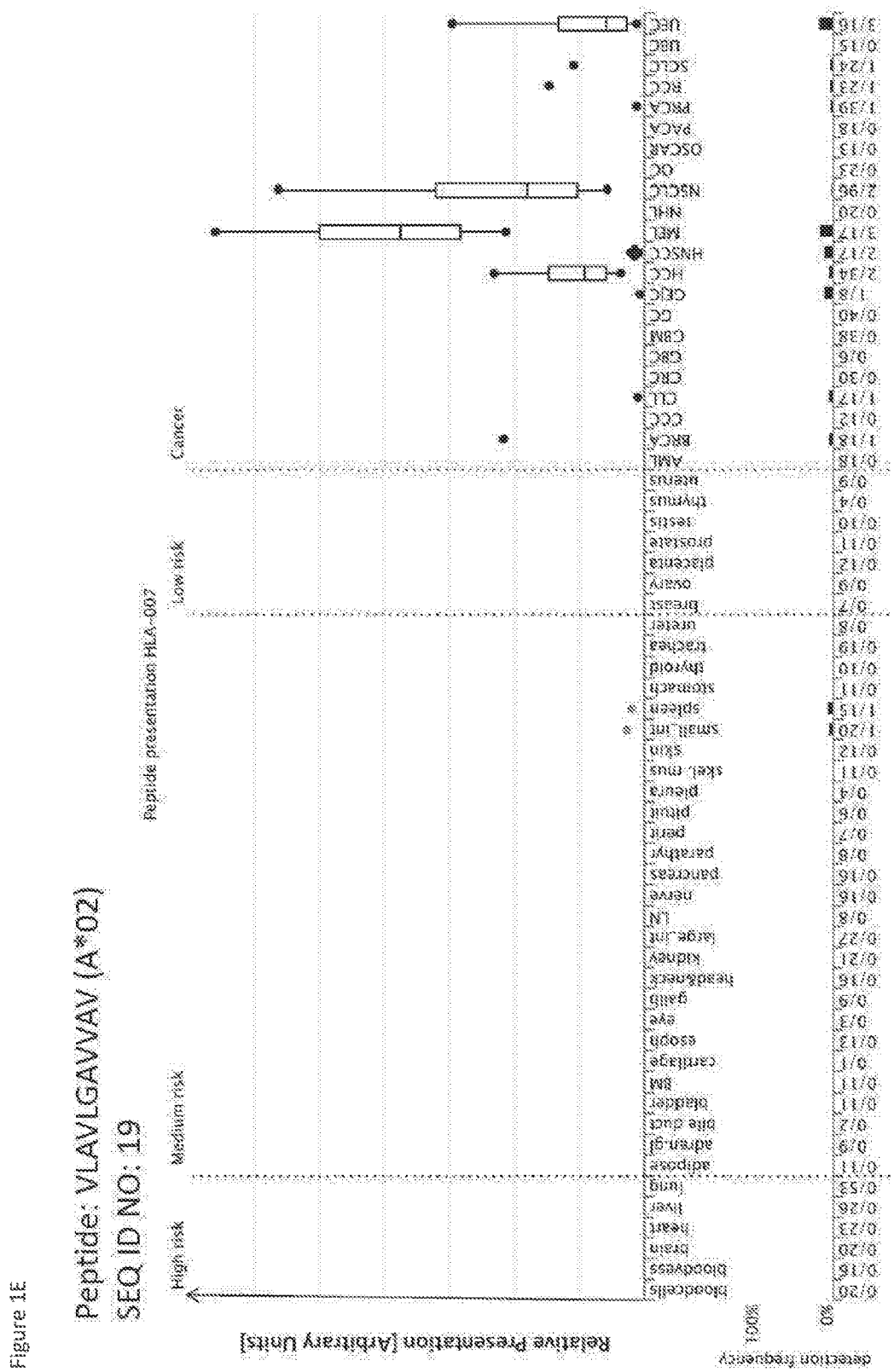
Figure 1F:
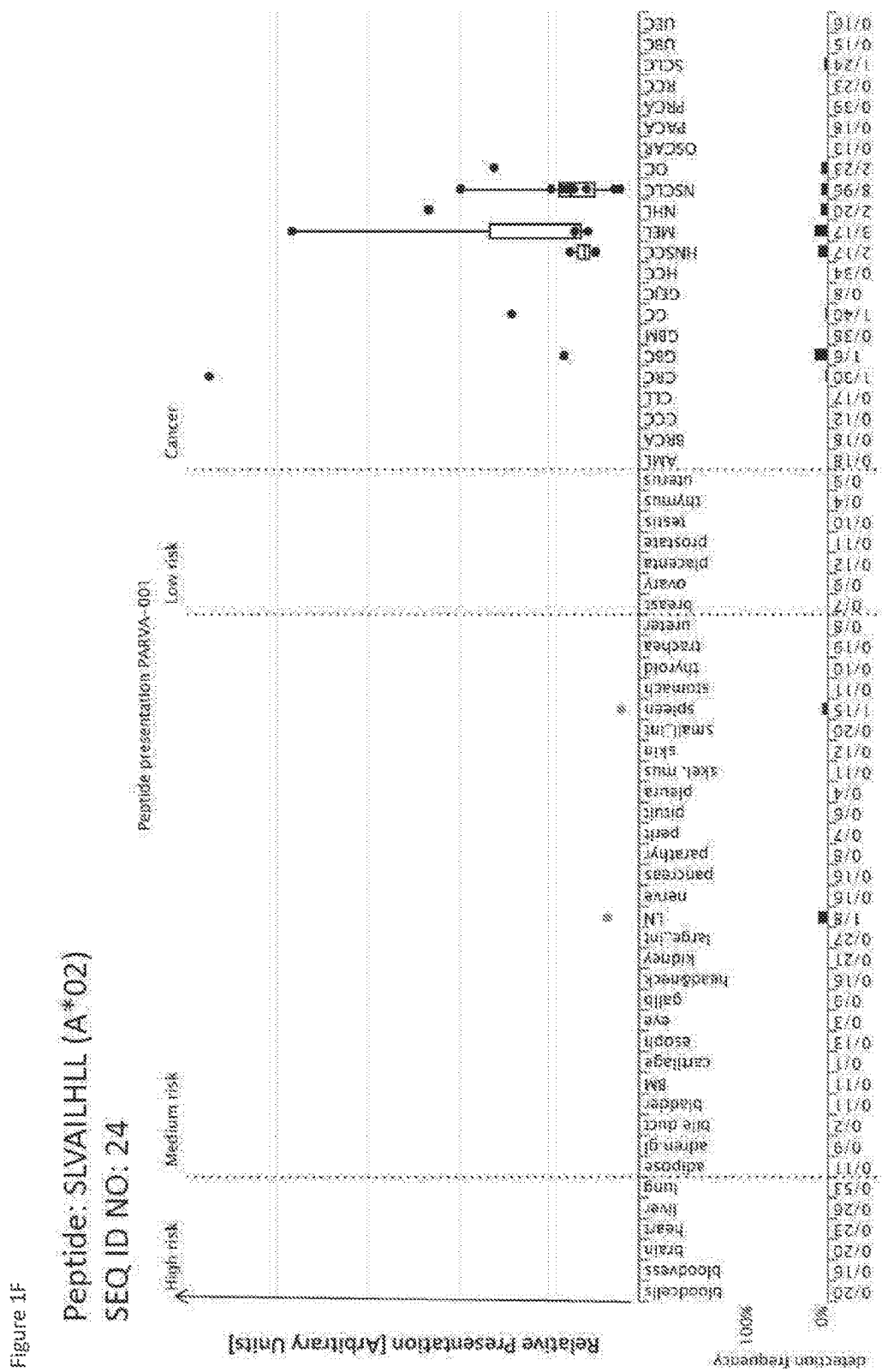
Figure 1G:
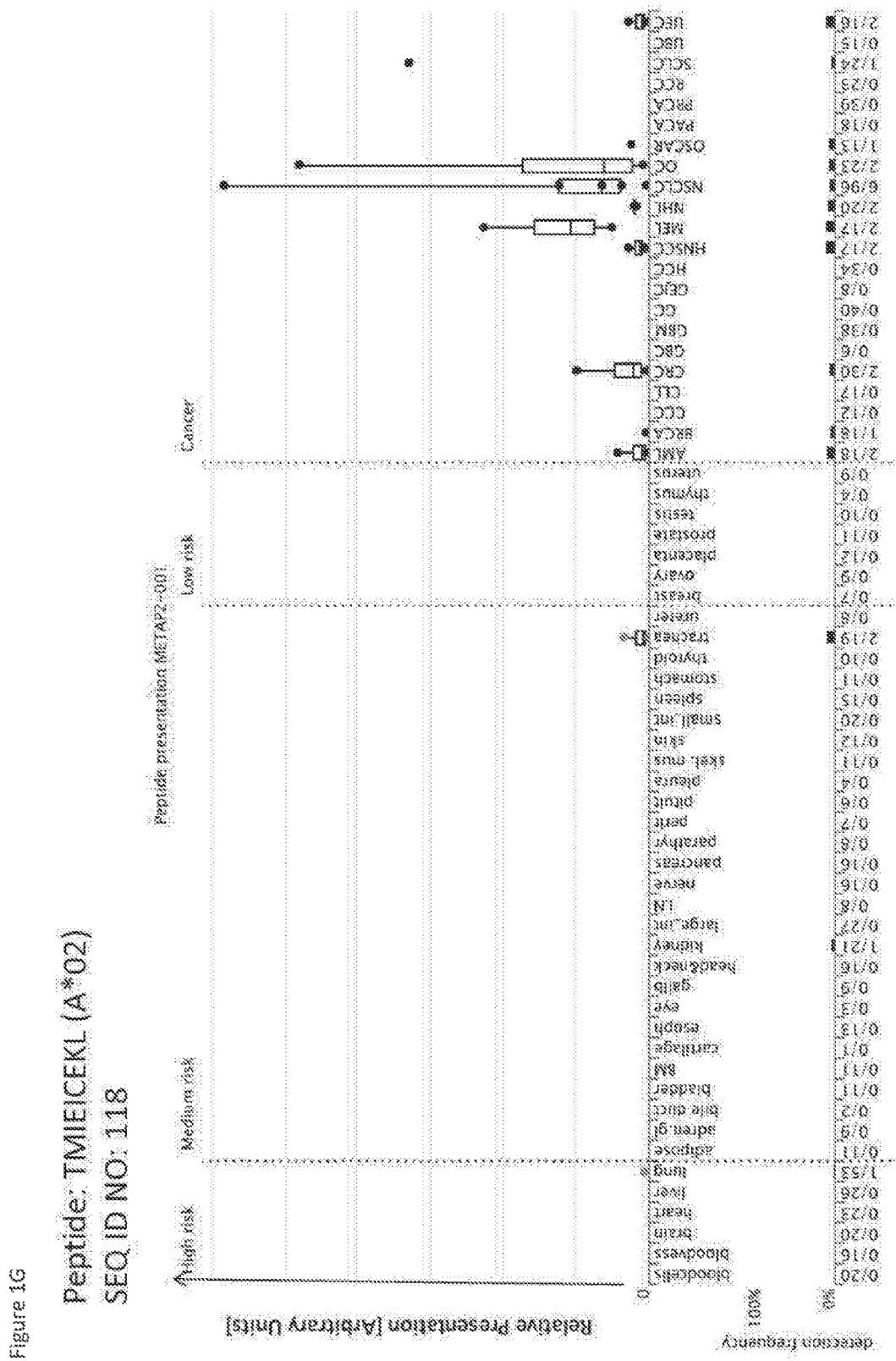
Figure 1H:
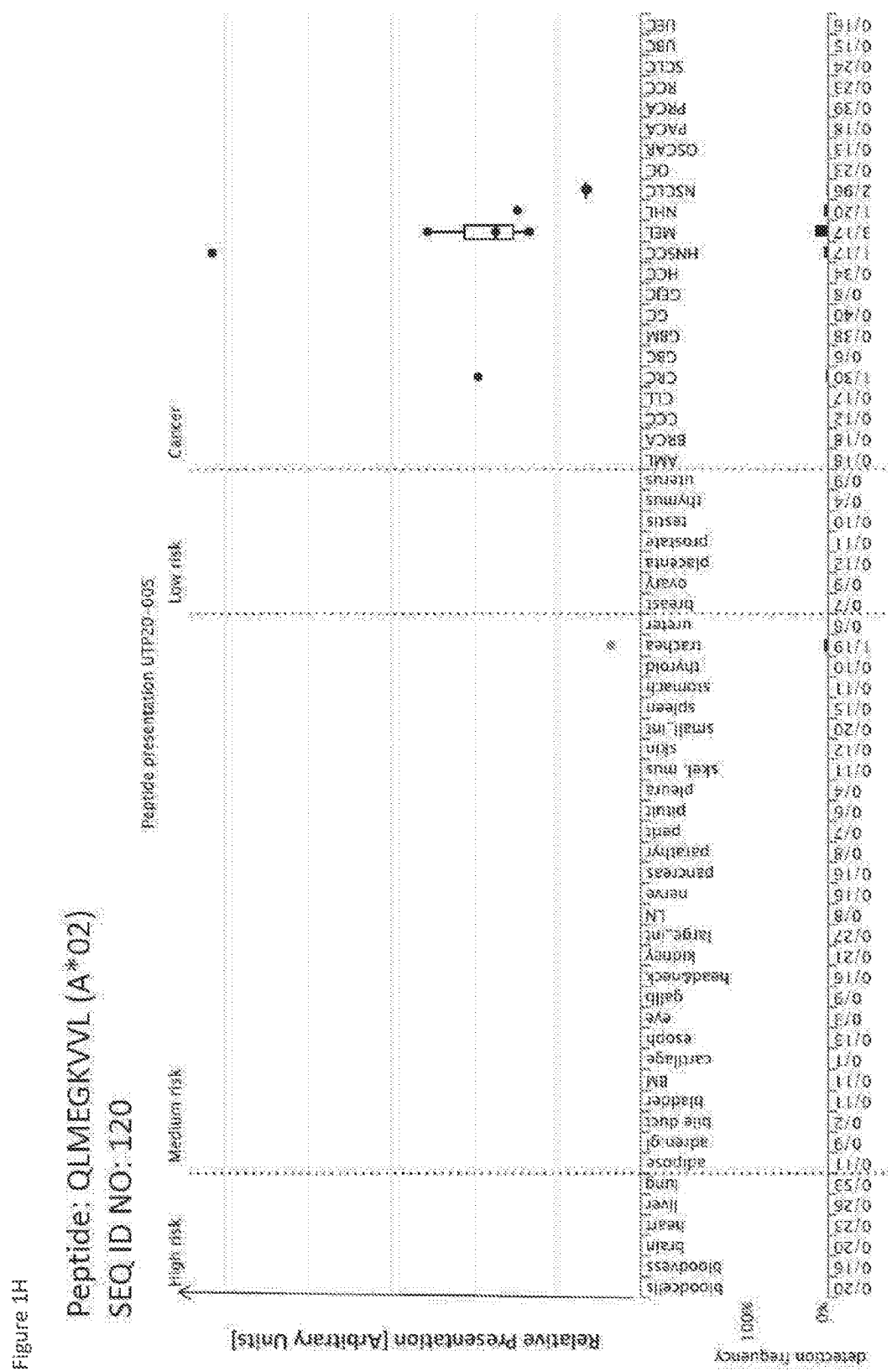
Figure 11:
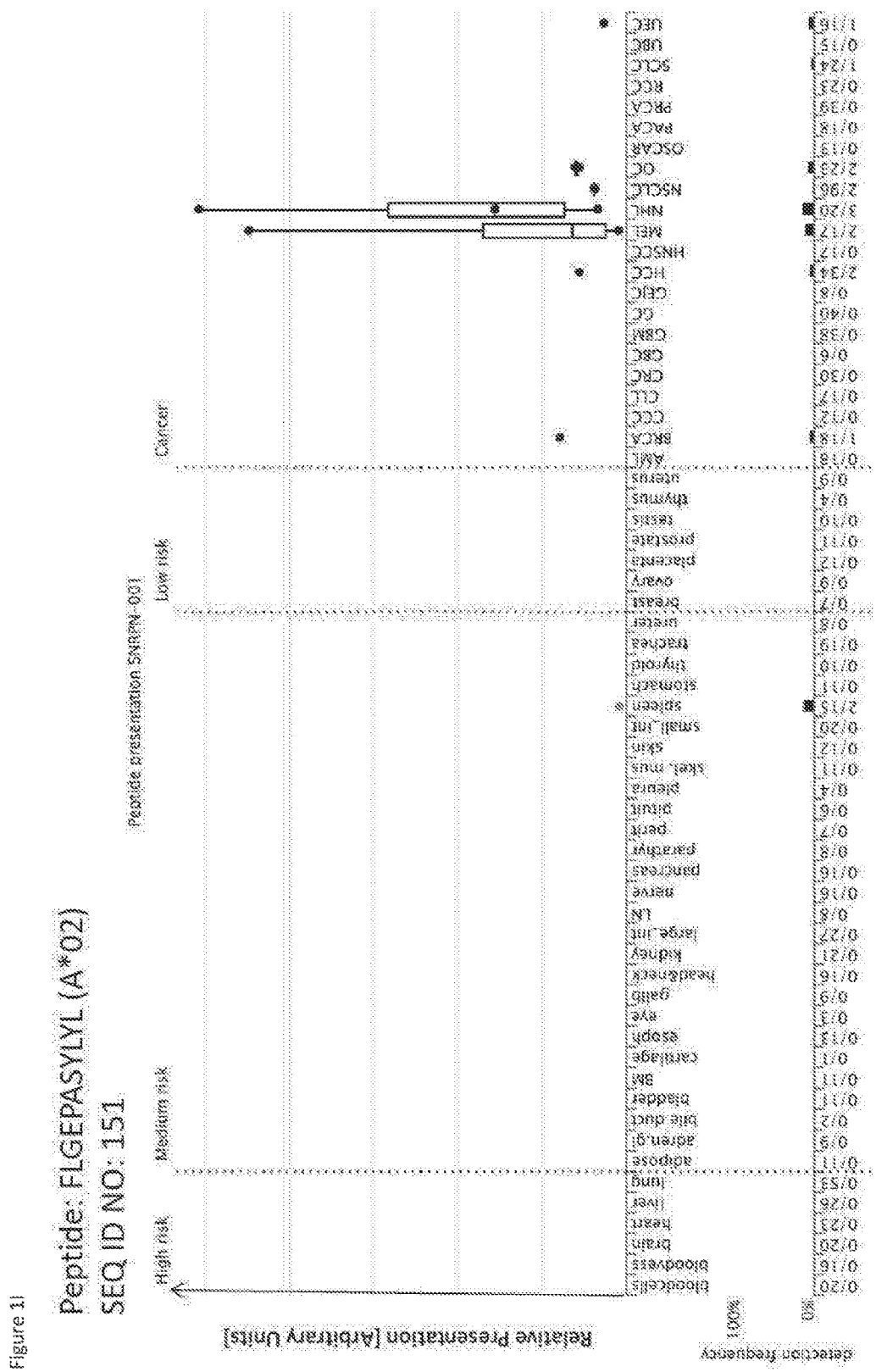
Figure 1J:
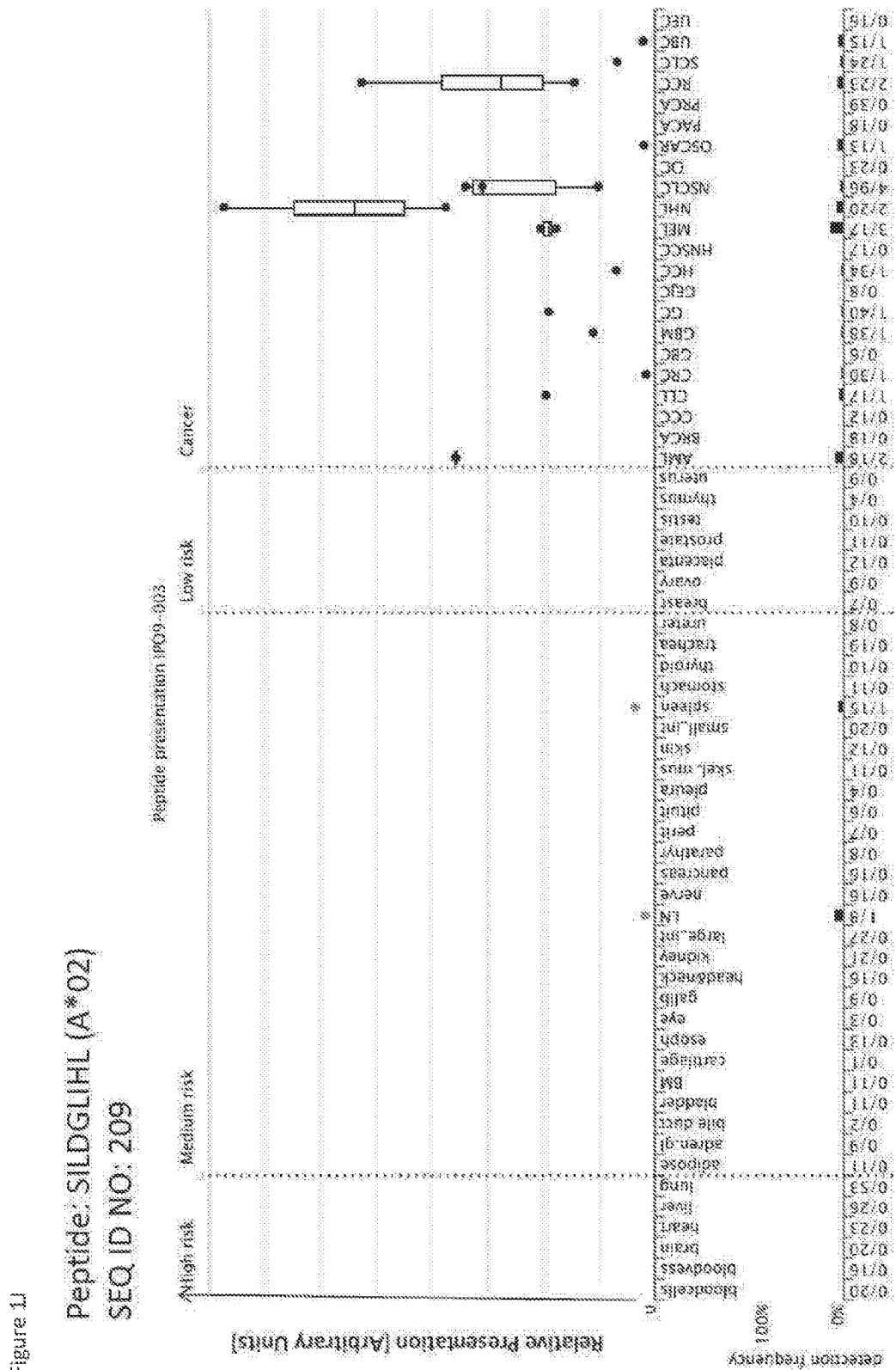

Identification and Quantitation of Tumor Associated Peptides Presented on the Cell Surface Tissue Samples Patients' tumor tissues were obtained from: Asterand (Detroit, Mich., USA & Royston, Herts, UK); ProteoGenex Inc. (Culver City, Calif., USA), Tissue Solutions Ltd (Glasgow, UK); University Hospital Heidelberg (Heidelberg, Germany); and University Hospital Tübingen (Tübingen, Germany).

Normal tissues were obtained from Asterand (Detroit, Mich., USA & Royston, Herts, UK); Bio-Options Inc. (Brea, Calif., USA); BioServe (Beltsville, Md., USA); Capital BioScience Inc. (Rockville, Md., USA); Geneticist Inc. (Glendale, Calif., USA); Kyoto Prefectural University of Medicine (KPUM) (Kyoto, Japan); ProteoGenex Inc. (Culver City, Calif., USA); Tissue Solutions Ltd (Glasgow, UK); University Hospital Geneva (Geneva, Switzerland); University Hospital Heidelberg (Heidelberg, Germany); University Hospital Munich (Munich, Germany); and University Hospital Tübingen (Tübingen, Germany).

Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, -B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 µm i.d.× 250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the Orbitrap (R=30 000), which was followed by MS/MS scans also in the Orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose melanoma samples to a baseline of normal tissue samples. Presentation profiles of exemplary over-presented peptides are shown in FIGS. 1A-1J. Presentation scores for exemplary peptides are shown in Table 8.

TABLE 8

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues considered relevant for comparison with tumors consisted of: adipose tissue, adrenal gland, blood cells, blood vessel, bone marrow, brain, esophagus, eye, gallbladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Peptide Presentation |
|---|---|---|
| 1 | FLDVKELML | +++ |
| 2 | VLLGENVEL | +++ |
| 3 | VLFKDPVSV | +++ |
| 4 | KTWDQVPFSV | +++ |
| 5 | ILDEGHILQL | +++ |
| 6 | SIPDTIASV | +++ |
| 7 | NLQEKVPEL | +++ |
| 8 | SIIPYLLEA | +++ |
| 9 | SLAGLVLYV | +++ |
| 10 | KMTQYITEL | +++ |
| 11 | TLIELLLPKL | +++ |
| 12 | RLDDKTTNV | ++ |
| 13 | IQSETTVTV | ++ |
| 14 | VLYEMLYGL | +++ |
| 17 | GVVHGVATV | ++ |
| 18 | SLADVVDTL | + |
| 19 | VLAVLGAVVAV | +++ |
| 20 | VISPHGIASV | +++ |
| 21 | FMYNFQLVTL | ++ |
| 22 | KLLELQELVL | ++ |
| 24 | SLVAILHLL | ++ |
| 26 | KIEDLIKYL | +++ |
| 27 | TLWYVPLSL | ++ |
| 28 | IVDNTTMQL | + |
| 30 | VLFPMDLAL | +++ |
| 31 | FLPRKFPSL | ++ |
| 32 | GLDIITNKV | ++ |
| 33 | SLYSYFQKV | +++ |
| 34 | YLINFEIRSL | +++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues considered relevant for comparison with tumors consisted of: adipose tissue, adrenal gland, blood cells, blood vessel, bone marrow, brain, esophagus, eye, gall-bladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Peptide Presentation |
|---|---|---|
| 35 | ALFAAGANV | +++ |
| 36 | SVNGFISTL | +++ |
| 37 | TLKEYLESL | +++ |
| 38 | KLGFGTGVNVYL | +++ |
| 39 | ALPPPPASI | +++ |
| 40 | LLSNTVSTL | +++ |
| 41 | LLDDPTNAHFI | +++ |
| 42 | VLKADVVLL | +++ |
| 43 | LLPDPLYSL | +++ |
| 44 | FLYTYIAKV | +++ |
| 45 | FVYGEPREL | +++ |
| 46 | VMSSTLYTV | +++ |
| 47 | ALDSDPVGL | +++ |
| 48 | HLIGWTAFL | +++ |
| 49 | ALLSQDFEL | +++ |
| 50 | HLDQIFQNL | +++ |
| 51 | LIDKIIEYL | +++ |
| 52 | NLDYAILKL | +++ |
| 53 | ILDEEKFNV | +++ |
| 54 | LLDSGAFHL | +++ |
| 55 | NLDKLYHGL | +++ |
| 56 | ILDELVKSL | +++ |
| 57 | GILSFLPVL | +++ |
| 58 | ILGDWSIQV | +++ |
| 59 | IIDDVMKEL | ++ |
| 60 | ILPEAQDYFL | +++ |
| 61 | KLSVHVTAL | +++ |
| 62 | LLDTTQKYL | +++ |
| 63 | SIDDSDPIV | +++ |
| 64 | SLGPIMLTKI | +++ |
| 65 | TTLGGFAKV | +++ |
| 66 | VMFEYGMRL | +++ |
| 67 | YVDSEGIVRM | +++ |
| 68 | FLAEAARSL | +++ |
| 69 | IIDDKPIGL | +++ |
| 70 | LIDEAAQML | +++ |
| 71 | SLDEVAVSL | +++ |
| 72 | TLLEVDAIVNA | +++ |
| 73 | ELDKIYETL | +++ |
| 74 | GTIPLIESL | +++ |
| 75 | FMYAGQLTL | +++ |
| 76 | QIDSIHLLL | +++ |
| 77 | SIDDVVKKL | +++ |
| 78 | ALKDLVNLI | +++ |
| 79 | AVDNILLKL | +++ |
| 80 | FADELSHLL | +++ |
| 81 | FLDDGNQML | +++ |
| 82 | GIDDLHISL | +++ |
| 83 | GLDKVITVL | +++ |
| 84 | GLDTILQNL | +++ |
| 86 | HTLPHEIVVNL | +++ |
| 87 | IIDPPLHGQLL | +++ |
| 88 | ILDGIIREL | ++ |
| 89 | ILDNSPAFL | +++ |
| 90 | ILDYIHNGL | +++ |
| 91 | ILLDRLFSV | +++ |
| 92 | KLPGFPTQDDEV | +++ |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues considered relevant for comparison with tumors consisted of: adipose tissue, adrenal gland, blood cells, blood vessel, bone marrow, brain, esophagus, eye, gall-bladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Peptide Presentation |
|---|---|---|
| 93 | LLAKAVQNV | +++ |
| 94 | LLDAFSIKL | +++ |
| 95 | LLDALQHEL | +++ |
| 96 | LLDMSLVKL | +++ |
| 97 | NLDATVTAL | +++ |
| 98 | NLPNTNSILGV | +++ |
| 99 | NLPSELPQL | +++ |
| 100 | NLREILQNV | +++ |
| 101 | NVDENVAEL | +++ |
| 102 | RLPDQFSKL | +++ |
| 103 | SLDAVMPHL | +++ |
| 104 | SLDQIIQHL | +++ |
| 105 | SLKQTVVTL | +++ |
| 106 | TLSEICEFI | +++ |
| 107 | TLVAFLQQV | +++ |
| 108 | TVIRPLPGL | +++ |
| 109 | VIDDLIQKL | +++ |
| 110 | VLDTLTKVL | +++ |
| 111 | VLDVSFNRL | +++ |
| 112 | VLPAVLTRL | +++ |
| 113 | VLYSLVSKI | +++ |
| 114 | VVDDIVSKL | +++ |
| 115 | YIDDVFMGL | +++ |
| 116 | LMDETMKEL | ++ |
| 117 | KQQASQVLV | ++ |
| 118 | TMIEICEKL | ++ |
| 119 | SLGLGFISRV | ++ |
| 120 | QLMEGKVVL | ++ |
| 121 | FLEDLVPYL | + |
| 122 | YVDDFGVSV | ++ |
| 125 | YLFAFLNHL | +++ |
| 126 | SLIDFVVTC | + |
| 127 | TLISDIEAVKA | +++ |
| 129 | VLPDDLSGV | + |
| 130 | GLVDVLYTA | + |
| 131 | FVDPNGKISL | ++ |
| 132 | FLDASGAKL | + |
| 133 | ALDPAYTTL | ++ |
| 134 | LLDEVLHTM | +++ |
| 135 | FLDDQETRL | + |
| 136 | FAYDGKDYIAL | ++ |
| 137 | ILPSNLLTV | + |
| 138 | YLDKTFYNL | + |
| 139 | AVDATVNQV | + |
| 140 | RLEAYLARV | + |
| 146 | GVGPVPARA | + |
| 149 | YLDTFALKL | + |
| 155 | GLAGFFASV | ++ |
| 156 | ALMDTDGSGKLNL | + |
| 157 | HLFETISQA | ++ |
| 159 | TILATVPLV | ++ |
| 160 | ALDDISESI | + |
| 163 | RLMANPEALKI | ++ |
| 164 | ALFFQLVDV | ++ |
| 165 | ALIEVLQPLI | ++ |
| 166 | SIIPPLFTV | ++ |
| 168 | KLLAATLLL | + |

TABLE 8-continued

Presentation scores. The table lists peptides that are very highly over-presented on tumors compared to a panel of normal tissues (+++), highly over-presented on tumors compared to a panel of normal tissues (++) or over-presented on tumors compared to a panel of normal tissues (+). The panel of normal tissues considered relevant for comparison with tumors consisted of: adipose tissue, adrenal gland, blood cells, blood vessel, bone marrow, brain, esophagus, eye, gall-bladder, heart, kidney, large intestine, liver, lung, lymph node, nerve, pancreas, parathyroid gland, peritoneum, pituitary, pleura, salivary gland, skeletal muscle, skin, small intestine, spleen, stomach, thymus, thyroid gland, trachea, ureter, urinary bladder.

| SEQ ID No | Sequence | Peptide Presentation |
|---|---|---|
| 169 | TLLESIQHV | + |
| 170 | KLKEAVEAI | ++ |
| 171 | KVSGVILSV | ++ |
| 172 | FLPAGIVAV | ++ |
| 173 | ALDDIIYRA | + |
| 175 | VLDSVDVRL | + |
| 177 | ILWDTLLRL | + |
| 178 | FAYDGKDYIA | +++ |
| 179 | ALDDTVLQV | + |
| 180 | KLAEALYIA | + |
| 181 | GLIDLEANYL | + |
| 182 | SVALVIHNV | + |
| 184 | VLFSSPPVILL | + |
| 187 | SLPRPTPQA | + |
| 188 | VVVDPIQSV | +++ |
| 189 | KALQFLEEV | +++ |
| 190 | RLVSLITLL | +++ |
| 191 | YLDKMNNNI | +++ |
| 192 | KLFTQIFGV | +++ |
| 193 | ALDEPTTNL | ++ |
| 194 | TLDDIMAAV | ++ |
| 195 | IAAGIFNDL | +++ |
| 196 | ALEPIDITV | +++ |
| 197 | ALDSGFNSV | + |
| 198 | EVVDKINQV | +++ |
| 200 | LLEEINHFL | +++ |
| 201 | SLIDRTIKM | +++ |
| 202 | RVAFKINSV | +++ |
| 203 | FLNEDISKL | +++ |
| 204 | RMDEEFTKI | +++ |
| 205 | SLKSKVLSV | +++ |
| 206 | LLYEDIPDKV | + |
| 207 | VQIGDIVTV | + |
| 208 | YSDDIPHAL | ++ |
| 209 | SILDGLIHL | ++ |
| 211 | FLPFLTTEV | + |
| 212 | LLKDSIVQL | + |
| 213 | LLDPTNVFI | + |
| 214 | VLMEMSYRL | + |
| 215 | EVISKLYAV | + |
| 216 | TLLHFLAEL | ++ |
| 217 | NMMSGISSV | ++ |
| 218 | STLHLVLRL | + |
| 221 | SLLPTEQPRL | ++ |
| 223 | FLETNVPLL | + |
| 224 | ILDEPTNHL | + |
| 225 | VLFGAVITGA | + |
| 226 | VLNEYFHNV | + |
| 227 | FLLEQEKTQAL | + |
| 228 | FLNLFNHTL | + |
| 229 | LLEPFVHQV | ++ |
| 230 | HLDEARTLL | + |
| 231 | KMVGDVTGA | + |
| 233 | QLYNQIIKL | + |
| 235 | ALADLQEAV | ++ |

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues for RNASeq experiments was obtained from: Asterand (Detroit, Mich., USA & Royston, Herts, UK); BioCat GmbH (Heidelberg, Germany); BioServe (Beltsville, Md., USA), Capital BioScience Inc. (Rockville, Md., USA); Geneticist Inc. (Glendale, Calif., USA), Istituto Nazionale Tumori "Pascale" (Naples, Italy); ProteoGenex Inc. (Culver City, Calif., USA), and University Hospital Heidelberg (Heidelberg, Germany).

Total RNA from tumor tissues for RNASeq experiments was obtained from: Asterand (Detroit, Mich., USA & Royston, Herts, UK); ProteoGenex Inc. (Culver City, Calif., USA); Tissue Solutions Ltd (Glasgow, UK), and University Hospital Tübingen (Tübingen, Germany).

Quality and quantity of all RNA samples were assessed on an Agilent 2100 Bioanalyzer (Agilent, Waldbronn, Germany) using the RNA 6000 Pico LabChip Kit (Agilent).

RNAseq Experiments

Gene expression analysis of—tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, Calif., USA), which includes RNA fragmentation, cDNA conversion and addition of sequencing adaptors. Libraries derived from multiple samples are mixed equimolar and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Figure 2C:
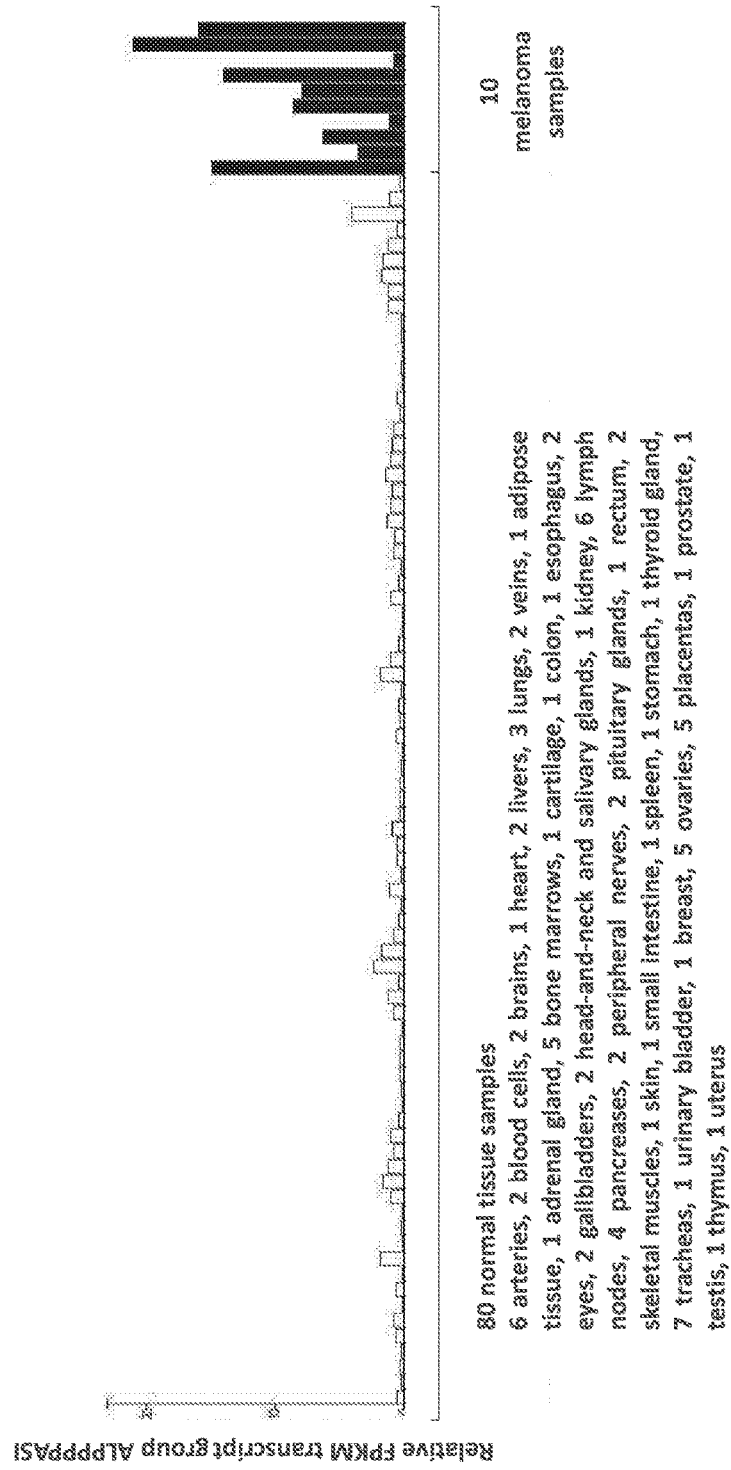

Exemplary expression profiles of source genes of the present invention that are highly over-expressed or exclusively expressed in melanoma are shown in FIGS. 2A-2C. Expression scores for further exemplary genes are shown in Table 9.

TABLE 9

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, artery, blood cells, bone marrow, brain, cartilage, colon, esophagus, eye, gallbladder, head-and-neck and salivary gland, heart, kidney, liver, lung, lymph node, pancreas, peripheral nerve, pituitary, rectum, skeletal muscle, skin, small intestine, spleen, stomach, thyroid gland, trachea, urinary bladder, and vein. In case expression data for several samples of the same tissue type were available, the arithmetic mean of all respective samples was used for the calculation.

| SEQ ID No | Sequence | Gene Expression |
|---|---|---|
| 2 | VLLGENVEL | +++ |
| 3 | VLFKDPVSV | + |
| 4 | KTWDQVPFSV | +++ |
| 5 | ILDEGHILQL | +++ |
| 6 | SIPDTIASV | +++ |
| 9 | SLAGLVLYV | +++ |
| 12 | RLDDKTTNV | ++ |
| 13 | IQSETTVTV | +++ |
| 14 | VLYEMLYGL | + |
| 18 | SLADVVDTL | + |
| 20 | VISPHGIASV | +++ |
| 25 | FIDPEQIQV | +++ |
| 33 | SLYSYFQKV | +++ |
| 35 | ALFAAGANV | +++ |
| 38 | KLGFGTGVNVYL | +++ |
| 39 | ALPPPPASI | +++ |
| 40 | LLSNTVSTL | +++ |
| 41 | LLDDPTNAHFI | +++ |
| 42 | VLKADVVLL | +++ |
| 43 | LLPDPLYSL | |
| 44 | FLYTYIAKV | +++ |
| 45 | FVYGEPREL | +++ |
| 46 | VMSSTLYTV | +++ |
| 47 | ALDSDPVGL | ++ |
| 48 | HLIGWTAFL | +++ |
| 49 | ALLSQDFEL | +++ |
| 50 | HLDQIFQNL | ++ |

TABLE 9-continued

Expression scores. The table lists peptides from genes that are very highly over-expressed in tumors compared to a panel of normal tissues (+++), highly over-expressed in tumors compared to a panel of normal tissues (++) or over-expressed in tumors compared to a panel of normal tissues (+). The baseline for this score was calculated from measurements of the following relevant normal tissues: adipose tissue, adrenal gland, artery, blood cells, bone marrow, brain, cartilage, colon, esophagus, eye, gallbladder, head-and-neck and salivary gland, heart, kidney, liver, lung, lymph node, pancreas, peripheral nerve, pituitary, rectum, skeletal muscle, skin, small intestine, spleen, stomach, thyroid gland, trachea, urinary bladder, and vein. In case expression data for several samples of the same tissue type were available, the arithmetic mean of all respective samples was used for the calculation.

| SEQ ID No | Sequence | Gene Expression |
|---|---|---|
| 52 | NLDYAILKL | ++ |
| 55 | NLDKLYHGL | + |
| 57 | GILSFLPVL | +++ |
| 58 | ILGDWSIQV | ++ |
| 61 | KLSVHVTAL | + |
| 71 | SLDEVAVSL | + |
| 125 | YLFAFLNHL | + |
| 126 | SLIDFVVTC | ++ |
| 171 | KVSGVILSV | ++ |

Example 3

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*0201 restricted TUMAPs of the invention, demonstrating that these peptides are T-cell epitopes against which CD8+ precursor T cells exist in humans (Table 10).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 339) from modified Melan-A/MART-1) and A*0201/DDX5-001 (YLLPAIVHI from DDX5, SEQ ID NO. 340), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating $1 \times 10^6$ CD8+ T cells with $2 \times 10^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oreg., USA). In vitro priming of specific multimer+ CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for Melanoma Peptides

Figure 3A:
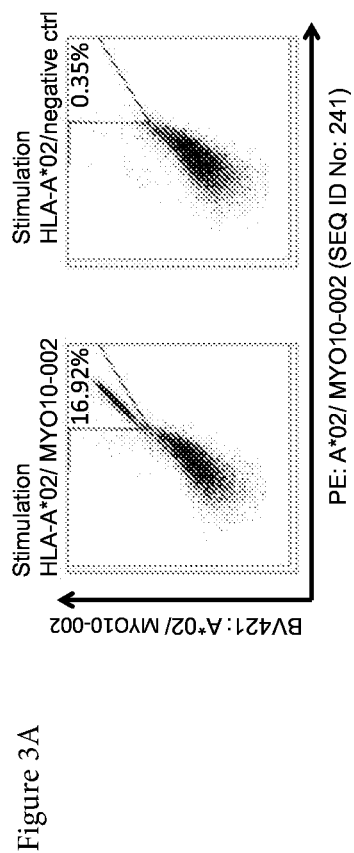
FIGS. 3A and 3B shows exemplary immunogenicity data: flow cytometry results after peptide-specific multimer staining.
Figure 3B:
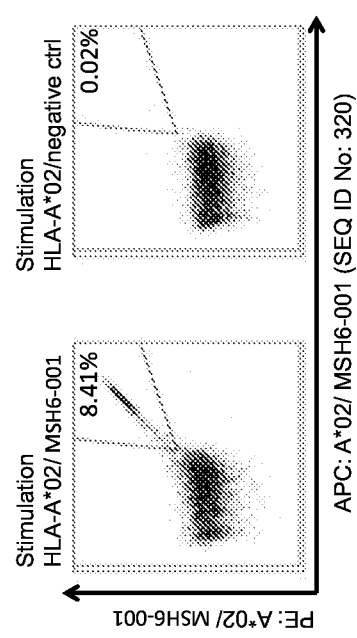
Figure 4A:
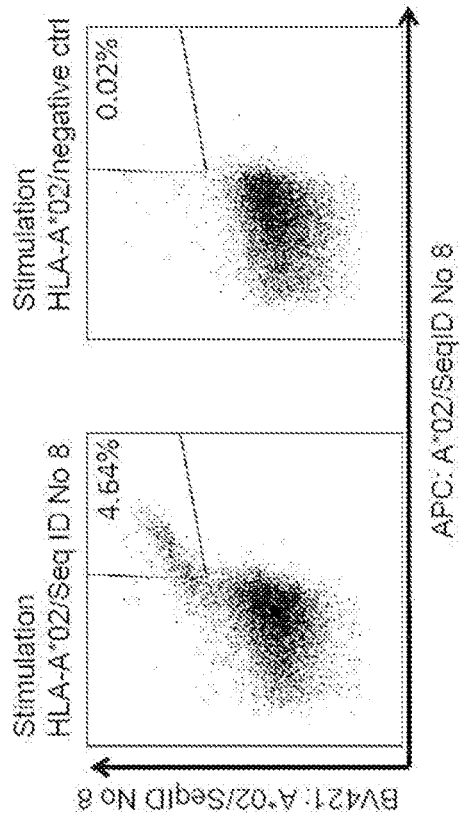
FIGS. 4A through 4C show exemplary results of peptide-specific in vitro CD8+ T cell responses of a healthy HLA-A*02+ donor. CD8+ T cells were primed using artificial APCs coated with anti-CD28 mAb and HLA-A*02 in complex with SeqID No 8 peptide (FIG. 4A, left panel), SeqID No 12 peptide (FIG. 4B, left panel) and SeqID No 155 peptide (FIG. 4C, left panel), respectively. After three cycles of stimulation, the detection of peptide-reactive cells was performed by 2D multimer staining with A*02/SeqID No 8 (FIG. 4A), A*02/SeqID No 12 (FIG. 4B) or A*02/SeqID No 155 (FIG. 4C). Right panels (FIGS. 4A, 4B and 4C) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.
Figure 4B:
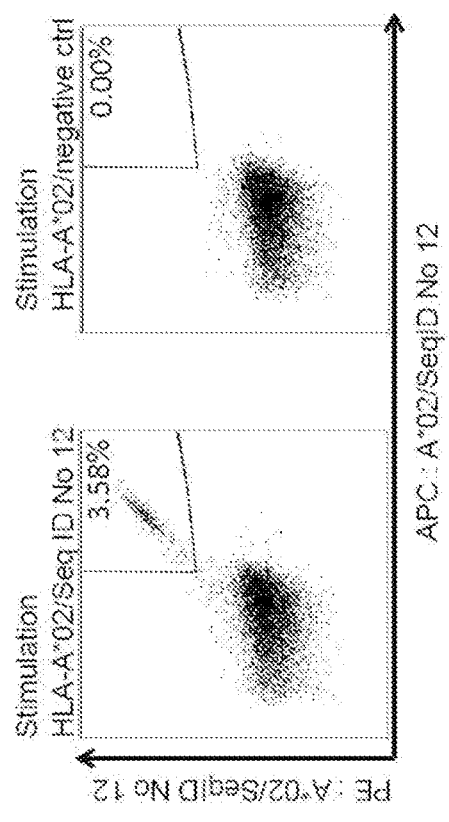
Figure 4C:
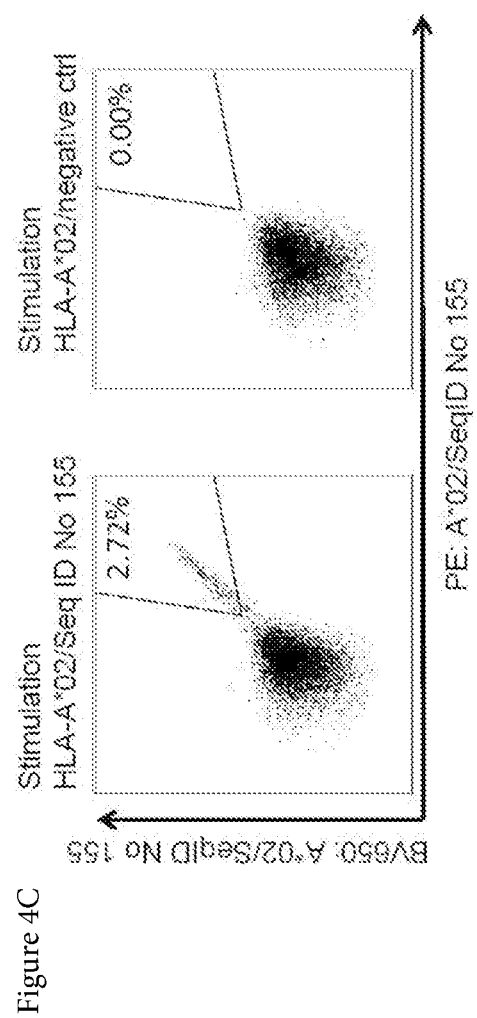

For tested HLA class I peptides, in vitro immunogenicity could be demonstrated by generation of peptide specific T-cell lines. Exemplary flow cytometry results after TUMAP-specific multimer staining for 2 peptides of the invention are shown in FIGS. 3A and 3B together with corresponding negative controls. Additional exemplary flow cytometry results after TUMAP-specific multimer staining for 3 peptides of the invention are shown in FIGS. 4A through 4C together with corresponding negative controls. Results for 33 peptides from the invention are summarized in Table 10A. Additional results for 29 peptides from the invention are summarized in Table 10B.

TABLE 10A in vitro immunogenicity of HLA class I peptides of the invention Exemplary results of in vitro immunogenicity experiments conducted by the applicant for the peptides of the invention. <20% = +; 20%-49% = ++; 50%-69% = +++; >=70% = ++++

| Seq ID No | Peptide Code | Sequence | Wells | Donors |
|---|---|---|---|---|
| 238 | FMN1-001 | KLLDKPEQFL | + | ++ |
| 241 | MYO10-002 | RLYTKLLNEA | +++ | ++++ |
| 243 | HSF2B-001 | ALAGIVTNV | + | ++++ |
| 247 | NOL11-001 | ALLNAILHSA | + | ++++ |
| 248 | MAGED2-003 | GLFAGLGGAGA | + | ++++ |
| 250 | AURKB-001 | RVLPPSALQSV | + | +++ |
| 252 | TOP2A-002 | YLLDMPLWYL | + | ++++ |
| 254 | SHCB-001 | FLMKNSDLYGA | + | ++++ |
| 257 | NCAPG-005 | VLLNEILEQV | ++ | ++++ |
| 262 | IL8-001 | KLAVALLAA | ++ | ++ |
| 264 | GYG2-001 | KVFDEVIEV | + | + |
| 267 | PTCD2-001 | LLTDNVVKL | + | ++++ |
| 269 | CEP55-001 | ALNESLVEC | + | ++++ |
| 271 | ECT2-001 | SLVQRVETI | + | ++ |
| 277 | KIF18A-001 | KTASINQNV | +++ | ++++ |
| 278 | SIX4-001 | SLITGQDLLSV | + | ++++ |
| 283 | MMP1-003 | YTFSGDVQL | + | ++++ |
| 287 | CHEK1-001 | KISDFGLATV | ++ | ++++ |
| 292 | MYBPH-001 | ALGDKFLLRV | + | ++++ |
| 294 | SMC2-001 | FLLAEDTKV | ++ | ++++ |
| 298 | CENPE-001 | KLQEEIPVL | + | ++++ |
| 308 | TMEM43-001 | KLLSDPNYGV | + | ++++ |
| 310 | IFT81-001 | ALASVIKEL | + | ++ |
| 315 | CERC-001 | KLSWDLIYL | ++ | ++++ |
| 318 | ATAD5-002 | SIIEYLPTL | + | ++++ |
| 320 | MSH6-001 | KIIGIMEEV | ++++ | ++++ |
| 321 | ELOVL2-001 | YLPTFFLTV | ++ | +++ |
| 322 | ATP-001 | SLHFLILYV | ++ | +++ |
| 323 | C11orf24-001 | VVDKTLLLV | +++ | ++++ |
| 326 | MCM5-001 | ALSGTLSGV | + | ++++ |
| 328 | ZNF318-001 | SLSQELVGV | + | ++ |
| 332 | DROSHA-001 | AVVEFLTSV | + | ++ |
| 336 | MET-001 | YVDPVITSI | ++ | ++++ |

TABLE 10B

In vitro immunogenicity of HLA class I peptides of the invention Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

| SEQ ID No | Sequence | Wells positive [%] |
|---|---|---|
| 3 | VLFKDPVSV | + |
| 4 | KTWDQVPFSV | + |
| 8 | SIIPYLLEA | ++ |
| 9 | SLAGLVLYV | ++ |
| 10 | KMTQYITEL | ++ |
| 11 | TLIELLLPKL | + |
| 12 | RLDDKTTNV | ++ |
| 13 | IQSETTVTV | ++ |
| 14 | VLYEMLYGL | +++ |
| 15 | VLYDPVVGC | + |
| 16 | GLFPSNFVTA | + |
| 17 | GVVHGVATV | + |
| 18 | SLADVVDTL | + |
| 20 | VISPHGIASV | ++ |
| 21 | FMYNFQLVTL | + |
| 31 | FLPRKFPSL | ++ |
| 33 | SLYSYFQKV | ++++ |
| 34 | YLINFEIRSL | + |
| 116 | LMDETMKEL | + |
| 121 | FLEDLVPYL | +++ |
| 128 | ALFPGDVDRL | + |
| 133 | ALDPAYTTL | + |
| 155 | GLAGFFASV | ++++ |
| 189 | KALQFLEEV | + |
| 191 | YLDKMNNNI | + |
| 192 | KLFTQIFGV | + |
| 211 | FLPFLTTEV | + |
| 213 | LLDPTNVFI | ++ |
| 232 | KILPDLNTV | + |

Example 4

Synthesis of Peptides

All peptides were synthesized using standard and well-established solid phase peptide synthesis using the Fmoc-strategy. Identity and purity of each individual peptide have been determined by mass spectrometry and analytical RP- HPLC. The peptides were obtained as white to off-white lyophilizes (trifluoro acetate salt) in purities of >50%. All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 11

MHC class I binding scores. Binding of HLA-class I restricted peptides to HLA-A*02:01 was ranged by peptide exchange yield: >10% = +; >20% = ++; >50 = +++; >75% = ++++

| SEQ ID No | Sequence | Peptide exchange |
|---|---|---|
| 1 | FLDVKELML | ++++ |
| 2 | VLLGENVEL | +++ |
| 3 | VLFKDPVSV | ++++ |
| 4 | KTWDQVPFSV | ++++ |
| 5 | ILDEGHILQL | ++++ |
| 6 | SIPDTIASV | +++ |
| 7 | NLQEKVPEL | +++ |
| 8 | SIIPYLLEA | ++++ |
| 9 | SLAGLVLYV | ++++ |
| 10 | KMTQYITEL | ++++ |
| 11 | TLIELLLPKL | ++++ |

TABLE 11-continued

MHC class I binding scores. Binding of HLA-class I restricted peptides to HLA-A*02:01 was ranged by peptide exchange yield: >10% = +; >20% = ++; >50 = +++; >75% = ++++

| SEQ ID No | Sequence | Peptide exchange |
|---|---|---|
| 12 | RLDDKTTNV | +++ |
| 13 | IQSETTVTV | ++++ |
| 14 | VLYEMLYGL | ++++ |
| 15 | VLYDPVVGC | ++++ |
| 16 | GLFPSNFVTA | ++++ |
| 17 | GVVHGVATV | ++++ |
| 18 | SLADVVDTL | ++++ |
| 19 | VLAVLGAVVAV | +++ |
| 20 | VISPHGIASV | ++++ |
| 21 | FMYNFQLVTL | ++ |
| 22 | KLLELQELVL | ++++ |
| 23 | FLGDPPPGL | +++ |
| 24 | SLVAILHLL | +++ |
| 25 | FIDPEQIQV | +++ |
| 26 | KIEDLIKYL | +++ |
| 27 | TLWYVPLSL | ++++ |
| 28 | IVDNTTMQL | +++ |
| 29 | ILDDVAMVL | +++ |
| 30 | VLFPMDLAL | +++ |
| 31 | FLPRKFPSL | ++++ |
| 32 | GLDIITNKV | +++ |
| 33 | SLYSYFQKV | ++++ |
| 34 | YLINFEIRSL | ++++ |
| 35 | ALFAAGANV | +++ |
| 36 | SVNGFISTL | ++ |
| 37 | TLKEYLESL | +++ |
| 38 | KLGFGTGVNVYL | ++++ |
| 39 | ALPPPPASI | +++ |
| 40 | LLSNTVSTL | +++ |
| 41 | LLDDPTNAHFI | +++ |
| 42 | VLKADVVLL | ++ |
| 43 | LLPDPLYSL | ++ |
| 44 | FLYTYIAKV | +++ |
| 45 | FVYGEPREL | +++ |
| 46 | VMSSTLYTV | ++++ |
| 47 | ALDSDPVGL | +++ |

TABLE 11-continued

MHC class I binding scores. Binding of HLA-class I restricted peptides to HLA-A*02:01 was ranged by peptide exchange yield: >10% = +; >20% = ++; >50 = +++; >75% = ++++

| SEQ ID No | Sequence | Peptide exchange |
|---|---|---|
| 48 | HLIGWTAFL | ++++ |
| 49 | ALLSQDFEL | ++++ |
| 50 | HLDQIFQNL | ++ |
| 51 | LIDKIIEYL | ++ |
| 52 | NLDYAILKL | + |
| 53 | ILDEEKFNV | +++ |
| 54 | LLDSGAFHL | +++ |
| 55 | NLDKLYHGL | + |
| 56 | ILDELVKSL | +++ |
| 57 | GILSFLPVL | +++ |
| 58 | ILGDWSIQV | ++++ |
| 59 | IIDDVMKEL | ++ |
| 60 | ILPEAQDYFL | ++++ |
| 61 | KLSVHVTAL | ++++ |
| 62 | LLDTTQKYL | ++++ |
| 63 | SIDDSDPIV | + |
| 64 | SLGPIMLTKI | ++ |
| 65 | TTLGGFAKV | ++ |
| 66 | VMFEYGMRL | ++++ |
| 67 | YVDSEGIVRM | + |
| 68 | FLAEAARSL | ++++ |
| 69 | IIDDKPIGL | +++ |
| 70 | LIDEAAQML | +++ |
| 71 | SLDEVAVSL | ++++ |
| 72 | TLLEVDAIVNA | ++++ |
| 73 | ELDKIYETL | + |
| 74 | GTIPLIESL | + |
| 75 | FMYAGQLTL | ++++ |
| 76 | QIDSIHLLL | +++ |
| 77 | SIDDVVKKL | ++ |
| 78 | ALKDLVNLI | ++++ |
| 79 | AVDNILLKL | +++ |
| 80 | FADELSHLL | +++ |
| 81 | FLDDGNQML | +++ |
| 82 | GIDDLHISL | +++ |
| 83 | GLDKVITVL | +++ |
| 84 | GLDTILQNL | ++++ |
| 85 | GLLDVMYQV | ++++ |
| 86 | HTLPHEIVVNL | +++ |
| 87 | IIDPPLHGQLL | ++ |
| 88 | ILDGIIREL | +++ |
| 89 | ILDNSPAFL | +++ |
| 90 | ILDYIHNGL | +++ |
| 91 | ILLDRLFSV | ++++ |
| 92 | KLPGFPTQDDEV | ++ |
| 93 | LLAKAVQNV | +++ |
| 94 | LLDAFSIKL | +++ |
| 95 | LLDALQHEL | +++ |
| 96 | LLDMSLVKL | +++ |
| 97 | NLDATVTAL | +++ |
| 98 | NLPNTNSILGV | +++ |
| 99 | NLPSELPQL | +++ |
| 100 | NLREILQNV | +++ |
| 101 | NVDENVAEL | ++ |
| 102 | RLPDQFSKL | +++ |
| 103 | SLDAVMPHL | +++ |
| 104 | SLDQIIQHL | +++ |
| 105 | SLKQTVVTL | +++ |
| 106 | TLSEICEFI | ++++ |
| 107 | TLVAFLQQV | ++++ |
| 108 | TVIRPLPGL | ++ |
| 109 | VIDDLIQKL | ++ |
| 110 | VLDTLTKVL | +++ |
| 111 | VLDVSFNRL | +++ |
| 112 | VLPAVLTRL | +++ |
| 113 | VLYSLVSKI | +++ |
| 114 | VVDDIVSKL | ++ |
| 115 | YIDDVFMGL | +++ |
| 116 | LMDETMKEL | ++++ |
| 117 | KQQASQVLV | +++ |
| 118 | TMIEICEKL | ++++ |
| 119 | SLGLGFISRV | +++ |

TABLE 11-continued

MHC class I binding scores. Binding of HLA-class I restricted peptides to HLA-A*02:01 was ranged by peptide exchange yield: >10% = +; >20% = ++; >50 = +++; >75% = ++++

| SEQ ID No | Sequence | Peptide exchange |
|---|---|---|
| 120 | QLMEGKVVL | ++++ |
| 121 | FLEDLVPYL | ++++ |
| 122 | YVDDFGVSV | +++ |
| 123 | LLGEGIPSA | ++++ |
| 124 | FLPQKIIYL | ++++ |
| 125 | YLFAFLNHL | ++++ |
| 126 | SLIDFVVTC | +++ |
| 127 | TLISDIEAVKA | +++ |
| 128 | ALFPGDVDRL | +++ |
| 129 | VLPDDLSGV | +++ |
| 130 | GLVDVLYTA | +++ |
| 131 | FVDPNGKISL | +++ |
| 132 | FLDASGAKL | ++++ |
| 133 | ALDPAYTTL | +++ |
| 134 | LLDEVLHTM | ++++ |
| 135 | FLDDQETRL | +++ |
| 136 | FAYDGKDYIAL | +++ |
| 137 | ILPSNLLTV | +++ |
| 138 | YLDKTFYNL | +++ |
| 139 | AVDATVNQV | +++ |
| 140 | RLEAYLARV | +++ |
| 141 | YVIDPIKGL | +++ |
| 142 | FVDGSAIQV | +++ |
| 143 | ILDDSALYL | ++++ |
| 144 | SVDEVEISV | +++ |
| 145 | TLPNIYVTL | +++ |
| 146 | GVGPVPARA | +++ |
| 147 | ILDDQTNKL | +++ |
| 148 | TLKDIVQTV | +++ |
| 149 | YLDTFALKL | ++++ |
| 150 | KLFPSPLQTL | ++++ |
| 151 | FLGEPASYLYL | ++++ |
| 152 | IMEDFTTFL | ++++ |
| 153 | RLDEVSREL | +++ |
| 154 | TLGTATFTV | ++++ |
| 155 | GLAGFFASV | ++++ |
| 156 | ALMDTDGSGKLNL | +++ |
| 157 | HLFETISQA | +++ |
| 158 | KLIPSIIVL | +++ |
| 159 | TILATVPLV | ++++ |
| 160 | ALDDISESI | ++++ |
| 161 | GLCDSIITI | ++++ |
| 162 | TLDGNPFLV | +++ |
| 163 | RLMANPEALKI | +++ |
| 164 | ALFFQLVDV | ++ |
| 165 | ALIEVLQPLI | ++++ |
| 166 | SIIPPLFTV | ++++ |
| 167 | KVLGDVIEV | ++++ |
| 168 | KLLAATLLL | ++++ |
| 169 | TLLESIQHV | ++++ |
| 170 | KLKEAVEAI | ++ |
| 171 | KVSGVILSV | ++++ |
| 172 | FLPAGIVAV | ++++ |
| 173 | ALDDIIYRA | +++ |
| 174 | TLLEGLTEL | +++ |
| 175 | VLDSVDVRL | ++++ |
| 176 | TLYEQEIEV | ++++ |
| 177 | ILWDTLLRL | ++++ |
| 178 | FAYDGKDYIA | ++++ |
| 179 | ALDDTVLQV | +++ |
| 180 | KLAEALYIA | +++ |
| 181 | GLIDLEANYL | ++++ |
| 182 | SVALVIHNV | ++++ |
| 183 | FLDSLIYGA | ++++ |
| 184 | VLFSSPPVILL | ++++ |
| 185 | ILADATAKM | ++++ |
| 186 | FLDHEMVFL | ++++ |
| 187 | SLPRPTPQA | +++ |
| 188 | VVVDPIQSV | +++ |
| 189 | KALQFLEEV | ++++ |
| 191 | YLDKMNNNI | ++++ |
| 192 | KLFTQIFGV | ++++ |

TABLE 11-continued

MHC class I binding scores. Binding of HLA-class I restricted peptides to HLA-A*02:01 was ranged by peptide exchange yield: >10% = +; >20% = ++; >50 = +++; >75% = ++++

| SEQ ID No | Sequence | Peptide exchange |
|---|---|---|
| 193 | ALDEPTTNL | +++ |
| 194 | TLDDIMAAV | +++ |
| 195 | IAAGIFNDL | + |
| 196 | ALEPIDITV | +++ |
| 197 | ALDSGFNSV | ++++ |
| 198 | EVVDKINQV | + |
| 199 | AIHTAILTL | ++ |
| 200 | LLEEINHFL | +++ |
| 201 | SLIDRTIKM | +++ |
| 202 | RVAFKINSV | +++ |
| 203 | FLNEDISKL | +++ |
| 204 | RMDEEFTKI | +++ |
| 205 | SLKSKVLSV | ++++ |
| 206 | LLYEDIPDKV | +++ |
| 207 | VQIGDIVTV | ++++ |
| 208 | YSDDIPHAL | ++ |
| 209 | SILDGLIHL | +++ |
| 210 | LLPELRDWGV | +++ |
| 211 | FLPFLTTEV | ++++ |
| 212 | LLKDSIVQL | +++ |
| 213 | LLDPTNVFI | ++++ |
| 214 | VLMEMSYRL | +++ |
| 215 | EVISKLYAV | +++ |
| 216 | TLLHFLAEL | ++++ |
| 217 | NMMSGISSV | +++ |
| 218 | STLHLVLRL | +++ |
| 219 | FLDSEVSEL | +++ |
| 220 | SAAEPTPAV | +++ |
| 221 | SLLPTEQPRL | +++ |
| 222 | LLSEIEEHL | ++++ |
| 223 | FLETNVPLL | +++ |
| 224 | ILDEPTNHL | ++ |
| 225 | VLFGAVITGA | ++++ |
| 226 | VLNEYFHNV | ++++ |
| 227 | FLLEQEKTQAL | ++++ |
| 228 | FLNLFNHTL | ++++ |
| 229 | LLEPFVHQV | ++++ |
| 230 | HLDEARTLL | ++++ |
| 231 | KMVGDVTGA | +++ |
| 232 | KILPDLNTV | ++++ |
| 233 | QLYNQIIKL | ++++ |
| 234 | KVPEIEVTV | ++++ |
| 235 | ALADLQEAV | ++++ |
| 236 | GLDSGFHSV | ++++ |
| 237 | VLYNESLQL | ++++ |

REFERENCE LIST

Aakula, A. et al., Eur. Urol. 69 (2016): 1120-1128
Aalto, Y. et al., Leukemia 15 (2001): 1721-1728
Abbruzzese, C. et al., J Exp. Clin Cancer Res 31 (2012): 4
Abraham, R. S. et al., Blood 105 (2005): 794-803
Adeola, H. A. et al., Oncotarget. 7 (2016): 13945-13964
Adinolfi, E. et al., J Osteoporos. 2012 (2012): 637863
Ahn, K. et al., Mol. Cells 28 (2009): 99-103
Akagi, T. et al., Int. J Cancer 125 (2009): 2349-2359
Al-Ahmadie, H. et al., Cancer Discov 4 (2014): 1014-1021
Alagaratnam, S. et al., Int. J Androl 34 (2011): e133-e150
Allison, J. P. et al., Science 270 (1995): 932-933
American Cancer Society, (2015), www.cancer.org
Amos, C. I. et al., Hum. Mol. Genet. 20 (2011): 5012-5023
Andersen, R. S. et al., Nat. Protoc. 7 (2012): 891-902
Angele, S. et al., Br. J Cancer 91 (2004): 783-787
Antonopoulou, K. et al., J Invest Dermatol. 135 (2015): 1074-1079
Appay, V. et al., Eur. J Immunol. 36 (2006): 1805-1814
Arigoni, M. et al., Am. J Pathol. 182 (2013): 2058-2070
Aso, T. et al., Anticancer Res 35 (2015): 6819-6827
Atanackovic, D. et al., Am. J Hematol. 86 (2011): 918-922
Atienza, J. M. et al., Mol Cancer Ther 4 (2005): 361-368
Augustin, A. et al., Mol. Cancer Ther. 12 (2013): 520-529
Avirneni-Vadlamudi, U. et al., J Clin Invest 122 (2012): 403-407
Bae, J. S. et al., Am. J Pathol. (2016)
Bae, J. S. et al., Int. J Cancer 136 (2015): 797-809
Banchereau, J. et al., Cell 106 (2001): 271-274
Bankovic, J. et al., Lung Cancer 67 (2010): 151-159
Baschieri, F. et al., Small GTPases. 6 (2015): 104-107
Baschieri, F. et al., Cell Cycle 14 (2015): 1139-1147
Bausch, D. et al., Clin Cancer Res. 17 (2011): 302-309
Beatty, G. et al., J Immunol 166 (2001): 2276-2282
Beggs, J. D., Nature 275 (1978): 104-109
Bekker-Jensen, S. et al., Nat Cell Biol 12 (2010): 80-86
Belle, L. et al., Sci. Signal. 8 (2015): ra18
Benevolo, M. et al., Am. J Surg. Pathol. 31 (2007): 76-84
Benjamini, Y. et al., Journal of the Royal Statistical Society. Series B (Methodological), Vol. 57 (1995): 289-300
Bertherat, J. et al., Cancer Res 63 (2003): 5308-5319

Bin, B. H. et al., PLoS. One. 10 (2015): e0129273
Boldrup, L. et al., Eur. J Cancer 48 (2012): 1401-1406
Bouameur, J. E. et al., J Invest Dermatol. 134 (2014): 885-894
Boulter, J. M. et al., Protein Eng 16 (2003): 707-711
Brandi, G. et al., Oncologist. 21 (2016): 600-607
Brastianos, P. K. et al., Nat Genet. 45 (2013): 285-289
Braumuller, H. et al., Nature (2013)
Bravou, V. et al., Cancer Invest 33 (2015): 387-397
Briffa, R. et al., PLoS. One. 10 (2015): e0144708
Brossart, P. et al., Blood 90 (1997): 1594-1599
Bruckdorfer, T. et al., Curr. Pharm. Biotechnol. 5 (2004): 29-43
Bueno, R. C. et al., Ann. Oncol 25 (2014): 69-75
Busse-Wicher, M. et al., Matrix Biol 35 (2014): 25-33
Caccia, D. et al., J Proteome. Res 10 (2011): 4196-4207
Campos-Parra, A. D. et al., Gynecol. Oncol 143 (2016): 406-413
Cantu, C. et al., Blood 117 (2011): 3669-3679
Carbonnelle-Puscian, A. et al., Leukemia 23 (2009): 952-960
Card, K. F. et al., Cancer Immunol. Immunother. 53 (2004): 345-357
Cassard, L. et al., Int. J Cancer 123 (2008): 2832-2839
Cesaratto, L. et al., Cell Death. Dis. 7 (2016): e2374
Chang, S. H. et al., Mol. Ther. 20 (2012): 2052-2063
Chanock, S. J. et al., Hum. Immunol. 65 (2004): 1211-1223
Chatterjee, N. et al., Cancer Biol Ther. 14 (2013): 658-671
Chen, H. et al., Proteomics. 14 (2014a): 51-73
Chen, J. et al., Gut Liver (2016)
Chen, J. H. et al., Int. J Biol Macromol. 81 (2015a): 615-623
Chen, K. et al., Nat Commun. 5 (2014b): 4682
Chen, R. et al., J Int. Med. Res 39 (2011): 533-540
Chen, S. et al., Int. J Oncol. 45 (2014c): 448-458
Chen, S. T. et al., Hum. Pathol. 39 (2008): 1854-1858
Chen, W. T. et al., Elife. 4 (2015b)
Chen, Y. et al., J Biol Chem 287 (2012): 24082-24091
Chiriva-Internati, M. et al., J Immunother. 34 (2011): 490-499
Chung, G. T. et al., J Pathol. 231 (2013): 158-167
Chung, K. Y. et al., Hepatology 54 (2011): 307-318
Chung, P. Y. et al., Semin. Arthritis Rheum. 41 (2012): 619-641
Cohen, C. J. et al., J Mol. Recognit. 16 (2003a): 324-332
Cohen, C. J. et al., J Immunol. 170 (2003b): 4349-4361
Cohen, S. N. et al., Proc. Natl. Acad. Sci. U.S.A 69 (1972): 2110-2114
Coligan, J. E. et al., Current Protocols in Protein Science (1995)
Colombetti, S. et al., J Immunol. 176 (2006): 2730-2738
Conesa-Zamora, P. et al., Clin Epigenetics. 7 (2015): 101
Coyaud, E. et al., Blood 115 (2010): 3089-3097
Cubillos-Rojas, M. et al., J Biol Chem 289 (2014): 14782-14795
Cuppini, L. et al., PLoS. One. 8 (2013): e74345
Dai, X. et al., Breast Cancer Res Treat. 149 (2015): 363-371
Daulat, A. M. et al., Dev. Cell 37 (2016): 311-325
Davidson, B. et al., Gynecol. Oncol 128 (2013): 364-370
Dawlaty, M. M. et al., Cell 133 (2008): 103-115
De, Marchi E. et al., Adv. Protein Chem Struct. Biol 104 (2016): 39-79
Deb, S. et al., Br. J Cancer 110 (2014): 1606-1613
Dengjel, J. et al., Clin Cancer Res 12 (2006): 4163-4170
Denkberg, G. et al., J Immunol. 171 (2003): 2197-2207
DeRycke, M. S. et al., Am. J Clin Pathol. 132 (2009): 846-856
Devaney, J. M. et al., Prostate Cancer Prostatic. Dis. (2013)
Devaney, J. M. et al., Epigenetics. 10 (2015): 319-328
Dong, F. et al., Pathol. Oncol Res 21 (2015a): 1273-1275
Dong, F. et al., Diagn. Pathol. 10 (2015b): 137
Dong, Y. et al., Mol. Cancer Ther. 4 (2005): 1047-1055
Doubrovina, E. S. et al., J Immunol. 171 (2003): 6891-6899
Drake, P. M. et al., J Proteome. Res 11 (2012): 2508-2520
Driscoll, D. R. et al., Cancer Res 76 (2016): 6911-6923
Dube, N. et al., Cell Signal. 20 (2008): 1608-1615
Dun, B. et al., Am. J Transl. Res 6 (2013a): 28-42
Dun, B. et al., Int. J Clin Exp. Pathol. 6 (2013b): 2880-2886
Dunn, L. L. et al., Carcinogenesis 27 (2006): 2157-2169
Dunwell, T. L. et al., Epigenetics. 4 (2009): 185-193
Dus-Szachniewicz, K. et al., Anticancer Res 35 (2015): 6551-6561
Emori, M. et al., PLoS. One. 8 (2013): e84187
Emori, M. et al., J Surg. Oncol 111 (2015): 975-979
Engel, B. E. et al., Cell Death. Dis. 4 (2013): e938
Erbe, A. K. et al., Clin Cancer Res (2016)
Fachal, L. et al., Nat Genet. 46 (2014): 891-894
Falk, K. et al., Nature 351 (1991): 290-296
Feijs, K. L. et al., Nat Rev Mol. Cell Biol 14 (2013): 443-451
Ferlay et al., GLOBOCAN 2012 v1.0, Cancer Incidence and Mortality Worldwide: IARC CancerBase No. 11 [Internet], (2013), globocan.iarc.fr
Fernandez, M. et al., Methods Mol. Biol 854 (2012): 239-252
Fernandez-Perez, M. P. et al., Neoplasia. 15 (2013): 826-839
Ferrero, S. et al., Histol. Histopathol. 30 (2015): 473-478
Feuerborn, A. et al., Oncogene 34 (2015): 1185-1195
Follenzi, A. et al., Nat Genet. 25 (2000): 217-222
Fong, L. et al., Proc. Natl. Acad. Sci. U.S.A 98 (2001): 8809-8814
Fouz, N. et al., Appl. Biochem. Biotechnol. 173 (2014): 1618-1639
Fu, W. et al., BMC. Cancer 9 (2009): 114
Fu, W. et al., Cell Rep. 17 (2016): 1505-1517
Fujimoto, A. et al., Nat Genet. 48 (2016): 500-509
Fujita, M. et al., J Biol Chem 282 (2007): 5736-5748
Fujitomo, T. et al., Cancer Res 72 (2012): 4110-4118
Gabrilovich, D. I. et al., Nat. Med 2 (1996): 1096-1103
Galland, F. et al., Endocr. Relat Cancer 17 (2010): 361-371
Gallou, C. et al., Oncotarget. (2016)
Gao, F. et al., Biochem. Biophys. Res Commun. 431 (2013): 610-616
Gao, J. et al., Dis. Markers 24 (2008): 127-134
Gasser, J. A. et al., Mol. Cell 56 (2014): 595-607
Gattinoni, L. et al., Nat. Rev. Immunol. 6 (2006): 383-393
Geoffroy-Perez, B. et al., Int. J Cancer 93 (2001): 288-293
Ghalali, A. et al., Carcinogenesis 35 (2014): 1547-1555
Giebel, S. et al., Hum. Immunol. 75 (2014): 508-513
Gillis, L. D. et al., Oncogene 32 (2013): 3598-3605
Gnjatic, S. et al., Proc Natl. Acad. Sci. U.S.A 100 (2003): 8862-8867
Godkin, A. et al., Int. Immunol 9 (1997): 905-911
Goodison, S. et al., BMC. Genomics 4 (2003): 39
Gorodeski, G. I., Expert. Opin. Ther. Targets. 13 (2009): 1313-1332
Gotoh, M. et al., Genes Chromosomes. Cancer 53 (2014): 1018-1032
Grant, R. C. et al., Hum. Genomics 7 (2013): 11
Green, M. R. et al., Molecular Cloning, A Laboratory Manual 4th (2012)
Greenfield, E. A., Antibodies: A Laboratory Manual 2nd (2014)
Grzmil, M. et al., Oncogene 29 (2010): 4080-4089
Guerreiro, A. S. et al., Mol. Cancer Res 9 (2011): 925-935
Guo, S. T. et al., Oncogene (2015)

Guo, X. et al., Cancer Epidemiol. 37 (2013): 732-736
Gustafsson, C. et al., Trends Biotechnol. 22 (2004): 346-353
Hagmann, W. et al., Neoplasia. 12 (2010): 740-747
Hao, J. et al., Oncotarget. 6 (2015): 42028-42039
Harato, M. et al., BMC. Neurosci. 13 (2012): 149
Hasumi, H. et al., Int. J Urol. 23 (2016): 204-210
Hasumi, H. et al., Proc. Natl. Acad. Sci. U.S.A 112 (2015): E1624-E1631
Haun, R. S. et al., J Proteomics. Bioinform. Suppl 10 (2014): S10003
He, H. et al., J Clin Endocrinol. Metab 98 (2013): E973-E980
Heinonen, H. et al., Int. J Cancer 137 (2015): 2374-2383
Hertzman, Johansson C. et al., Melanoma Res 23 (2013): 360-365
Heul-Nieuwenhuijsen, L. et al., BJU. Int. 103 (2009): 1574-1580
Hibbs, K. et al., Am. J Pathol. 165 (2004): 397-414
Hinrichs, C. S. et al., Nat Biotechnol. 31 (2013): 999-1008
Ho, C. Y. et al., Neuro. Oncol 15 (2013): 69-82
Hoover, H. et al., J Proteome. Res 14 (2015): 3670-3679
Hope, E. R. et al., Gynecol. Oncol 140 (2016): 503-511
Hou, M. et al., Oncol Lett. 10 (2015): 23-26
Hu, N. et al., Cancer Res 76 (2016): 1714-1723
Huang, A. H. et al., PLoS. One. 10 (2015): e0118530
Huang, J. M. et al., Oncogene 32 (2013): 2220-2229
Huang, L. et al., PLoS. One. 9 (2014a): e98185
Huang, L. et al., PLoS. One. 9 (2014b): e86336
Huang, X. et al., APMIS 122 (2014c): 1070-1079
Huynh, K. M. et al., Gene 433 (2009): 32-39
Hwang, M. L. et al., J Immunol. 179 (2007): 5829-5838
Ilboudo, A. et al., BMC. Cancer 14 (2014): 7
Ishiguro, H. et al., Oncogene 21 (2002): 6387-6394
Ishikawa, S. et al., J Exp. Clin Cancer Res. 22 (2003): 299-306
Ishiwata, T. et al., World J Gastroenterol. 17 (2011): 409-418
Isikbay, M. et al., Horm. Cancer 5 (2014): 72-89
Ito, M. et al., Breast Cancer Res Treat. 144 (2014): 59-69
Ito, Y. et al., Oncology 71 (2006): 388-393
Ivanov, S. V. et al., Br. J Cancer 109 (2013): 444-451
Januchowski, R. et al., Oncol Rep. 32 (2014): 1981-1990
Jia, W. et al., Oncotarget. (2016)
Jiang, L. et al., Hum. Genet. 129 (2011): 189-197
Jiang, W. et al., Tumour. Biol 36 (2015): 1289-1297
Jiao, S. et al., Cancer Cell 25 (2014): 166-180
Jin, Y. et al., PLoS. One. 10 (2015): e0144187
Jing, J. et al., Mol. Med Rep. 11 (2015): 3337-3343
Joel, M. et al., Mol. Cancer 14 (2015): 121
Jones, D. T. et al., Oncogene 28 (2009): 2119-2123
Jung, G. et al., Proc Natl Acad Sci USA 84 (1987): 4611-4615
Junnila, S. et al., BMC. Cancer 10 (2010): 73
Kang, M. R. et al., J Pathol. 217 (2009): 702-706
Kang, R. et al., Sci. Rep. 6 (2016): 19930
Karhemo, P. R. et al., J Proteomics. 77 (2012): 87-100
Karlsson, J. et al., Genes Chromosomes. Cancer 53 (2014): 381-391
Katada, K. et al., J Proteomics. 75 (2012): 1803-1815
Kataoka, K. et al., Nat Genet. 47 (2015): 1304-1315
Kato, N. et al., Int. J Cancer 41 (1988): 380-385
Kaufman, H. L. et al., Nat Rev Clin Oncol 10 (2013): 588-598
Kibbe, A. H., Handbook of Pharmaceutical Excipients rd (2000)
Killian, A. et al., Genes Chromosomes. Cancer 45 (2006): 874-881
Kim H R et al., J Clin Oncol 34, 2016 (suppl; abstr 6055) (2016)
Kim, J. et al., Genes Chromosomes. Cancer 54 (2015a): 681-691
Kim, O. et al., Mol. Med Rep. 12 (2015b): 2161-2168
Kim, S. Y. et al., Biochem. Biophys. Res Commun. 429 (2012): 173-179
Kimura, Y. et al., J Cancer 7 (2016): 702-710
Koo, S. et al., Anticancer Res 35 (2015): 3209-3215
Korshunov, A. et al., Am. J Pathol. 163 (2003): 1721-1727
Kousted, T. M. et al., Thromb. Haemost. 111 (2014): 29-40
Kren, B. T. et al., Breast Cancer Res 17 (2015): 19
Krieg, A. M., Nat. Rev. Drug Discov. 5 (2006): 471-484
Kuball, J. et al., Blood 109 (2007): 2331-2338
Kunicka, T. et al., BMC. Cancer 16 (2016): 795
Laczmanska, I. et al., Acta Biochim. Pol. 58 (2011): 467-470
Lahoz, A. et al., Oncogene 32 (2013): 4854-4860
Lajmi, N. et al., Br. J Haematol. 171 (2015): 752-762
Lan, L. et al., Int. J Cancer 126 (2010): 53-64
Lang, F. et al., Int. J Biochem. Cell Biol 42 (2010): 1571-1575
Lee, K. Y. et al., J Med. 35 (2004): 141-149
Lee, M. H. et al., J Korean Neurosurg. Soc. 43 (2008): 190-193
Lee, S. E. et al., Hematol. Oncol 32 (2014): 221-224
Lee, S. H. et al., Pathol. Oncol Res 21 (2015): 847-848
Lee, Y. H. et al., Food Chem 141 (2013): 381-388
Li, C. et al., PLoS. Biol 14 (2016a): e1002416
Li, F. et al., FEBS J 279 (2012a): 1261-1273
Li, F. et al., Gene 503 (2012b): 200-207
Li, G. et al., Histopathology 50 (2007): 642-647
Li, H. et al., Virchows Arch. 466 (2015a): 581-588
Li, H. et al., Med Oncol 32 (2015b): 83
Li, N. et al., Am. J Cancer Res 5 (2015c): 1158-1168
Li, W. et al., J Gastroenterol. Hepatol. 30 (2015d): 1085-1093
Li, W. H. et al., Dis. Markers 2015 (2015e): 657570
Li, Y. et al., Oncotarget. (2016b)
Liang, J. et al., Biochem. Cell Biol 85 (2007): 375-383
Liddy, N. et al., Nat. Med. 18 (2012): 980-987
Lim, J. H., BMB. Rep. 47 (2014): 405-410
Lim, J. H. et al., Cancer Genet. 207 (2014): 40-45
Lin, J. I. et al., Sci. Signal. 6 (2013): e4
Lind, G. E. et al., Mol. Cancer 10 (2011): 85
Linehan, W. M. et al., Nat Rev Urol. 7 (2010): 277-285
Linkous, A. et al., Clin Cancer Res 15 (2009): 1635-1644
Lips, E. H. et al., BMC. Cancer 8 (2008): 314
Lisitskaia, K. V. et al., Mol. Gen. Mikrobiol. Virusol. (2010): 34-37
Liu, H. et al., Tumour. Biol 36 (2015a): 5039-5049
Liu, H. et al., Anticancer Drugs 26 (2015b): 667-677
Liu, M. et al., Hepatology 55 (2012): 1754-1765
Liu, X. et al., Oncogene 32 (2013): 1266-1273
Ljunggren, H. G. et al., J Exp. Med 162 (1985): 1745-1759
Longenecker, B. M. et al., Ann N.Y. Acad. Sci. 690 (1993): 276-291
Lonsdale, J., Nat. Genet. 45 (2013): 580-585
Lukas, T. J. et al., Proc. Natl. Acad. Sci. U.S.A 78 (1981): 2791-2795
Lundblad, R. L., Chemical Reagents for Protein Modification 3rd (2004)
Luo, J. et al., Tumour. Biol 37 (2016): 10715-10721
Ma, J. et al., Mol. Med Rep. 12 (2015): 6060-6064
Maesako, Y. et al., Int. J Hematol. 99 (2014): 202-207
Man, X. Y. et al., Arthritis Res Ther. 14 (2012): R144
Manceau, G. et al., Int. J Cancer 132 (2013): 2217-2221
Mancuso, P. et al., PLoS. One. 9 (2014): e114713

Marchetti, A. et al., Int. J Oncol 18 (2001): 175-179
Marchi, S. et al., Cell Death. Dis. 3 (2012): e304
Markus, M. A. et al., Genomics 107 (2016): 138-144
Mathysen, D. et al., Eur. J Cancer 40 (2004): 1255-1261
Matsuda, Y. et al., Pancreas 45 (2016): 93-100
Matsuo, Y. et al., PLoS. One. 5 (2010): e10481
Matsuo, Y. et al., Sci. Transl. Med. 6 (2014): 259ra145
McKee, C. M. et al., Oncotarget. 6 (2015): 3784-3796
McKee, C. M. et al., Oncotarget. 4 (2013): 1-2
McKiernan, E. et al., Tumour. Biol 32 (2011): 441-450
McSherry, E. A. et al., Breast Cancer Res 13 (2011): R31
Melhem, A. et al., Clin Cancer Res 15 (2009): 3196-3204
Mendez, E. et al., Clin Cancer Res 17 (2011): 2466-2473
Mertens-Walker, I. et al., BMC. Cancer 15 (2015): 164
Meszaros, B. et al., Biol Direct. 11 (2016): 23
Meziere, C. et al., J Immunol 159 (1997): 3230-3237
Miyoshi, T. et al., Clin Cancer Res (2016)
Mochmann, L. H. et al., Oncotarget. 5 (2014): 351-362
Mohseni, M. et al., Proc. Natl. Acad. Sci. U.S.A 111 (2014): 17606-17611
Moon, J. W. et al., J Exp. Clin Cancer Res. 33 (2014): 4
Moretti, D. et al., PLoS. One. 10 (2015): e0117258
Morgan, R. A. et al., Science 314 (2006): 126-129
Mori, M. et al., Transplantation 64 (1997): 1017-1027
Morotti, A. et al., Cell Cycle 14 (2015): 973-979
Morowitz, M. J. et al., Clin Cancer Res 11 (2005): 2680-2685
Morris, M. R. et al., Oncogene 29 (2010): 2104-2117
Morrison, Joly M. et al., Cancer Res 76 (2016): 4752-4764
Mortara, L. et al., Clin Cancer Res. 12 (2006): 3435-3443
Mound, A. et al., Eur. J Cancer 49 (2013): 3738-3751
Mueller, L. N. et al., J Proteome. Res. 7 (2008): 51-61
Mueller, L. N. et al., Proteomics. 7 (2007): 3470-3480
Mughal, A. A. et al., Mol. Cancer 14 (2015): 160
Mumberg, D. et al., Proc. Natl. Acad. Sci. U.S.A 96 (1999): 8633-8638
Munkacsy, G. et al., Br. J Cancer 102 (2010): 361-368
Murrin, L. C. et al., J Neuroimmune. Pharmacol. 2 (2007): 290-295
Musolino, A. et al., J Clin Oncol 26 (2008): 1789-1796
Nagahara, A. et al., Biochem. Biophys. Res Commun. 391 (2010): 1641-1646
Nagel, S. et al., Genes Chromosomes. Cancer 53 (2014): 917-933
Nakayama, S. et al., Anticancer Res 35 (2015): 261-268
Nan, H. et al., Int. J Cancer 125 (2009): 909-917
National Cancer Institute, (5-6-2015), www.cancer.gov
Navarro, M. S. et al., Cancer Cell 13 (2008): 293-295
Ng, L. et al., Hepatology 58 (2013): 667-679
Ni, R. S. et al., Oncol Lett. 4 (2012): 1354-1360
Nord, H. et al., Neuro. Oncol 11 (2009): 803-818
Nordh, S. et al., World J Gastroenterol. 20 (2014): 8482-8490
Nordlund, J. et al., PLoS. ONE. 7 (2012): e34513
North, S. et al., J Urol. 191 (2014): 35-39
Norton, N. et al., Cancer Immunol. Res 2 (2014): 962-969
Oh, Y. et al., J Biol. Chem 287 (2012): 17517-17529
Olstad, O. K. et al., Anticancer Res 23 (2003): 2201-2216
Orr, B. et al., Oncogene 31 (2012): 1130-1142
Osterstrom, A. et al., Cancer Lett. 182 (2002): 175-182
Ozbay, P. O. et al., Onco. Targets. Ther. 6 (2013): 621-627
Pangeni, R. P. et al., Clin Epigenetics. 7 (2015): 57
Parhamifar, L. et al., Carcinogenesis 26 (2005): 1988-1998
Park, H. et al., Proc. Natl. Acad. Sci. U.S.A 111 (2014): 7066-7071
Parris, T. Z. et al., Clin Cancer Res 16 (2010): 3860-3874
Patai, A. V. et al., PLoS. One. 10 (2015): e0133836
Pei, X. H. et al., Biochem. Biophys. Res. Commun. 446 (2014): 322-327
Pei, Z. et al., PLoS. One. 8 (2013): e69392
Pelzl, L. et al., Cell Physiol Biochem. 37 (2015): 1857-1868
Peng, Y. et al., Cancer Res 75 (2015): 378-386
Perdigao, P. F. et al., Genes Chromosomes. Cancer 44 (2005): 204-211
Pereira, J. S. et al., Endocrine. 49 (2015): 204-214
Pestov, D. G. et al., Mol. Cell Biol 21 (2001): 4246-4255
Peters, D. G. et al., Cancer Epidemiol. Biomarkers Prev. 14 (2005): 1717-1723
Petit, C. S. et al., J Cell Biol 202 (2013): 1107-1122
Petricevic, B. et al., J Transl. Med 11 (2013): 307
Phan, G. Q. et al., Cancer Control 20 (2013): 289-297
Pho, L. N. et al., G. Ital. Dermatol. Venereol. 145 (2010): 37-45
Piepoli, A. et al., Exp. Biol Med. (Maywood.) 237 (2012): 1123-1128
Pignatelli, J. et al., J Biol Chem 287 (2012): 37309-37320
Pinheiro, J. et al., nlme: Linear and Nonlinear Mixed Effects Models (CRAN.R-project.org/packe=nlme) (2015)
Plebanski, M. et al., Eur. J Immunol 25 (1995): 1783-1787
Polevoda, B. et al., Biochem. Biophys. Res Commun. 308 (2003): 1-11
Porkka, K. P. et al., Genes Chromosomes. Cancer 39 (2004): 1-10
Porta, C. et al., Virology 202 (1994): 949-955
Powell, A. G. et al., J Cancer Res Clin Oncol 138 (2012): 723-728
Prasad, V. et al., J Virol. 88 (2014): 13086-13098
Qi, J. et al., Gut (2015)
Qin, J. et al., Cell Physiol Biochem. 35 (2015): 2069-2077
Qin, X. Y. et al., FEBS Lett. 585 (2011a): 3310-3315
Qin, Y. R. et al., Clin Cancer Res 17 (2011b): 46-55
Rabjerg, M. et al., APMIS 124 (2016): 372-383
Rajaram, M. et al., PLoS. One. 8 (2013): e66264
Rajkumar, T. et al., Asian Pac. J Cancer Prev. 16 (2015): 5211-5217
Rammensee, H. G. et al., Immunogenetics 50 (1999): 213-219
Rankin, C. T. et al., Blood 108 (2006): 2384-2391
Raymond, J. R., Jr. et al., J Ovarian. Res 7 (2014): 6
RefSeq, The NCBI handbook [Internet], Chapter 18, (2002), www.ncbi.nlm.nih.gov/books/NBK21091
Rho, J. H. et al., J Proteome. Res 7 (2008): 2959-2972
Rhyu, D. W. et al., Int. J Mol. Sci. 15 (2014): 9173-9183
Ricketts, C. J. et al., PLoS. ONE. 9 (2014): e85621
Rini, B. I. et al., Cancer 107 (2006): 67-74
Roberts, N. J. et al., Cancer Discov 2 (2012): 41-46
Rock, K. L. et al., Science 249 (1990): 918-921
Rodenko, B. et al., Nat. Protoc. 1 (2006): 1120-1132
Roger, S. et al., Biochim. Biophys. Acta 1848 (2015): 2584-2602
Rohrmoser, M. et al., Mol. Cell Biol 27 (2007): 3682-3694
Romagne, F. et al., Blood 114 (2009): 2667-2677
Rondeau, S. et al., Br. J Cancer 112 (2015): 1059-1066
Rouette, A. et al., Sci. Rep. 6 (2016): 34019
Ruffini, F. et al., Oncol Rep. 30 (2013): 2887-2896
Ruiz, J. F. et al., Nucleic Acids Res 32 (2004): 5861-5873
Russell, R. et al., Nat Commun. 6 (2015): 7677
S3-Leitlinie Melanom, 032-024OL, (2013)
Saiki, R. K. et al., Science 239 (1988): 487-491
Sakakura, C. et al., Anticancer Res 23 (2003): 3691-3697
Sakakura, H. et al., PLoS. One. 9 (2014): e83385
Sakashita, K. et al., Oncol Rep. 20 (2008): 1313-1319
Sakre, N. et al., Oncotarget. (2016)
Sanders, S. et al., Cytogenet. Cell Genet. 88 (2000): 324-325

Santarlasci, V. et al., Eur. J Immunol. 44 (2014): 654-661
Sarver, A. E. et al., Lab Invest 95 (2015): 1077-1088
Schmidt, L. S. et al., Expert. Opin. Orphan. Drugs 3 (2015a): 15-29
Schmidt, L. S. et al., Nat Rev Urol. 12 (2015b): 558-569
Schmitt, T. M. et al., Hum. Gene Ther. 20 (2009): 1240-1248
Scholten, K. B. et al., Clin Immunol. 119 (2006): 135-145
Schramm, A. et al., Nat Genet. 47 (2015): 872-877
Schwirzke, M. et al., Anticancer Res 18 (1998): 1409-1421
Scortegagna, M. et al., Cancer Res 75 (2015): 1399-1412
Seeger, F. H. et al., Immunogenetics 49 (1999): 571-576
Selvakumar, P. et al., Mol. Cancer 8 (2009): 65
Semczuk, A. et al., Pathol. Res Pract. 209 (2013): 740-744
Sesen, J. et al., Int. J Mol. Sci. 15 (2014): 2172-2190
Seydi, E. et al., Hepat. Mon. 15 (2015): e33073
Shah, P. et al., J Biol Chem 288 (2013): 12345-12352
Sherman, F. et al., Laboratory Course Manual for Methods in Yeast Genetics (1986)
Shi, J. et al., Yonsei Med J 57 (2016): 549-556
Shi, J. L. et al., Oncotarget. 6 (2015a): 5299-5309
Shi, X. et al., Oncol Lett. 10 (2015b): 1309-1314
Shi, Y. et al., Prostaglandins Leukot. Essent. Fatty Acids 74 (2006): 309-315
Shibao, K. et al., Cell Calcium 48 (2010): 315-323
Shimakata, T. et al., Histopathology (2016)
Shimizu, H. et al., Adv. Clin Exp. Med 25 (2016): 117-128
Shimozono, N. et al., Cancer Res 75 (2015): 4458-4465
Shin, J. et al., J Proteome. Res 13 (2014): 4919-4931
Shodeinde, A. et al., J Mol Biochem. 2 (2013): 18-26
Singh-Jasuja, H. et al., Cancer Immunol. Immunother. 53 (2004): 187-195
Small, E. J. et al., J Clin Oncol. 24 (2006): 3089-3094
Smirnova, T. et al., Oncotarget. (2016)
Smith, L. M. et al., Mol. Cancer Ther. 5 (2006): 1474-1482
Sousa, S. F. et al., Endocr. Relat Cancer 22 (2015): 399-408
Srivastava, N. et al., Cancer Manag. Res. 6 (2014): 279-289
Stacey, S. N. et al., Nat Genet. 41 (2009): 909-914
Steen, H. C. et al., J Interferon Cytokine Res. 32 (2012): 103-110
Stetler, D. A. et al., Proc. Natl. Acad. Sci. U.S.A 78 (1981): 7732-7736
Sticz, T. et al., J Clin Pathol. (2016)
Strissel, P. L. et al., Oncotarget. 3 (2012): 1204-1219
Sturm, M. et al., BMC. Bioinformatics. 9 (2008): 163
Su, H. T. et al., Mol. Cancer Res 11 (2013): 768-779
Suh, J. H. et al., Oncologist. 21 (2016): 684-691
Sumantran, V. N. et al., Indian J Biochem. Biophys. 52 (2015): 125-131
Supernat, A. et al., Oncol Lett. 4 (2012): 727-732
Suryo, Rahmanto Y. et al., Biochim. Biophys. Acta 1820 (2012): 237-243
Swift, M. et al., N. Engl. J Med. 316 (1987): 1289-1294
Tada, M. et al., Cancer Sci. 101 (2010): 1261-1269
Talarico, C. et al., Oncotarget. 6 (2015): 37511-37525
Tan, Y. et al., Curr. Pharm. Des 20 (2014): 81-87
Tanic, N. et al., Anticancer Res. 26 (2006): 2137-2142
Tao, J. et al., Tumour. Biol 35 (2014): 12083-12090
Telikicherla, D. et al., J Proteomics. Bioinform. 5 (2012): 122-126
Teufel, R. et al., Cell Mol. Life Sci. 62 (2005): 1755-1762
Thomsen, H. et al., BMC. Cancer 16 (2016): 227
Tokheim, C. et al., Cancer Res 76 (2016): 3719-3731
Tong, W. G. et al., Epigenetics. 5 (2010): 499-508
Tran, E. et al., Science 344 (2014): 641-645
Trivedi, S. et al., Clin Cancer Res 22 (2016): 5229-5237
Tsai, C. H. et al., Mol. Med Rep. 12 (2015): 7326-7334
Tschaharganeh, D. F. et al., Cell 158 (2014): 579-592
Tsun, Z. Y. et al., Mol. Cell 52 (2013): 495-505
Tyszkiewicz, T. et al., Folia Histochem. Cytobiol. 52 (2014): 79-89
Ueda, R. et al., Int. J Cancer 120 (2007): 1704-1711
van den Broek, E. et al., PLoS. One. 10 (2015): e0138141
Vasseur, S. et al., Mol. Cancer 4 (2005): 4
Velikkakath, A. K. et al., Mol. Biol. Cell 23 (2012): 896-909
Visuttijai, K. et al., PLoS. One. 11 (2016): e0164063
Vogler, M. et al., Cell Death. Differ. 15 (2008): 820-830
Wagenblast, E. et al., Nature 520 (2015): 358-362
Walter, S. et al., J. Immunol. 171 (2003): 4974-4978
Walter, S. et al., Nat Med. 18 (2012): 1254-1261
Wang, C. J. et al., Tumour. Biol 34 (2013a): 2141-2146
Wang, D. et al., Med. Oncol 32 (2015a): 461
Wang, J. et al., J Clin Invest 112 (2003): 535-543
Wang, J. et al., Cancer Prev. Res (Phila) 6 (2013b): 321-330
Wang, K. et al., J Cancer Res Clin Oncol 141 (2015b): 805-812
Wang, L. et al., Xi. Bao. Yu Fen. Zi. Mian. Yi. Xue. Za Zhi. 31 (2015c): 1251-1254
Wang, L. F. et al., Nan. Fang Yi. Ke. Da. Xue. Xue. Bao. 36 (2016a): 396-400
Wang, L. H. et al., Biochim. Biophys. Acta 1823 (2012): 505-513
Wang, L. J. et al., Oncotarget. 6 (2015d): 5932-5946
Wang, S. et al., Pharmacogenomics. 17 (2016b): 1637-1647
Wang, X. et al., Neuron 36 (2002): 843-854
Wang, Y. et al., Mol. Endocrinol. 28 (2014): 935-948
Wang, Z. et al., Science 304 (2004): 1164-1166
Wang, Z. et al., Melanoma Res 14 (2004): 107-114
Weber, A. M. et al., Pharmacol. Ther (2014)
Weigman, V. J. et al., Breast Cancer Res Treat. 133 (2012): 865-880
Welinder, C. et al., J Proteome. Res 13 (2014a): 1315-1326
Welinder, C. et al., PLoS. One. 9 (2014b): e110804
Weng, W. K. et al., Leuk. Lymphoma 50 (2009): 1494-1500
Westcot, S. E. et al., PLoS. One. 10 (2015): e0130688
Willcox, B. E. et al., Protein Sci. 8 (1999): 2418-2423
Wills, M. K. et al., Biochem. J 447 (2012): 1-16
Wills, M. K. et al., Mol. Biol Cell 25 (2014): 739-752
Wisniewski, A. et al., Hum. Immunol. 73 (2012): 927-931
World Cancer Report, (2014)
Wrzeszczynski, K. O. et al., PLoS. ONE. 6 (2011): e28503
Wu, X. et al., Hum. Mol. Genet. 21 (2012): 456-462
Wu, Y. et al., Int. J Mol. Sci. 17 (2016)
Wyatt, L. et al., Cell Cycle 7 (2008): 2290-2295
Xiao, F. et al., Hum. Genet. 133 (2014): 559-574
Xie, X. et al., Mol. Cell Biochem. 301 (2007): 115-122
Xing, X. et al., Gene 344 (2005): 161-169
Xu, G. et al., Gastroenterol. Res Pract. 2016 (2016a): 8431480
Xu, H. et al., Cell Rep. 9 (2014): 1781-1797
Xu, J. et al., Breast Cancer Res Treat. 134 (2012): 531-541
Xu, X. et al., Tumour. Biol (2016b)
Yafune, A. et al., Toxicol. Lett. 222 (2013): 295-302
Yang, B. et al., Tumour. Biol 36 (2015): 2111-2119
Yang, F. et al., Breast Cancer Res Treat. 145 (2014): 23-32
Yao, J. et al., Hepatology 51 (2010): 846-856
Yao, R. et al., Anticancer Res 27 (2007): 3051-3058
Yasui, W. et al., Gastric. Cancer 8 (2005): 86-94
Ye, B. G. et al., Oncotarget. (2016)
Yencilek, F. et al., Anticancer Res 36 (2016): 707-711
Yi, J. M. et al., Clin Cancer Res. (2013)
Yokota, T. et al., Acta Neuropathol. 111 (2006): 29-38
Yong, Z. W. et al., Sci. Rep. 4 (2014): 6073
You, J. et al., Hum. Pathol. 46 (2015): 1068-1077
Yu, J. et al., Oncogene 32 (2013): 307-317

Yue, C. et al., Int. J Cancer 136 (2015): 117-126
Zaremba, S. et al., Cancer Res. 57 (1997): 4570-4577
Zhang, F. et al., J Proteomics. 102 (2014a): 125-136
Zhang, J. F. et al., Zhongguo Shi Yan. Xue. Ye. Xue. Za Zhi. 22 (2014b): 909-913
Zhang, J. M. et al., Biochem. Biophys. Res Commun. 459 (2015): 252-258
Zhang, M. et al., Gynecol. Oncol 141 (2016a): 57-64
Zhang, N. et al., Oncotarget. (2016b)
Zhang, W. et al., Cell Res 24 (2014c): 331-343
Zhang, X. et al., Med Oncol 30 (2013): 454
Zhao, J. et al., Int. J Clin Exp. Pathol. 8 (2015a): 10784-10791
Zhao, Y. F. et al., Biochem. Biophys. Res Commun. 456 (2015b): 232-237
Zhao, Z. et al., Breast Cancer Res 16 (2014): 408
Zheng, Y. et al., Clin Cancer Res 19 (2013): 6484-6494
Zhou, J. et al., Carcinogenesis 36 (2015): 441-451
Zhou, Q. et al., Onco. Targets. Ther. 9 (2016): 2749-2757
Zhu, M. et al., Nucleic Acids Res 42 (2014a): 13074-13081
Zhu, Z. et al., PLoS. One. 9 (2014b): e96576
Zong, G. et al., Dig. Dis. Sci. 61 (2016): 2303-2314
Zufferey, R. et al., J Virol. 73 (1999): 2886-2892

The invention claimed is:

1. A method of treating a patient who has melanoma, comprising administering to said patient a composition comprising a population of activated T cells that selectively recognize cells in the patient that aberrantly express a peptide, wherein said peptide consists of the amino acid sequence ILDEGHILQL (SEQ ID NO: 5), wherein the peptide is in a complex with an MHC molecule.

2. The method of claim 1, wherein the T cells are autologous to the patient.

3. The method of claim 1, wherein the T cells are obtained from a healthy donor.

4. The method of claim 1, wherein the T cells are derived from tumor infiltrating lymphocytes or peripheral blood mononuclear cells.

5. The method of claim 1, further comprising expanding T cells in vitro.

6. The method of claim 1, wherein the MHC molecule is a class I molecule.

7. The method of claim 1, wherein the composition further comprises an adjuvant.

8. The method of claim 7, wherein the adjuvant is selected from the group consisting of anti-CD40 antibody, imiquimod, resiquimod, GM-CSF, cyclophosphamide, Sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. The method of claim 1, wherein the activated T cells are cytotoxic T cells produced by contacting T cells, in vitro, with an antigen presenting cell that expresses the peptide in a complex with an WIC class I molecule on the surface of the antigen presenting cell, for a period of time sufficient to activate said T cell specifically against the peptide.

10. The method of claim 9, wherein the antigen presenting cell is infected with a recombinant virus expressing the peptide.

11. The method of claim 10, wherein the antigen presenting cell is a dendritic cell or a macrophage.

12. The method of claim 9, further comprising stimulating the activated T cells in the presence of an anti-CD28 antibody and IL-12 to clonally expand the T cells.

13. The method of claim 1, wherein the population of activated T cells comprises CD8-positive cells.

14. The method of claim 7, wherein the adjuvant comprises IL-2.

15. The method of claim 7, wherein the adjuvant comprises IL-7.

16. The method of claim 7, wherein the adjuvant comprises IL-12.

17. The method of claim 7, wherein the adjuvant comprises IL-15.

18. The method of claim 7, wherein the adjuvant comprises IL-21.

19. The method of claim 1, wherein the T cells are derived from tumor infiltrating lymphocytes.

20. The method of claim 1, wherein the T cells are derived from peripheral blood mononuclear cells.

* * * * *

SEQUENCE LISTING

<160> NUMBER OF SEQ ID NOS: 340

<210> SEQ ID NO 1
<211> LENGTH: 9
<212> TYPE: PRT
<213> ORGANISM: Homo sapiens

<400> SEQUENCE: 1

Phe Leu Asp Val Lys Glu Leu Met Leu
1               5

<210> SEQ ID NO 2
<211> LENGTH: 9
<212> TYPE: PRT
<213> ORGANISM: Homo sapiens

<400> SEQUENCE: 2

Val Leu Leu Gly Glu Asn Val Glu Leu
1               5

<210> SEQ ID NO 3
<211> LENGTH: 9
<212> TYPE: PRT
<213> ORGANISM: Homo sapiens

<400> SEQUENCE: 3

Val Leu Phe Lys Asp Pro Val Ser Val
1               5

<210> SEQ ID NO 4
<211> LENGTH: 10
<212> TYPE: PRT
<213> ORGANISM: Homo sapiens

<400> SEQUENCE: 4

Lys Thr Trp Asp Gln Val Pro Phe Ser Val
1               5                   10

<210> SEQ ID NO 5
<211> LENGTH: 10
<212> TYPE: PRT
<213> ORGANISM: Homo sapiens

<400> SEQUENCE: 5

Ile Leu Asp Glu Gly His Ile Leu Gln Leu
1               5                   10

<210> SEQ ID NO 6
<211> LENGTH: 9
<212> TYPE: PRT
<213> ORGANISM: Homo sapiens

-continued

```
<400> SEQUENCE: 6

Ser Ile Pro Asp Thr Ile Ala Ser Val
1               5

<210> SEQ ID NO 7
<211> LENGTH: 9
<212> TYPE: PRT
<213> ORGANISM: Homo sapiens

<400> SEQUENCE: 7

Asn Leu Gln Glu Lys Val Pro Glu Leu
1               5

<210> SEQ ID NO 8
<211> LENGTH: 9
<212> TYPE: PRT
<213> ORGANISM: Homo sapiens

<400> SEQUENCE: 8

Ser Ile Ile Pro Tyr Leu Leu Glu Ala
1               5

<210> SEQ ID NO 9
<211> LENGTH: 9
<212> TYPE: PRT
<213> ORGANISM: Homo sapiens

<400> SEQUENCE: 9

Ser Leu Ala Gly Leu Val Leu Tyr Val
1               5

<210> SEQ ID NO 10
<211> LENGTH: 9
<212> TYPE: PRT
<213> ORGANISM: Homo sapiens

<400> SEQUENCE: 10

Lys Met Thr Gln Tyr Ile Thr Glu Leu
1               5

<210> SEQ ID NO 11
<211> LENGTH: 10
<212> TYPE: PRT
<213> ORGANISM: Homo sapiens

<400> SEQUENCE: 11

Thr Leu Ile Glu Leu Leu Leu Pro Lys Leu
1               5                   10

<210> SEQ ID NO 12
<211> LENGTH: 9
<212> TYPE: PRT
<213> ORGANISM: Homo sapiens

<400> SEQUENCE: 12

Arg Leu Asp Asp Lys Thr Thr Asn Val
1               5

<210> SEQ ID NO 13
<211> LENGTH: 9
<212> TYPE: PRT
<213> ORGANISM: Homo sapiens

<400> SEQUENCE: 13
```

Ile Gln Ser Glu Thr Thr Val Thr Val
1               5

<210> SEQ ID NO 14
<211> LENGTH: 9
<212> TYPE: PRT
<213> ORGANISM: Homo sapiens

<400> SEQUENCE: 14

Val Leu Tyr Glu Met Leu Tyr Gly Leu
1               5

<210> SEQ ID NO 15
<211> LENGTH: 9
<212> TYPE: PRT
<213> ORGANISM: Homo sapiens

<400> SEQUENCE: 15

Val Leu Tyr Asp Pro Val Val Gly Cys
1               5

<210> SEQ ID NO 16
<211> LENGTH: 10
<212> TYPE: PRT
<213> ORGANISM: Homo sapiens

<400> SEQUENCE: 16

Gly Leu Phe Pro Ser Asn Phe Val Thr Ala
1               5                   10

<210> SEQ ID NO 17
<211> LENGTH: 9
<212> TYPE: PRT
<213> ORGANISM: Homo sapiens

<400> SEQUENCE: 17

Gly Val Val His Gly Val Ala Thr Val
1               5

<210> SEQ ID NO 18
<211> LENGTH: 9
<212> TYPE: PRT
<213> ORGANISM: Homo sapiens

<400> SEQUENCE: 18

Ser Leu Ala Asp Val Val Asp Thr Leu
1               5

<210> SEQ ID NO 19
<211> LENGTH: 11
<212> TYPE: PRT
<213> ORGANISM: Homo sapiens

<400> SEQUENCE: 19

Val Leu Ala Val Leu Gly Ala Val Val Ala Val
1               5                   10

<210> SEQ ID NO 20
<211> LENGTH: 10
<212> TYPE: PRT
<213> ORGANISM: Homo sapiens

<400> SEQUENCE: 20

Val Ile Ser Pro His Gly Ile Ala Ser Val
1               5                   10

```
<210> SEQ ID NO 21
<211> LENGTH: 10
<212> TYPE: PRT
<213> ORGANISM: Homo sapiens

<400> SEQUENCE: 21

Phe Met Tyr Asn Phe Gln Leu Val Thr Leu
1               5                   10

<210> SEQ ID NO 22
<211> LENGTH: 10
<212> TYPE: PRT
<213> ORGANISM: Homo sapiens

<400> SEQUENCE: 22

Lys Leu Leu Glu Leu Gln Glu Leu Val Leu
1               5                   10

<210> SEQ ID NO 23
<211> LENGTH: 9
<212> TYPE: PRT
<213> ORGANISM: Homo sapiens

<400> SEQUENCE: 23

Phe Leu Gly Asp Pro Pro Pro Gly Leu
1               5

<210> SEQ ID NO 24
<211> LENGTH: 9
<212> TYPE: PRT
<213> ORGANISM: Homo sapiens

<400> SEQUENCE: 24

Ser Leu Val Ala Ile Leu His Leu Leu
1               5

<210> SEQ ID NO 25
<211> LENGTH: 9
<212> TYPE: PRT
<213> ORGANISM: Homo sapiens

<400> SEQUENCE: 25

Phe Ile Asp Pro Glu Gln Ile Gln Val
1               5

<210> SEQ ID NO 26
<211> LENGTH: 9
<212> TYPE: PRT
<213> ORGANISM: Homo sapiens

<400> SEQUENCE: 26

Lys Ile Glu Asp Leu Ile Lys Tyr Leu
1               5

<210> SEQ ID NO 27
<211> LENGTH: 9
<212> TYPE: PRT
<213> ORGANISM: Homo sapiens

<400> SEQUENCE: 27

Thr Leu Trp Tyr Val Pro Leu Ser Leu
1               5
```

-continued

<210> SEQ ID NO 28
<211> LENGTH: 9
<212> TYPE: PRT
<213> ORGANISM: Homo sapiens

<400> SEQUENCE: 28

Ile Val Asp Asn Thr Thr Met Gln Leu
1               5

<210> SEQ ID NO 29
<211> LENGTH: 9
<212> TYPE: PRT
<213> ORGANISM: Homo sapiens

<400> SEQUENCE: 29

Ile Leu Asp Asp Val Ala Met Val Leu
1               5

<210> SEQ ID NO 30
<211> LENGTH: 9
<212> TYPE: PRT
<213> ORGANISM: Homo sapiens

<400> SEQUENCE: 30

Val Leu Phe Pro Met Asp Leu Ala Leu
1               5

<210> SEQ ID NO 31
<211> LENGTH: 9
<212> TYPE: PRT
<213> ORGANISM: Homo sapiens

<400> SEQUENCE: 31

Phe Leu Pro Arg Lys Phe Pro Ser Leu
1               5

<210> SEQ ID NO 32
<211> LENGTH: 9
<212> TYPE: PRT
<213> ORGANISM: Homo sapiens

<400> SEQUENCE: 32

Gly Leu Asp Ile Ile Thr Asn Lys Val
1               5

<210> SEQ ID NO 33
<211> LENGTH: 9
<212> TYPE: PRT
<213> ORGANISM: Homo sapiens

<400> SEQUENCE: 33

Ser Leu Tyr Ser Tyr Phe Gln Lys Val
1               5

<210> SEQ ID NO 34
<211> LENGTH: 10
<212> TYPE: PRT
<213> ORGANISM: Homo sapiens

<400> SEQUENCE: 34

Tyr Leu Ile Asn Phe Glu Ile Arg Ser Leu
1               5                   10

<210> SEQ ID NO 35
<211> LENGTH: 9

```
<212> TYPE: PRT
<213> ORGANISM: Homo sapiens

<400> SEQUENCE: 35

Ala Leu Phe Ala Ala Gly Ala Asn Val
1               5

<210> SEQ ID NO 36
<211> LENGTH: 9
<212> TYPE: PRT
<213> ORGANISM: Homo sapiens

<400> SEQUENCE: 36

Ser Val Asn Gly Phe Ile Ser Thr Leu
1               5

<210> SEQ ID NO 37
<211> LENGTH: 9
<212> TYPE: PRT
<213> ORGANISM: Homo sapiens

<400> SEQUENCE: 37

Thr Leu Lys Glu Tyr Leu Glu Ser Leu
1               5

<210> SEQ ID NO 38
<211> LENGTH: 12
<212> TYPE: PRT
<213> ORGANISM: Homo sapiens

<400> SEQUENCE: 38

Lys Leu Gly Phe Gly Thr Gly Val Asn Val Tyr Leu
1               5                   10

<210> SEQ ID NO 39
<211> LENGTH: 9
<212> TYPE: PRT
<213> ORGANISM: Homo sapiens

<400> SEQUENCE: 39

Ala Leu Pro Pro Pro Pro Ala Ser Ile
1               5

<210> SEQ ID NO 40
<211> LENGTH: 9
<212> TYPE: PRT
<213> ORGANISM: Homo sapiens

<400> SEQUENCE: 40

Leu Leu Ser Asn Thr Val Ser Thr Leu
1               5

<210> SEQ ID NO 41
<211> LENGTH: 11
<212> TYPE: PRT
<213> ORGANISM: Homo sapiens

<400> SEQUENCE: 41

Leu Leu Asp Asp Pro Thr Asn Ala His Phe Ile
1               5                   10

<210> SEQ ID NO 42
<211> LENGTH: 9
<212> TYPE: PRT
<213> ORGANISM: Homo sapiens
```

```
<400> SEQUENCE: 42

Val Leu Lys Ala Asp Val Val Leu Leu
1               5

<210> SEQ ID NO 43
<211> LENGTH: 9
<212> TYPE: PRT
<213> ORGANISM: Homo sapiens

<400> SEQUENCE: 43

Leu Leu Pro Asp Pro Leu Tyr Ser Leu
1               5

<210> SEQ ID NO 44
<211> LENGTH: 9
<212> TYPE: PRT
<213> ORGANISM: Homo sapiens

<400> SEQUENCE: 44

Phe Leu Tyr Thr Tyr Ile Ala Lys Val
1               5

<210> SEQ ID NO 45
<211> LENGTH: 9
<212> TYPE: PRT
<213> ORGANISM: Homo sapiens

<400> SEQUENCE: 45

Phe Val Tyr Gly Glu Pro Arg Glu Leu
1               5

<210> SEQ ID NO 46
<211> LENGTH: 9
<212> TYPE: PRT
<213> ORGANISM: Homo sapiens

<400> SEQUENCE: 46

Val Met Ser Ser Thr Leu Tyr Thr Val
1               5

<210> SEQ ID NO 47
<211> LENGTH: 9
<212> TYPE: PRT
<213> ORGANISM: Homo sapiens

<400> SEQUENCE: 47

Ala Leu Asp Ser Asp Pro Val Gly Leu
1               5

<210> SEQ ID NO 48
<211> LENGTH: 9
<212> TYPE: PRT
<213> ORGANISM: Homo sapiens

<400> SEQUENCE: 48

His Leu Ile Gly Trp Thr Ala Phe Leu
1               5

<210> SEQ ID NO 49
<211> LENGTH: 9
<212> TYPE: PRT
<213> ORGANISM: Homo sapiens

<400> SEQUENCE: 49
```

Ala Leu Leu Ser Gln Asp Phe Glu Leu
1               5

<210> SEQ ID NO 50
<211> LENGTH: 9
<212> TYPE: PRT
<213> ORGANISM: Homo sapiens

<400> SEQUENCE: 50

His Leu Asp Gln Ile Phe Gln Asn Leu
1               5

<210> SEQ ID NO 51
<211> LENGTH: 9
<212> TYPE: PRT
<213> ORGANISM: Homo sapiens

<400> SEQUENCE: 51

Leu Ile Asp Lys Ile Ile Glu Tyr Leu
1               5

<210> SEQ ID NO 52
<211> LENGTH: 9
<212> TYPE: PRT
<213> ORGANISM: Homo sapiens

<400> SEQUENCE: 52

Asn Leu Asp Tyr Ala Ile Leu Lys Leu
1               5

<210> SEQ ID NO 53
<211> LENGTH: 9
<212> TYPE: PRT
<213> ORGANISM: Homo sapiens

<400> SEQUENCE: 53

Ile Leu Asp Glu Glu Lys Phe Asn Val
1               5

<210> SEQ ID NO 54
<211> LENGTH: 9
<212> TYPE: PRT
<213> ORGANISM: Homo sapiens

<400> SEQUENCE: 54

Leu Leu Asp Ser Gly Ala Phe His Leu
1               5

<210> SEQ ID NO 55
<211> LENGTH: 9
<212> TYPE: PRT
<213> ORGANISM: Homo sapiens

<400> SEQUENCE: 55

Asn Leu Asp Lys Leu Tyr His Gly Leu
1               5

<210> SEQ ID NO 56
<211> LENGTH: 9
<212> TYPE: PRT
<213> ORGANISM: Homo sapiens

<400> SEQUENCE: 56

Ile Leu Asp Glu Leu Val Lys Ser Leu

```
1               5
```

<210> SEQ ID NO 57
<211> LENGTH: 9
<212> TYPE: PRT
<213> ORGANISM: Homo sapiens

<400> SEQUENCE: 57

```
Gly Ile Leu Ser Phe Leu Pro Val Leu
1               5
```

<210> SEQ ID NO 58
<211> LENGTH: 9
<212> TYPE: PRT
<213> ORGANISM: Homo sapiens

<400> SEQUENCE: 58

```
Ile Leu Gly Asp Trp Ser Ile Gln Val
1               5
```

<210> SEQ ID NO 59
<211> LENGTH: 9
<212> TYPE: PRT
<213> ORGANISM: Homo sapiens

<400> SEQUENCE: 59

```
Ile Ile Asp Asp Val Met Lys Glu Leu
1               5
```

<210> SEQ ID NO 60
<211> LENGTH: 10
<212> TYPE: PRT
<213> ORGANISM: Homo sapiens

<400> SEQUENCE: 60

```
Ile Leu Pro Glu Ala Gln Asp Tyr Phe Leu
1               5                   10
```

<210> SEQ ID NO 61
<211> LENGTH: 9
<212> TYPE: PRT
<213> ORGANISM: Homo sapiens

<400> SEQUENCE: 61

```
Lys Leu Ser Val His Val Thr Ala Leu
1               5
```

<210> SEQ ID NO 62
<211> LENGTH: 9
<212> TYPE: PRT
<213> ORGANISM: Homo sapiens

<400> SEQUENCE: 62

```
Leu Leu Asp Thr Thr Gln Lys Tyr Leu
1               5
```

<210> SEQ ID NO 63
<211> LENGTH: 9
<212> TYPE: PRT
<213> ORGANISM: Homo sapiens

<400> SEQUENCE: 63

```
Ser Ile Asp Asp Ser Asp Pro Ile Val
1               5
```

<210> SEQ ID NO 64
<211> LENGTH: 10
<212> TYPE: PRT
<213> ORGANISM: Homo sapiens

<400> SEQUENCE: 64

Ser Leu Gly Pro Ile Met Leu Thr Lys Ile
1               5                   10

<210> SEQ ID NO 65
<211> LENGTH: 9
<212> TYPE: PRT
<213> ORGANISM: Homo sapiens

<400> SEQUENCE: 65

Thr Thr Leu Gly Gly Phe Ala Lys Val
1               5

<210> SEQ ID NO 66
<211> LENGTH: 9
<212> TYPE: PRT
<213> ORGANISM: Homo sapiens

<400> SEQUENCE: 66

Val Met Phe Glu Tyr Gly Met Arg Leu
1               5

<210> SEQ ID NO 67
<211> LENGTH: 10
<212> TYPE: PRT
<213> ORGANISM: Homo sapiens

<400> SEQUENCE: 67

Tyr Val Asp Ser Glu Gly Ile Val Arg Met
1               5                   10

<210> SEQ ID NO 68
<211> LENGTH: 9
<212> TYPE: PRT
<213> ORGANISM: Homo sapiens

<400> SEQUENCE: 68

Phe Leu Ala Glu Ala Ala Arg Ser Leu
1               5

<210> SEQ ID NO 69
<211> LENGTH: 9
<212> TYPE: PRT
<213> ORGANISM: Homo sapiens

<400> SEQUENCE: 69

Ile Ile Asp Asp Lys Pro Ile Gly Leu
1               5

<210> SEQ ID NO 70
<211> LENGTH: 9
<212> TYPE: PRT
<213> ORGANISM: Homo sapiens

<400> SEQUENCE: 70

Leu Ile Asp Glu Ala Ala Gln Met Leu
1               5

<210> SEQ ID NO 71

```
<211> LENGTH: 9
<212> TYPE: PRT
<213> ORGANISM: Homo sapiens

<400> SEQUENCE: 71

Ser Leu Asp Glu Val Ala Val Ser Leu
1               5

<210> SEQ ID NO 72
<211> LENGTH: 11
<212> TYPE: PRT
<213> ORGANISM: Homo sapiens

<400> SEQUENCE: 72

Thr Leu Leu Glu Val Asp Ala Ile Val Asn Ala
1               5                   10

<210> SEQ ID NO 73
<211> LENGTH: 9
<212> TYPE: PRT
<213> ORGANISM: Homo sapiens

<400> SEQUENCE: 73

Glu Leu Asp Lys Ile Tyr Glu Thr Leu
1               5

<210> SEQ ID NO 74
<211> LENGTH: 9
<212> TYPE: PRT
<213> ORGANISM: Homo sapiens

<400> SEQUENCE: 74

Gly Thr Ile Pro Leu Ile Glu Ser Leu
1               5

<210> SEQ ID NO 75
<211> LENGTH: 9
<212> TYPE: PRT
<213> ORGANISM: Homo sapiens

<400> SEQUENCE: 75

Phe Met Tyr Ala Gly Gln Leu Thr Leu
1               5

<210> SEQ ID NO 76
<211> LENGTH: 9
<212> TYPE: PRT
<213> ORGANISM: Homo sapiens

<400> SEQUENCE: 76

Gln Ile Asp Ser Ile His Leu Leu Leu
1               5

<210> SEQ ID NO 77
<211> LENGTH: 9
<212> TYPE: PRT
<213> ORGANISM: Homo sapiens

<400> SEQUENCE: 77

Ser Ile Asp Asp Val Val Lys Lys Leu
1               5

<210> SEQ ID NO 78
<211> LENGTH: 9
<212> TYPE: PRT
```

```
<213> ORGANISM: Homo sapiens

<400> SEQUENCE: 78

Ala Leu Lys Asp Leu Val Asn Leu Ile
1               5

<210> SEQ ID NO 79
<211> LENGTH: 9
<212> TYPE: PRT
<213> ORGANISM: Homo sapiens

<400> SEQUENCE: 79

Ala Val Asp Asn Ile Leu Leu Lys Leu
1               5

<210> SEQ ID NO 80
<211> LENGTH: 9
<212> TYPE: PRT
<213> ORGANISM: Homo sapiens

<400> SEQUENCE: 80

Phe Ala Asp Glu Leu Ser His Leu Leu
1               5

<210> SEQ ID NO 81
<211> LENGTH: 9
<212> TYPE: PRT
<213> ORGANISM: Homo sapiens

<400> SEQUENCE: 81

Phe Leu Asp Asp Gly Asn Gln Met Leu
1               5

<210> SEQ ID NO 82
<211> LENGTH: 9
<212> TYPE: PRT
<213> ORGANISM: Homo sapiens

<400> SEQUENCE: 82

Gly Ile Asp Asp Leu His Ile Ser Leu
1               5

<210> SEQ ID NO 83
<211> LENGTH: 9
<212> TYPE: PRT
<213> ORGANISM: Homo sapiens

<400> SEQUENCE: 83

Gly Leu Asp Lys Val Ile Thr Val Leu
1               5

<210> SEQ ID NO 84
<211> LENGTH: 9
<212> TYPE: PRT
<213> ORGANISM: Homo sapiens

<400> SEQUENCE: 84

Gly Leu Asp Thr Ile Leu Gln Asn Leu
1               5

<210> SEQ ID NO 85
<211> LENGTH: 9
<212> TYPE: PRT
<213> ORGANISM: Homo sapiens
```

```
<400> SEQUENCE: 85

Gly Leu Leu Asp Val Met Tyr Gln Val
1               5

<210> SEQ ID NO 86
<211> LENGTH: 11
<212> TYPE: PRT
<213> ORGANISM: Homo sapiens

<400> SEQUENCE: 86

His Thr Leu Pro His Glu Ile Val Val Asn Leu
1               5                   10

<210> SEQ ID NO 87
<211> LENGTH: 11
<212> TYPE: PRT
<213> ORGANISM: Homo sapiens

<400> SEQUENCE: 87

Ile Ile Asp Pro Pro Leu His Gly Gln Leu Leu
1               5                   10

<210> SEQ ID NO 88
<211> LENGTH: 9
<212> TYPE: PRT
<213> ORGANISM: Homo sapiens

<400> SEQUENCE: 88

Ile Leu Asp Gly Ile Ile Arg Glu Leu
1               5

<210> SEQ ID NO 89
<211> LENGTH: 9
<212> TYPE: PRT
<213> ORGANISM: Homo sapiens

<400> SEQUENCE: 89

Ile Leu Asp Asn Ser Pro Ala Phe Leu
1               5

<210> SEQ ID NO 90
<211> LENGTH: 9
<212> TYPE: PRT
<213> ORGANISM: Homo sapiens

<400> SEQUENCE: 90

Ile Leu Asp Tyr Ile His Asn Gly Leu
1               5

<210> SEQ ID NO 91
<211> LENGTH: 9
<212> TYPE: PRT
<213> ORGANISM: Homo sapiens

<400> SEQUENCE: 91

Ile Leu Leu Asp Arg Leu Phe Ser Val
1               5

<210> SEQ ID NO 92
<211> LENGTH: 12
<212> TYPE: PRT
<213> ORGANISM: Homo sapiens

<400> SEQUENCE: 92
```

Lys Leu Pro Gly Phe Pro Thr Gln Asp Asp Glu Val
1               5                   10

<210> SEQ ID NO 93
<211> LENGTH: 9
<212> TYPE: PRT
<213> ORGANISM: Homo sapiens

<400> SEQUENCE: 93

Leu Leu Ala Lys Ala Val Gln Asn Val
1               5

<210> SEQ ID NO 94
<211> LENGTH: 9
<212> TYPE: PRT
<213> ORGANISM: Homo sapiens

<400> SEQUENCE: 94

Leu Leu Asp Ala Phe Ser Ile Lys Leu
1               5

<210> SEQ ID NO 95
<211> LENGTH: 9
<212> TYPE: PRT
<213> ORGANISM: Homo sapiens

<400> SEQUENCE: 95

Leu Leu Asp Ala Leu Gln His Glu Leu
1               5

<210> SEQ ID NO 96
<211> LENGTH: 9
<212> TYPE: PRT
<213> ORGANISM: Homo sapiens

<400> SEQUENCE: 96

Leu Leu Asp Met Ser Leu Val Lys Leu
1               5

<210> SEQ ID NO 97
<211> LENGTH: 9
<212> TYPE: PRT
<213> ORGANISM: Homo sapiens

<400> SEQUENCE: 97

Asn Leu Asp Ala Thr Val Thr Ala Leu
1               5

<210> SEQ ID NO 98
<211> LENGTH: 11
<212> TYPE: PRT
<213> ORGANISM: Homo sapiens

<400> SEQUENCE: 98

Asn Leu Pro Asn Thr Asn Ser Ile Leu Gly Val
1               5                   10

<210> SEQ ID NO 99
<211> LENGTH: 9
<212> TYPE: PRT
<213> ORGANISM: Homo sapiens

<400> SEQUENCE: 99

Asn Leu Pro Ser Glu Leu Pro Gln Leu
1               5

```
<210> SEQ ID NO 100
<211> LENGTH: 9
<212> TYPE: PRT
<213> ORGANISM: Homo sapiens

<400> SEQUENCE: 100

Asn Leu Arg Glu Ile Leu Gln Asn Val
1               5

<210> SEQ ID NO 101
<211> LENGTH: 9
<212> TYPE: PRT
<213> ORGANISM: Homo sapiens

<400> SEQUENCE: 101

Asn Val Asp Glu Asn Val Ala Glu Leu
1               5

<210> SEQ ID NO 102
<211> LENGTH: 9
<212> TYPE: PRT
<213> ORGANISM: Homo sapiens

<400> SEQUENCE: 102

Arg Leu Pro Asp Gln Phe Ser Lys Leu
1               5

<210> SEQ ID NO 103
<211> LENGTH: 9
<212> TYPE: PRT
<213> ORGANISM: Homo sapiens

<400> SEQUENCE: 103

Ser Leu Asp Ala Val Met Pro His Leu
1               5

<210> SEQ ID NO 104
<211> LENGTH: 9
<212> TYPE: PRT
<213> ORGANISM: Homo sapiens

<400> SEQUENCE: 104

Ser Leu Asp Gln Ile Ile Gln His Leu
1               5

<210> SEQ ID NO 105
<211> LENGTH: 9
<212> TYPE: PRT
<213> ORGANISM: Homo sapiens

<400> SEQUENCE: 105

Ser Leu Lys Gln Thr Val Val Thr Leu
1               5

<210> SEQ ID NO 106
<211> LENGTH: 9
<212> TYPE: PRT
<213> ORGANISM: Homo sapiens

<400> SEQUENCE: 106

Thr Leu Ser Glu Ile Cys Glu Phe Ile
1               5
```

<210> SEQ ID NO 107
<211> LENGTH: 9
<212> TYPE: PRT
<213> ORGANISM: Homo sapiens

<400> SEQUENCE: 107

Thr Leu Val Ala Phe Leu Gln Gln Val
1               5

<210> SEQ ID NO 108
<211> LENGTH: 9
<212> TYPE: PRT
<213> ORGANISM: Homo sapiens

<400> SEQUENCE: 108

Thr Val Ile Arg Pro Leu Pro Gly Leu
1               5

<210> SEQ ID NO 109
<211> LENGTH: 9
<212> TYPE: PRT
<213> ORGANISM: Homo sapiens

<400> SEQUENCE: 109

Val Ile Asp Asp Leu Ile Gln Lys Leu
1               5

<210> SEQ ID NO 110
<211> LENGTH: 9
<212> TYPE: PRT
<213> ORGANISM: Homo sapiens

<400> SEQUENCE: 110

Val Leu Asp Thr Leu Thr Lys Val Leu
1               5

<210> SEQ ID NO 111
<211> LENGTH: 9
<212> TYPE: PRT
<213> ORGANISM: Homo sapiens

<400> SEQUENCE: 111

Val Leu Asp Val Ser Phe Asn Arg Leu
1               5

<210> SEQ ID NO 112
<211> LENGTH: 9
<212> TYPE: PRT
<213> ORGANISM: Homo sapiens

<400> SEQUENCE: 112

Val Leu Pro Ala Val Leu Thr Arg Leu
1               5

<210> SEQ ID NO 113
<211> LENGTH: 9
<212> TYPE: PRT
<213> ORGANISM: Homo sapiens

<400> SEQUENCE: 113

Val Leu Tyr Ser Leu Val Ser Lys Ile
1               5

<210> SEQ ID NO 114
<211> LENGTH: 9

```
<212> TYPE: PRT
<213> ORGANISM: Homo sapiens

<400> SEQUENCE: 114

Val Val Asp Asp Ile Val Ser Lys Leu
1               5

<210> SEQ ID NO 115
<211> LENGTH: 9
<212> TYPE: PRT
<213> ORGANISM: Homo sapiens

<400> SEQUENCE: 115

Tyr Ile Asp Asp Val Phe Met Gly Leu
1               5

<210> SEQ ID NO 116
<211> LENGTH: 9
<212> TYPE: PRT
<213> ORGANISM: Homo sapiens

<400> SEQUENCE: 116

Leu Met Asp Glu Thr Met Lys Glu Leu
1               5

<210> SEQ ID NO 117
<211> LENGTH: 9
<212> TYPE: PRT
<213> ORGANISM: Homo sapiens

<400> SEQUENCE: 117

Lys Gln Gln Ala Ser Gln Val Leu Val
1               5

<210> SEQ ID NO 118
<211> LENGTH: 9
<212> TYPE: PRT
<213> ORGANISM: Homo sapiens

<400> SEQUENCE: 118

Thr Met Ile Glu Ile Cys Glu Lys Leu
1               5

<210> SEQ ID NO 119
<211> LENGTH: 10
<212> TYPE: PRT
<213> ORGANISM: Homo sapiens

<400> SEQUENCE: 119

Ser Leu Gly Leu Gly Phe Ile Ser Arg Val
1               5                   10

<210> SEQ ID NO 120
<211> LENGTH: 9
<212> TYPE: PRT
<213> ORGANISM: Homo sapiens

<400> SEQUENCE: 120

Gln Leu Met Glu Gly Lys Val Val Leu
1               5

<210> SEQ ID NO 121
<211> LENGTH: 9
<212> TYPE: PRT
<213> ORGANISM: Homo sapiens
```

<400> SEQUENCE: 121

Phe Leu Glu Asp Leu Val Pro Tyr Leu
1               5

<210> SEQ ID NO 122
<211> LENGTH: 9
<212> TYPE: PRT
<213> ORGANISM: Homo sapiens

<400> SEQUENCE: 122

Tyr Val Asp Asp Phe Gly Val Ser Val
1               5

<210> SEQ ID NO 123
<211> LENGTH: 9
<212> TYPE: PRT
<213> ORGANISM: Homo sapiens

<400> SEQUENCE: 123

Leu Leu Gly Glu Gly Ile Pro Ser Ala
1               5

<210> SEQ ID NO 124
<211> LENGTH: 9
<212> TYPE: PRT
<213> ORGANISM: Homo sapiens

<400> SEQUENCE: 124

Phe Leu Pro Gln Lys Ile Ile Tyr Leu
1               5

<210> SEQ ID NO 125
<211> LENGTH: 9
<212> TYPE: PRT
<213> ORGANISM: Homo sapiens

<400> SEQUENCE: 125

Tyr Leu Phe Ala Phe Leu Asn His Leu
1               5

<210> SEQ ID NO 126
<211> LENGTH: 9
<212> TYPE: PRT
<213> ORGANISM: Homo sapiens

<400> SEQUENCE: 126

Ser Leu Ile Asp Phe Val Val Thr Cys
1               5

<210> SEQ ID NO 127
<211> LENGTH: 11
<212> TYPE: PRT
<213> ORGANISM: Homo sapiens

<400> SEQUENCE: 127

Thr Leu Ile Ser Asp Ile Glu Ala Val Lys Ala
1               5                   10

<210> SEQ ID NO 128
<211> LENGTH: 10
<212> TYPE: PRT
<213> ORGANISM: Homo sapiens

<400> SEQUENCE: 128

Ala Leu Phe Pro Gly Asp Val Asp Arg Leu
1               5                   10

<210> SEQ ID NO 129
<211> LENGTH: 9
<212> TYPE: PRT
<213> ORGANISM: Homo sapiens

<400> SEQUENCE: 129

Val Leu Pro Asp Asp Leu Ser Gly Val
1               5

<210> SEQ ID NO 130
<211> LENGTH: 9
<212> TYPE: PRT
<213> ORGANISM: Homo sapiens

<400> SEQUENCE: 130

Gly Leu Val Asp Val Leu Tyr Thr Ala
1               5

<210> SEQ ID NO 131
<211> LENGTH: 10
<212> TYPE: PRT
<213> ORGANISM: Homo sapiens

<400> SEQUENCE: 131

Phe Val Asp Pro Asn Gly Lys Ile Ser Leu
1               5                   10

<210> SEQ ID NO 132
<211> LENGTH: 9
<212> TYPE: PRT
<213> ORGANISM: Homo sapiens

<400> SEQUENCE: 132

Phe Leu Asp Ala Ser Gly Ala Lys Leu
1               5

<210> SEQ ID NO 133
<211> LENGTH: 9
<212> TYPE: PRT
<213> ORGANISM: Homo sapiens

<400> SEQUENCE: 133

Ala Leu Asp Pro Ala Tyr Thr Thr Leu
1               5

<210> SEQ ID NO 134
<211> LENGTH: 9
<212> TYPE: PRT
<213> ORGANISM: Homo sapiens

<400> SEQUENCE: 134

Leu Leu Asp Glu Val Leu His Thr Met
1               5

<210> SEQ ID NO 135
<211> LENGTH: 9
<212> TYPE: PRT
<213> ORGANISM: Homo sapiens

<400> SEQUENCE: 135

Phe Leu Asp Asp Gln Glu Thr Arg Leu

```
1               5

<210> SEQ ID NO 136
<211> LENGTH: 11
<212> TYPE: PRT
<213> ORGANISM: Homo sapiens

<400> SEQUENCE: 136

Phe Ala Tyr Asp Gly Lys Asp Tyr Ile Ala Leu
1               5                   10

<210> SEQ ID NO 137
<211> LENGTH: 9
<212> TYPE: PRT
<213> ORGANISM: Homo sapiens

<400> SEQUENCE: 137

Ile Leu Pro Ser Asn Leu Leu Thr Val
1               5

<210> SEQ ID NO 138
<211> LENGTH: 9
<212> TYPE: PRT
<213> ORGANISM: Homo sapiens

<400> SEQUENCE: 138

Tyr Leu Asp Lys Thr Phe Tyr Asn Leu
1               5

<210> SEQ ID NO 139
<211> LENGTH: 9
<212> TYPE: PRT
<213> ORGANISM: Homo sapiens

<400> SEQUENCE: 139

Ala Val Asp Ala Thr Val Asn Gln Val
1               5

<210> SEQ ID NO 140
<211> LENGTH: 9
<212> TYPE: PRT
<213> ORGANISM: Homo sapiens

<400> SEQUENCE: 140

Arg Leu Glu Ala Tyr Leu Ala Arg Val
1               5

<210> SEQ ID NO 141
<211> LENGTH: 9
<212> TYPE: PRT
<213> ORGANISM: Homo sapiens

<400> SEQUENCE: 141

Tyr Val Ile Asp Pro Ile Lys Gly Leu
1               5

<210> SEQ ID NO 142
<211> LENGTH: 9
<212> TYPE: PRT
<213> ORGANISM: Homo sapiens

<400> SEQUENCE: 142

Phe Val Asp Gly Ser Ala Ile Gln Val
1               5
```

<210> SEQ ID NO 143
<211> LENGTH: 9
<212> TYPE: PRT
<213> ORGANISM: Homo sapiens

<400> SEQUENCE: 143

Ile Leu Asp Asp Ser Ala Leu Tyr Leu
1               5

<210> SEQ ID NO 144
<211> LENGTH: 9
<212> TYPE: PRT
<213> ORGANISM: Homo sapiens

<400> SEQUENCE: 144

Ser Val Asp Glu Val Glu Ile Ser Val
1               5

<210> SEQ ID NO 145
<211> LENGTH: 9
<212> TYPE: PRT
<213> ORGANISM: Homo sapiens

<400> SEQUENCE: 145

Thr Leu Pro Asn Ile Tyr Val Thr Leu
1               5

<210> SEQ ID NO 146
<211> LENGTH: 9
<212> TYPE: PRT
<213> ORGANISM: Homo sapiens

<400> SEQUENCE: 146

Gly Val Gly Pro Val Pro Ala Arg Ala
1               5

<210> SEQ ID NO 147
<211> LENGTH: 9
<212> TYPE: PRT
<213> ORGANISM: Homo sapiens

<400> SEQUENCE: 147

Ile Leu Asp Asp Gln Thr Asn Lys Leu
1               5

<210> SEQ ID NO 148
<211> LENGTH: 9
<212> TYPE: PRT
<213> ORGANISM: Homo sapiens

<400> SEQUENCE: 148

Thr Leu Lys Asp Ile Val Gln Thr Val
1               5

<210> SEQ ID NO 149
<211> LENGTH: 9
<212> TYPE: PRT
<213> ORGANISM: Homo sapiens

<400> SEQUENCE: 149

Tyr Leu Asp Thr Phe Ala Leu Lys Leu
1               5

<210> SEQ ID NO 150

-continued

```
<210> SEQ ID NO 150
<211> LENGTH: 10
<212> TYPE: PRT
<213> ORGANISM: Homo sapiens

<400> SEQUENCE: 150

Lys Leu Phe Pro Ser Pro Leu Gln Thr Leu
1               5                   10

<210> SEQ ID NO 151
<211> LENGTH: 11
<212> TYPE: PRT
<213> ORGANISM: Homo sapiens

<400> SEQUENCE: 151

Phe Leu Gly Glu Pro Ala Ser Tyr Leu Tyr Leu
1               5                   10

<210> SEQ ID NO 152
<211> LENGTH: 9
<212> TYPE: PRT
<213> ORGANISM: Homo sapiens

<400> SEQUENCE: 152

Ile Met Glu Asp Phe Thr Thr Phe Leu
1               5

<210> SEQ ID NO 153
<211> LENGTH: 9
<212> TYPE: PRT
<213> ORGANISM: Homo sapiens

<400> SEQUENCE: 153

Arg Leu Asp Glu Val Ser Arg Glu Leu
1               5

<210> SEQ ID NO 154
<211> LENGTH: 9
<212> TYPE: PRT
<213> ORGANISM: Homo sapiens

<400> SEQUENCE: 154

Thr Leu Gly Thr Ala Thr Phe Thr Val
1               5

<210> SEQ ID NO 155
<211> LENGTH: 9
<212> TYPE: PRT
<213> ORGANISM: Homo sapiens

<400> SEQUENCE: 155

Gly Leu Ala Gly Phe Phe Ala Ser Val
1               5

<210> SEQ ID NO 156
<211> LENGTH: 13
<212> TYPE: PRT
<213> ORGANISM: Homo sapiens

<400> SEQUENCE: 156

Ala Leu Met Asp Thr Asp Gly Ser Gly Lys Leu Asn Leu
1               5                   10

<210> SEQ ID NO 157
<211> LENGTH: 9
<212> TYPE: PRT
```

<213> ORGANISM: Homo sapiens

<400> SEQUENCE: 157

His Leu Phe Glu Thr Ile Ser Gln Ala
1               5

<210> SEQ ID NO 158
<211> LENGTH: 9
<212> TYPE: PRT
<213> ORGANISM: Homo sapiens

<400> SEQUENCE: 158

Lys Leu Ile Pro Ser Ile Ile Val Leu
1               5

<210> SEQ ID NO 159
<211> LENGTH: 9
<212> TYPE: PRT
<213> ORGANISM: Homo sapiens

<400> SEQUENCE: 159

Thr Ile Leu Ala Thr Val Pro Leu Val
1               5

<210> SEQ ID NO 160
<211> LENGTH: 9
<212> TYPE: PRT
<213> ORGANISM: Homo sapiens

<400> SEQUENCE: 160

Ala Leu Asp Asp Ile Ser Glu Ser Ile
1               5

<210> SEQ ID NO 161
<211> LENGTH: 9
<212> TYPE: PRT
<213> ORGANISM: Homo sapiens

<400> SEQUENCE: 161

Gly Leu Cys Asp Ser Ile Ile Thr Ile
1               5

<210> SEQ ID NO 162
<211> LENGTH: 9
<212> TYPE: PRT
<213> ORGANISM: Homo sapiens

<400> SEQUENCE: 162

Thr Leu Asp Gly Asn Pro Phe Leu Val
1               5

<210> SEQ ID NO 163
<211> LENGTH: 11
<212> TYPE: PRT
<213> ORGANISM: Homo sapiens

<400> SEQUENCE: 163

Arg Leu Met Ala Asn Pro Glu Ala Leu Lys Ile
1               5                   10

<210> SEQ ID NO 164
<211> LENGTH: 9
<212> TYPE: PRT
<213> ORGANISM: Homo sapiens

```
<400> SEQUENCE: 164

Ala Leu Phe Phe Gln Leu Val Asp Val
1               5

<210> SEQ ID NO 165
<211> LENGTH: 10
<212> TYPE: PRT
<213> ORGANISM: Homo sapiens

<400> SEQUENCE: 165

Ala Leu Ile Glu Val Leu Gln Pro Leu Ile
1               5                   10

<210> SEQ ID NO 166
<211> LENGTH: 9
<212> TYPE: PRT
<213> ORGANISM: Homo sapiens

<400> SEQUENCE: 166

Ser Ile Ile Pro Pro Leu Phe Thr Val
1               5

<210> SEQ ID NO 167
<211> LENGTH: 9
<212> TYPE: PRT
<213> ORGANISM: Homo sapiens

<400> SEQUENCE: 167

Lys Val Leu Gly Asp Val Ile Glu Val
1               5

<210> SEQ ID NO 168
<211> LENGTH: 9
<212> TYPE: PRT
<213> ORGANISM: Homo sapiens

<400> SEQUENCE: 168

Lys Leu Leu Ala Ala Thr Leu Leu Leu
1               5

<210> SEQ ID NO 169
<211> LENGTH: 9
<212> TYPE: PRT
<213> ORGANISM: Homo sapiens

<400> SEQUENCE: 169

Thr Leu Leu Glu Ser Ile Gln His Val
1               5

<210> SEQ ID NO 170
<211> LENGTH: 9
<212> TYPE: PRT
<213> ORGANISM: Homo sapiens

<400> SEQUENCE: 170

Lys Leu Lys Glu Ala Val Glu Ala Ile
1               5

<210> SEQ ID NO 171
<211> LENGTH: 9
<212> TYPE: PRT
<213> ORGANISM: Homo sapiens

<400> SEQUENCE: 171
```

Lys Val Ser Gly Val Ile Leu Ser Val
1               5

<210> SEQ ID NO 172
<211> LENGTH: 9
<212> TYPE: PRT
<213> ORGANISM: Homo sapiens

<400> SEQUENCE: 172

Phe Leu Pro Ala Gly Ile Val Ala Val
1               5

<210> SEQ ID NO 173
<211> LENGTH: 9
<212> TYPE: PRT
<213> ORGANISM: Homo sapiens

<400> SEQUENCE: 173

Ala Leu Asp Asp Ile Ile Tyr Arg Ala
1               5

<210> SEQ ID NO 174
<211> LENGTH: 9
<212> TYPE: PRT
<213> ORGANISM: Homo sapiens

<400> SEQUENCE: 174

Thr Leu Leu Glu Gly Leu Thr Glu Leu
1               5

<210> SEQ ID NO 175
<211> LENGTH: 9
<212> TYPE: PRT
<213> ORGANISM: Homo sapiens

<400> SEQUENCE: 175

Val Leu Asp Ser Val Asp Val Arg Leu
1               5

<210> SEQ ID NO 176
<211> LENGTH: 9
<212> TYPE: PRT
<213> ORGANISM: Homo sapiens

<400> SEQUENCE: 176

Thr Leu Tyr Glu Gln Glu Ile Glu Val
1               5

<210> SEQ ID NO 177
<211> LENGTH: 9
<212> TYPE: PRT
<213> ORGANISM: Homo sapiens

<400> SEQUENCE: 177

Ile Leu Trp Asp Thr Leu Leu Arg Leu
1               5

<210> SEQ ID NO 178
<211> LENGTH: 10
<212> TYPE: PRT
<213> ORGANISM: Homo sapiens

<400> SEQUENCE: 178

Phe Ala Tyr Asp Gly Lys Asp Tyr Ile Ala
1               5                   10

```
<210> SEQ ID NO 179
<211> LENGTH: 9
<212> TYPE: PRT
<213> ORGANISM: Homo sapiens

<400> SEQUENCE: 179

Ala Leu Asp Asp Thr Val Leu Gln Val
1               5

<210> SEQ ID NO 180
<211> LENGTH: 9
<212> TYPE: PRT
<213> ORGANISM: Homo sapiens

<400> SEQUENCE: 180

Lys Leu Ala Glu Ala Leu Tyr Ile Ala
1               5

<210> SEQ ID NO 181
<211> LENGTH: 10
<212> TYPE: PRT
<213> ORGANISM: Homo sapiens

<400> SEQUENCE: 181

Gly Leu Ile Asp Leu Glu Ala Asn Tyr Leu
1               5                   10

<210> SEQ ID NO 182
<211> LENGTH: 9
<212> TYPE: PRT
<213> ORGANISM: Homo sapiens

<400> SEQUENCE: 182

Ser Val Ala Leu Val Ile His Asn Val
1               5

<210> SEQ ID NO 183
<211> LENGTH: 9
<212> TYPE: PRT
<213> ORGANISM: Homo sapiens

<400> SEQUENCE: 183

Phe Leu Asp Ser Leu Ile Tyr Gly Ala
1               5

<210> SEQ ID NO 184
<211> LENGTH: 11
<212> TYPE: PRT
<213> ORGANISM: Homo sapiens

<400> SEQUENCE: 184

Val Leu Phe Ser Ser Pro Pro Val Ile Leu Leu
1               5                   10

<210> SEQ ID NO 185
<211> LENGTH: 9
<212> TYPE: PRT
<213> ORGANISM: Homo sapiens

<400> SEQUENCE: 185

Ile Leu Ala Asp Ala Thr Ala Lys Met
1               5
```

```
<210> SEQ ID NO 186
<211> LENGTH: 9
<212> TYPE: PRT
<213> ORGANISM: Homo sapiens

<400> SEQUENCE: 186

Phe Leu Asp His Glu Met Val Phe Leu
1               5

<210> SEQ ID NO 187
<211> LENGTH: 9
<212> TYPE: PRT
<213> ORGANISM: Homo sapiens

<400> SEQUENCE: 187

Ser Leu Pro Arg Pro Thr Pro Gln Ala
1               5

<210> SEQ ID NO 188
<211> LENGTH: 9
<212> TYPE: PRT
<213> ORGANISM: Homo sapiens

<400> SEQUENCE: 188

Val Val Val Asp Pro Ile Gln Ser Val
1               5

<210> SEQ ID NO 189
<211> LENGTH: 9
<212> TYPE: PRT
<213> ORGANISM: Homo sapiens

<400> SEQUENCE: 189

Lys Ala Leu Gln Phe Leu Glu Glu Val
1               5

<210> SEQ ID NO 190
<211> LENGTH: 9
<212> TYPE: PRT
<213> ORGANISM: Homo sapiens

<400> SEQUENCE: 190

Arg Leu Val Ser Leu Ile Thr Leu Leu
1               5

<210> SEQ ID NO 191
<211> LENGTH: 9
<212> TYPE: PRT
<213> ORGANISM: Homo sapiens

<400> SEQUENCE: 191

Tyr Leu Asp Lys Met Asn Asn Asn Ile
1               5

<210> SEQ ID NO 192
<211> LENGTH: 9
<212> TYPE: PRT
<213> ORGANISM: Homo sapiens

<400> SEQUENCE: 192

Lys Leu Phe Thr Gln Ile Phe Gly Val
1               5

<210> SEQ ID NO 193
<211> LENGTH: 9
```

```
<212> TYPE: PRT
<213> ORGANISM: Homo sapiens

<400> SEQUENCE: 193

Ala Leu Asp Glu Pro Thr Thr Asn Leu
1               5

<210> SEQ ID NO 194
<211> LENGTH: 9
<212> TYPE: PRT
<213> ORGANISM: Homo sapiens

<400> SEQUENCE: 194

Thr Leu Asp Asp Ile Met Ala Ala Val
1               5

<210> SEQ ID NO 195
<211> LENGTH: 9
<212> TYPE: PRT
<213> ORGANISM: Homo sapiens

<400> SEQUENCE: 195

Ile Ala Ala Gly Ile Phe Asn Asp Leu
1               5

<210> SEQ ID NO 196
<211> LENGTH: 9
<212> TYPE: PRT
<213> ORGANISM: Homo sapiens

<400> SEQUENCE: 196

Ala Leu Glu Pro Ile Asp Ile Thr Val
1               5

<210> SEQ ID NO 197
<211> LENGTH: 9
<212> TYPE: PRT
<213> ORGANISM: Homo sapiens

<400> SEQUENCE: 197

Ala Leu Asp Ser Gly Phe Asn Ser Val
1               5

<210> SEQ ID NO 198
<211> LENGTH: 9
<212> TYPE: PRT
<213> ORGANISM: Homo sapiens

<400> SEQUENCE: 198

Glu Val Val Asp Lys Ile Asn Gln Val
1               5

<210> SEQ ID NO 199
<211> LENGTH: 9
<212> TYPE: PRT
<213> ORGANISM: Homo sapiens

<400> SEQUENCE: 199

Ala Ile His Thr Ala Ile Leu Thr Leu
1               5

<210> SEQ ID NO 200
<211> LENGTH: 9
<212> TYPE: PRT
<213> ORGANISM: Homo sapiens
```

```
<400> SEQUENCE: 200

Leu Leu Glu Glu Ile Asn His Phe Leu
1               5

<210> SEQ ID NO 201
<211> LENGTH: 9
<212> TYPE: PRT
<213> ORGANISM: Homo sapiens

<400> SEQUENCE: 201

Ser Leu Ile Asp Arg Thr Ile Lys Met
1               5

<210> SEQ ID NO 202
<211> LENGTH: 9
<212> TYPE: PRT
<213> ORGANISM: Homo sapiens

<400> SEQUENCE: 202

Arg Val Ala Phe Lys Ile Asn Ser Val
1               5

<210> SEQ ID NO 203
<211> LENGTH: 9
<212> TYPE: PRT
<213> ORGANISM: Homo sapiens

<400> SEQUENCE: 203

Phe Leu Asn Glu Asp Ile Ser Lys Leu
1               5

<210> SEQ ID NO 204
<211> LENGTH: 9
<212> TYPE: PRT
<213> ORGANISM: Homo sapiens

<400> SEQUENCE: 204

Arg Met Asp Glu Glu Phe Thr Lys Ile
1               5

<210> SEQ ID NO 205
<211> LENGTH: 9
<212> TYPE: PRT
<213> ORGANISM: Homo sapiens

<400> SEQUENCE: 205

Ser Leu Lys Ser Lys Val Leu Ser Val
1               5

<210> SEQ ID NO 206
<211> LENGTH: 10
<212> TYPE: PRT
<213> ORGANISM: Homo sapiens

<400> SEQUENCE: 206

Leu Leu Tyr Glu Asp Ile Pro Asp Lys Val
1               5                   10

<210> SEQ ID NO 207
<211> LENGTH: 9
<212> TYPE: PRT
<213> ORGANISM: Homo sapiens

<400> SEQUENCE: 207
```

Val Gln Ile Gly Asp Ile Val Thr Val
1               5

<210> SEQ ID NO 208
<211> LENGTH: 9
<212> TYPE: PRT
<213> ORGANISM: Homo sapiens

<400> SEQUENCE: 208

Tyr Ser Asp Asp Ile Pro His Ala Leu
1               5

<210> SEQ ID NO 209
<211> LENGTH: 9
<212> TYPE: PRT
<213> ORGANISM: Homo sapiens

<400> SEQUENCE: 209

Ser Ile Leu Asp Gly Leu Ile His Leu
1               5

<210> SEQ ID NO 210
<211> LENGTH: 10
<212> TYPE: PRT
<213> ORGANISM: Homo sapiens

<400> SEQUENCE: 210

Leu Leu Pro Glu Leu Arg Asp Trp Gly Val
1               5                   10

<210> SEQ ID NO 211
<211> LENGTH: 9
<212> TYPE: PRT
<213> ORGANISM: Homo sapiens

<400> SEQUENCE: 211

Phe Leu Pro Phe Leu Thr Thr Glu Val
1               5

<210> SEQ ID NO 212
<211> LENGTH: 9
<212> TYPE: PRT
<213> ORGANISM: Homo sapiens

<400> SEQUENCE: 212

Leu Leu Lys Asp Ser Ile Val Gln Leu
1               5

<210> SEQ ID NO 213
<211> LENGTH: 9
<212> TYPE: PRT
<213> ORGANISM: Homo sapiens

<400> SEQUENCE: 213

Leu Leu Asp Pro Thr Asn Val Phe Ile
1               5

<210> SEQ ID NO 214
<211> LENGTH: 9
<212> TYPE: PRT
<213> ORGANISM: Homo sapiens

<400> SEQUENCE: 214

Val Leu Met Glu Met Ser Tyr Arg Leu

```
1               5

<210> SEQ ID NO 215
<211> LENGTH: 9
<212> TYPE: PRT
<213> ORGANISM: Homo sapiens

<400> SEQUENCE: 215

Glu Val Ile Ser Lys Leu Tyr Ala Val
1               5

<210> SEQ ID NO 216
<211> LENGTH: 9
<212> TYPE: PRT
<213> ORGANISM: Homo sapiens

<400> SEQUENCE: 216

Thr Leu Leu His Phe Leu Ala Glu Leu
1               5

<210> SEQ ID NO 217
<211> LENGTH: 9
<212> TYPE: PRT
<213> ORGANISM: Homo sapiens

<400> SEQUENCE: 217

Asn Met Met Ser Gly Ile Ser Ser Val
1               5

<210> SEQ ID NO 218
<211> LENGTH: 9
<212> TYPE: PRT
<213> ORGANISM: Homo sapiens

<400> SEQUENCE: 218

Ser Thr Leu His Leu Val Leu Arg Leu
1               5

<210> SEQ ID NO 219
<211> LENGTH: 9
<212> TYPE: PRT
<213> ORGANISM: Homo sapiens

<400> SEQUENCE: 219

Phe Leu Asp Ser Glu Val Ser Glu Leu
1               5

<210> SEQ ID NO 220
<211> LENGTH: 9
<212> TYPE: PRT
<213> ORGANISM: Homo sapiens

<400> SEQUENCE: 220

Ser Ala Ala Glu Pro Thr Pro Ala Val
1               5

<210> SEQ ID NO 221
<211> LENGTH: 10
<212> TYPE: PRT
<213> ORGANISM: Homo sapiens

<400> SEQUENCE: 221

Ser Leu Leu Pro Thr Glu Gln Pro Arg Leu
1               5                   10
```

<210> SEQ ID NO 222
<211> LENGTH: 9
<212> TYPE: PRT
<213> ORGANISM: Homo sapiens

<400> SEQUENCE: 222

Leu Leu Ser Glu Ile Glu Glu His Leu
1               5

<210> SEQ ID NO 223
<211> LENGTH: 9
<212> TYPE: PRT
<213> ORGANISM: Homo sapiens

<400> SEQUENCE: 223

Phe Leu Glu Thr Asn Val Pro Leu Leu
1               5

<210> SEQ ID NO 224
<211> LENGTH: 9
<212> TYPE: PRT
<213> ORGANISM: Homo sapiens

<400> SEQUENCE: 224

Ile Leu Asp Glu Pro Thr Asn His Leu
1               5

<210> SEQ ID NO 225
<211> LENGTH: 10
<212> TYPE: PRT
<213> ORGANISM: Homo sapiens

<400> SEQUENCE: 225

Val Leu Phe Gly Ala Val Ile Thr Gly Ala
1               5                   10

<210> SEQ ID NO 226
<211> LENGTH: 9
<212> TYPE: PRT
<213> ORGANISM: Homo sapiens

<400> SEQUENCE: 226

Val Leu Asn Glu Tyr Phe His Asn Val
1               5

<210> SEQ ID NO 227
<211> LENGTH: 11
<212> TYPE: PRT
<213> ORGANISM: Homo sapiens

<400> SEQUENCE: 227

Phe Leu Leu Glu Gln Glu Lys Thr Gln Ala Leu
1               5                   10

<210> SEQ ID NO 228
<211> LENGTH: 9
<212> TYPE: PRT
<213> ORGANISM: Homo sapiens

<400> SEQUENCE: 228

Phe Leu Asn Leu Phe Asn His Thr Leu
1               5

<210> SEQ ID NO 229

```
<211> LENGTH: 9
<212> TYPE: PRT
<213> ORGANISM: Homo sapiens

<400> SEQUENCE: 229

Leu Leu Glu Pro Phe Val His Gln Val
1               5

<210> SEQ ID NO 230
<211> LENGTH: 9
<212> TYPE: PRT
<213> ORGANISM: Homo sapiens

<400> SEQUENCE: 230

His Leu Asp Glu Ala Arg Thr Leu Leu
1               5

<210> SEQ ID NO 231
<211> LENGTH: 9
<212> TYPE: PRT
<213> ORGANISM: Homo sapiens

<400> SEQUENCE: 231

Lys Met Val Gly Asp Val Thr Gly Ala
1               5

<210> SEQ ID NO 232
<211> LENGTH: 9
<212> TYPE: PRT
<213> ORGANISM: Homo sapiens

<400> SEQUENCE: 232

Lys Ile Leu Pro Asp Leu Asn Thr Val
1               5

<210> SEQ ID NO 233
<211> LENGTH: 9
<212> TYPE: PRT
<213> ORGANISM: Homo sapiens

<400> SEQUENCE: 233

Gln Leu Tyr Asn Gln Ile Ile Lys Leu
1               5

<210> SEQ ID NO 234
<211> LENGTH: 9
<212> TYPE: PRT
<213> ORGANISM: Homo sapiens

<400> SEQUENCE: 234

Lys Val Pro Glu Ile Glu Val Thr Val
1               5

<210> SEQ ID NO 235
<211> LENGTH: 9
<212> TYPE: PRT
<213> ORGANISM: Homo sapiens

<400> SEQUENCE: 235

Ala Leu Ala Asp Leu Gln Glu Ala Val
1               5

<210> SEQ ID NO 236
<211> LENGTH: 9
<212> TYPE: PRT
```

```
<213> ORGANISM: Homo sapiens

<400> SEQUENCE: 236

Gly Leu Asp Ser Gly Phe His Ser Val
1               5

<210> SEQ ID NO 237
<211> LENGTH: 9
<212> TYPE: PRT
<213> ORGANISM: Homo sapiens

<400> SEQUENCE: 237

Val Leu Tyr Asn Glu Ser Leu Gln Leu
1               5

<210> SEQ ID NO 238
<211> LENGTH: 10
<212> TYPE: PRT
<213> ORGANISM: Homo sapiens

<400> SEQUENCE: 238

Lys Leu Leu Asp Lys Pro Glu Gln Phe Leu
1               5                   10

<210> SEQ ID NO 239
<211> LENGTH: 9
<212> TYPE: PRT
<213> ORGANISM: Homo sapiens

<400> SEQUENCE: 239

Phe Leu Asn Asp Ile Phe Glu Arg Ile
1               5

<210> SEQ ID NO 240
<211> LENGTH: 9
<212> TYPE: PRT
<213> ORGANISM: Homo sapiens

<400> SEQUENCE: 240

Gly Leu Ala Glu Phe Gln Glu Asn Val
1               5

<210> SEQ ID NO 241
<211> LENGTH: 10
<212> TYPE: PRT
<213> ORGANISM: Homo sapiens

<400> SEQUENCE: 241

Arg Leu Tyr Thr Lys Leu Leu Asn Glu Ala
1               5                   10

<210> SEQ ID NO 242
<211> LENGTH: 9
<212> TYPE: PRT
<213> ORGANISM: Homo sapiens

<400> SEQUENCE: 242

Ser Leu Glu Ser Lys Leu Thr Ser Val
1               5

<210> SEQ ID NO 243
<211> LENGTH: 9
<212> TYPE: PRT
<213> ORGANISM: Homo sapiens
```

<400> SEQUENCE: 243

Ala Leu Ala Gly Ile Val Thr Asn Val
1               5

<210> SEQ ID NO 244
<211> LENGTH: 9
<212> TYPE: PRT
<213> ORGANISM: Homo sapiens

<400> SEQUENCE: 244

Ile Leu Leu Glu Lys Ser Val Ser Val
1               5

<210> SEQ ID NO 245
<211> LENGTH: 11
<212> TYPE: PRT
<213> ORGANISM: Homo sapiens

<400> SEQUENCE: 245

Leu Leu Val Asp Asp Ser Phe Leu His Thr Val
1               5                   10

<210> SEQ ID NO 246
<211> LENGTH: 9
<212> TYPE: PRT
<213> ORGANISM: Homo sapiens

<400> SEQUENCE: 246

Thr Gln Asp Asp Tyr Val Leu Glu Val
1               5

<210> SEQ ID NO 247
<211> LENGTH: 10
<212> TYPE: PRT
<213> ORGANISM: Homo sapiens

<400> SEQUENCE: 247

Ala Leu Leu Asn Ala Ile Leu His Ser Ala
1               5                   10

<210> SEQ ID NO 248
<211> LENGTH: 11
<212> TYPE: PRT
<213> ORGANISM: Homo sapiens

<400> SEQUENCE: 248

Gly Leu Phe Ala Gly Leu Gly Gly Ala Gly Ala
1               5                   10

<210> SEQ ID NO 249
<211> LENGTH: 9
<212> TYPE: PRT
<213> ORGANISM: Homo sapiens

<400> SEQUENCE: 249

Lys Leu Gln Asp Gly Leu Leu His Ile
1               5

<210> SEQ ID NO 250
<211> LENGTH: 11
<212> TYPE: PRT
<213> ORGANISM: Homo sapiens

<400> SEQUENCE: 250

Arg Val Leu Pro Pro Ser Ala Leu Gln Ser Val
1               5                   10

<210> SEQ ID NO 251
<211> LENGTH: 9
<212> TYPE: PRT
<213> ORGANISM: Homo sapiens

<400> SEQUENCE: 251

Val Leu Asp Gly Lys Val Ala Val Val
1               5

<210> SEQ ID NO 252
<211> LENGTH: 10
<212> TYPE: PRT
<213> ORGANISM: Homo sapiens

<400> SEQUENCE: 252

Tyr Leu Leu Asp Met Pro Leu Trp Tyr Leu
1               5                   10

<210> SEQ ID NO 253
<211> LENGTH: 9
<212> TYPE: PRT
<213> ORGANISM: Homo sapiens

<400> SEQUENCE: 253

Lys Leu Asp Ile Lys Val Glu Thr Val
1               5

<210> SEQ ID NO 254
<211> LENGTH: 11
<212> TYPE: PRT
<213> ORGANISM: Homo sapiens

<400> SEQUENCE: 254

Phe Leu Met Lys Asn Ser Asp Leu Tyr Gly Ala
1               5                   10

<210> SEQ ID NO 255
<211> LENGTH: 9
<212> TYPE: PRT
<213> ORGANISM: Homo sapiens

<400> SEQUENCE: 255

Leu Leu Leu Gly Glu Arg Val Ala Leu
1               5

<210> SEQ ID NO 256
<211> LENGTH: 9
<212> TYPE: PRT
<213> ORGANISM: Homo sapiens

<400> SEQUENCE: 256

Val Leu Leu Asp Thr Ile Leu Gln Leu
1               5

<210> SEQ ID NO 257
<211> LENGTH: 10
<212> TYPE: PRT
<213> ORGANISM: Homo sapiens

<400> SEQUENCE: 257

Val Leu Leu Asn Glu Ile Leu Glu Gln Val
1               5                   10

<210> SEQ ID NO 258
<211> LENGTH: 9
<212> TYPE: PRT
<213> ORGANISM: Homo sapiens

<400> SEQUENCE: 258

Phe Leu Lys Asn Glu Leu Asp Asn Val
1               5

<210> SEQ ID NO 259
<211> LENGTH: 9
<212> TYPE: PRT
<213> ORGANISM: Homo sapiens

<400> SEQUENCE: 259

Gly Leu Asp Gly Ile Pro Phe Thr Val
1               5

<210> SEQ ID NO 260
<211> LENGTH: 9
<212> TYPE: PRT
<213> ORGANISM: Homo sapiens

<400> SEQUENCE: 260

Gln Leu Ile Asp Tyr Glu Arg Gln Leu
1               5

<210> SEQ ID NO 261
<211> LENGTH: 9
<212> TYPE: PRT
<213> ORGANISM: Homo sapiens

<400> SEQUENCE: 261

Gly Leu Ser Glu Val Leu Val Gln Ile
1               5

<210> SEQ ID NO 262
<211> LENGTH: 9
<212> TYPE: PRT
<213> ORGANISM: Homo sapiens

<400> SEQUENCE: 262

Lys Leu Ala Val Ala Leu Leu Ala Ala
1               5

<210> SEQ ID NO 263
<211> LENGTH: 9
<212> TYPE: PRT
<213> ORGANISM: Homo sapiens

<400> SEQUENCE: 263

Tyr Ala Leu Asp Leu Ser Thr Phe Leu
1               5

<210> SEQ ID NO 264
<211> LENGTH: 9
<212> TYPE: PRT
<213> ORGANISM: Homo sapiens

<400> SEQUENCE: 264

Lys Val Phe Asp Glu Val Ile Glu Val
1               5

-continued

```
<210> SEQ ID NO 265
<211> LENGTH: 9
<212> TYPE: PRT
<213> ORGANISM: Homo sapiens

<400> SEQUENCE: 265

Ile Leu Tyr Asp Leu Gln Gln Asn Leu
1               5

<210> SEQ ID NO 266
<211> LENGTH: 9
<212> TYPE: PRT
<213> ORGANISM: Homo sapiens

<400> SEQUENCE: 266

Tyr Leu Ala Pro Glu Asn Gly Tyr Leu
1               5

<210> SEQ ID NO 267
<211> LENGTH: 9
<212> TYPE: PRT
<213> ORGANISM: Homo sapiens

<400> SEQUENCE: 267

Leu Leu Thr Asp Asn Val Val Lys Leu
1               5

<210> SEQ ID NO 268
<211> LENGTH: 9
<212> TYPE: PRT
<213> ORGANISM: Homo sapiens

<400> SEQUENCE: 268

Ala Leu Ala Asp Leu Ser Val Ala Val
1               5

<210> SEQ ID NO 269
<211> LENGTH: 9
<212> TYPE: PRT
<213> ORGANISM: Homo sapiens

<400> SEQUENCE: 269

Ala Leu Asn Glu Ser Leu Val Glu Cys
1               5

<210> SEQ ID NO 270
<211> LENGTH: 11
<212> TYPE: PRT
<213> ORGANISM: Homo sapiens

<400> SEQUENCE: 270

Lys Ile Trp Glu Glu Leu Ser Val Leu Glu Val
1               5                   10

<210> SEQ ID NO 271
<211> LENGTH: 9
<212> TYPE: PRT
<213> ORGANISM: Homo sapiens

<400> SEQUENCE: 271

Ser Leu Val Gln Arg Val Glu Thr Ile
1               5

<210> SEQ ID NO 272
<211> LENGTH: 9
```

```
<212> TYPE: PRT
<213> ORGANISM: Homo sapiens

<400> SEQUENCE: 272

Tyr Leu Asp Pro Leu Trp His Gln Leu
 1               5

<210> SEQ ID NO 273
<211> LENGTH: 9
<212> TYPE: PRT
<213> ORGANISM: Homo sapiens

<400> SEQUENCE: 273

Ala Leu Ser Glu Leu Leu Gln Gln Val
 1               5

<210> SEQ ID NO 274
<211> LENGTH: 9
<212> TYPE: PRT
<213> ORGANISM: Homo sapiens

<400> SEQUENCE: 274

Arg Leu His Asp Glu Asn Ile Leu Leu
 1               5

<210> SEQ ID NO 275
<211> LENGTH: 9
<212> TYPE: PRT
<213> ORGANISM: Homo sapiens

<400> SEQUENCE: 275

Ser Leu Leu Asn Gln Pro Lys Ala Val
 1               5

<210> SEQ ID NO 276
<211> LENGTH: 9
<212> TYPE: PRT
<213> ORGANISM: Homo sapiens

<400> SEQUENCE: 276

Phe Leu Asp Ser Gln Ile Thr Thr Val
 1               5

<210> SEQ ID NO 277
<211> LENGTH: 9
<212> TYPE: PRT
<213> ORGANISM: Homo sapiens

<400> SEQUENCE: 277

Lys Thr Ala Ser Ile Asn Gln Asn Val
 1               5

<210> SEQ ID NO 278
<211> LENGTH: 11
<212> TYPE: PRT
<213> ORGANISM: Homo sapiens

<400> SEQUENCE: 278

Ser Leu Ile Thr Gly Gln Asp Leu Leu Ser Val
 1               5                  10

<210> SEQ ID NO 279
<211> LENGTH: 9
<212> TYPE: PRT
<213> ORGANISM: Homo sapiens
```

<400> SEQUENCE: 279

Val Val Ala Ala His Leu Ala Gly Ala
1               5

<210> SEQ ID NO 280
<211> LENGTH: 9
<212> TYPE: PRT
<213> ORGANISM: Homo sapiens

<400> SEQUENCE: 280

Leu Leu Trp Pro Ser Ser Val Pro Ala
1               5

<210> SEQ ID NO 281
<211> LENGTH: 9
<212> TYPE: PRT
<213> ORGANISM: Homo sapiens

<400> SEQUENCE: 281

Gly Leu Leu Glu Asn Ser Pro His Leu
1               5

<210> SEQ ID NO 282
<211> LENGTH: 9
<212> TYPE: PRT
<213> ORGANISM: Homo sapiens

<400> SEQUENCE: 282

Leu Leu Ile Pro Phe Thr Ile Phe Met
1               5

<210> SEQ ID NO 283
<211> LENGTH: 9
<212> TYPE: PRT
<213> ORGANISM: Homo sapiens

<400> SEQUENCE: 283

Tyr Thr Phe Ser Gly Asp Val Gln Leu
1               5

<210> SEQ ID NO 284
<211> LENGTH: 9
<212> TYPE: PRT
<213> ORGANISM: Homo sapiens

<400> SEQUENCE: 284

Thr Ile Gly Ile Pro Phe Pro Asn Val
1               5

<210> SEQ ID NO 285
<211> LENGTH: 9
<212> TYPE: PRT
<213> ORGANISM: Homo sapiens

<400> SEQUENCE: 285

Tyr Leu Met Asp Asp Phe Ser Ser Leu
1               5

<210> SEQ ID NO 286
<211> LENGTH: 9
<212> TYPE: PRT
<213> ORGANISM: Homo sapiens

<400> SEQUENCE: 286

```
Gly Leu Asn Gly Phe Asn Val Leu Leu
1               5

<210> SEQ ID NO 287
<211> LENGTH: 10
<212> TYPE: PRT
<213> ORGANISM: Homo sapiens

<400> SEQUENCE: 287

Lys Ile Ser Asp Phe Gly Leu Ala Thr Val
1               5                   10

<210> SEQ ID NO 288
<211> LENGTH: 11
<212> TYPE: PRT
<213> ORGANISM: Homo sapiens

<400> SEQUENCE: 288

Ala Leu Leu Glu Gln Thr Gly Asp Met Ser Leu
1               5                   10

<210> SEQ ID NO 289
<211> LENGTH: 9
<212> TYPE: PRT
<213> ORGANISM: Homo sapiens

<400> SEQUENCE: 289

Ile Leu Ala Gln Asp Val Ala Gln Leu
1               5

<210> SEQ ID NO 290
<211> LENGTH: 9
<212> TYPE: PRT
<213> ORGANISM: Homo sapiens

<400> SEQUENCE: 290

Asn Val Ala Glu Ile Val Ile His Ile
1               5

<210> SEQ ID NO 291
<211> LENGTH: 9
<212> TYPE: PRT
<213> ORGANISM: Homo sapiens

<400> SEQUENCE: 291

Leu Leu Asp Asp Ile Phe Ile Arg Leu
1               5

<210> SEQ ID NO 292
<211> LENGTH: 10
<212> TYPE: PRT
<213> ORGANISM: Homo sapiens

<400> SEQUENCE: 292

Ala Leu Gly Asp Lys Phe Leu Leu Arg Val
1               5                   10

<210> SEQ ID NO 293
<211> LENGTH: 9
<212> TYPE: PRT
<213> ORGANISM: Homo sapiens

<400> SEQUENCE: 293

Phe Leu Asp Gly Arg Pro Leu Thr Leu
```

```
<210> SEQ ID NO 294
<211> LENGTH: 9
<212> TYPE: PRT
<213> ORGANISM: Homo sapiens

<400> SEQUENCE: 294

Phe Leu Leu Ala Glu Asp Thr Lys Val
1               5

<210> SEQ ID NO 295
<211> LENGTH: 10
<212> TYPE: PRT
<213> ORGANISM: Homo sapiens

<400> SEQUENCE: 295

Phe Leu Pro Gln Pro Val Pro Leu Ser Val
1               5                   10

<210> SEQ ID NO 296
<211> LENGTH: 9
<212> TYPE: PRT
<213> ORGANISM: Homo sapiens

<400> SEQUENCE: 296

Phe Thr Ala Glu Phe Leu Glu Lys Val
1               5

<210> SEQ ID NO 297
<211> LENGTH: 9
<212> TYPE: PRT
<213> ORGANISM: Homo sapiens

<400> SEQUENCE: 297

Gly Val Asp Asp Ala Phe Tyr Thr Leu
1               5

<210> SEQ ID NO 298
<211> LENGTH: 9
<212> TYPE: PRT
<213> ORGANISM: Homo sapiens

<400> SEQUENCE: 298

Lys Leu Gln Glu Glu Ile Pro Val Leu
1               5

<210> SEQ ID NO 299
<211> LENGTH: 12
<212> TYPE: PRT
<213> ORGANISM: Homo sapiens

<400> SEQUENCE: 299

Asn Leu Leu Ile Asp Asp Lys Gly Thr Ile Lys Leu
1               5                   10

<210> SEQ ID NO 300
<211> LENGTH: 9
<212> TYPE: PRT
<213> ORGANISM: Homo sapiens

<400> SEQUENCE: 300

Gln Ile Asp Asp Val Thr Ile Lys Ile
1               5
```

<210> SEQ ID NO 301
<211> LENGTH: 11
<212> TYPE: PRT
<213> ORGANISM: Homo sapiens

<400> SEQUENCE: 301

Arg Val Ile Asp Asp Ser Leu Val Val Gly Val
1               5                   10

<210> SEQ ID NO 302
<211> LENGTH: 9
<212> TYPE: PRT
<213> ORGANISM: Homo sapiens

<400> SEQUENCE: 302

Thr Val Leu Gln Glu Leu Ile Asn Val
1               5

<210> SEQ ID NO 303
<211> LENGTH: 11
<212> TYPE: PRT
<213> ORGANISM: Homo sapiens

<400> SEQUENCE: 303

Lys Leu Gly Asp Phe Gly Leu Leu Val Glu Leu
1               5                   10

<210> SEQ ID NO 304
<211> LENGTH: 9
<212> TYPE: PRT
<213> ORGANISM: Homo sapiens

<400> SEQUENCE: 304

Val Leu Leu Ala Gln Ile Ile Gln Val
1               5

<210> SEQ ID NO 305
<211> LENGTH: 9
<212> TYPE: PRT
<213> ORGANISM: Homo sapiens

<400> SEQUENCE: 305

Thr Leu Leu Lys Thr Ile Ile Lys Val
1               5

<210> SEQ ID NO 306
<211> LENGTH: 10
<212> TYPE: PRT
<213> ORGANISM: Homo sapiens

<400> SEQUENCE: 306

Lys Met Leu Asp Glu Ile Leu Leu Gln Leu
1               5                   10

<210> SEQ ID NO 307
<211> LENGTH: 9
<212> TYPE: PRT
<213> ORGANISM: Homo sapiens

<400> SEQUENCE: 307

Ala Leu Ala Gly Gly Ile Thr Met Val
1               5

<210> SEQ ID NO 308

```
<211> LENGTH: 10
<212> TYPE: PRT
<213> ORGANISM: Homo sapiens

<400> SEQUENCE: 308

Lys Leu Leu Ser Asp Pro Asn Tyr Gly Val
1               5                   10

<210> SEQ ID NO 309
<211> LENGTH: 8
<212> TYPE: PRT
<213> ORGANISM: Homo sapiens

<400> SEQUENCE: 309

Met Gln Lys Glu Ile Thr Ala Leu
1               5

<210> SEQ ID NO 310
<211> LENGTH: 9
<212> TYPE: PRT
<213> ORGANISM: Homo sapiens

<400> SEQUENCE: 310

Ala Leu Ala Ser Val Ile Lys Glu Leu
1               5

<210> SEQ ID NO 311
<211> LENGTH: 9
<212> TYPE: PRT
<213> ORGANISM: Homo sapiens

<400> SEQUENCE: 311

Lys Leu Met Asp Tyr Ile Asp Glu Leu
1               5

<210> SEQ ID NO 312
<211> LENGTH: 9
<212> TYPE: PRT
<213> ORGANISM: Homo sapiens

<400> SEQUENCE: 312

Thr Ala Val Gly His Ala Leu Val Leu
1               5

<210> SEQ ID NO 313
<211> LENGTH: 10
<212> TYPE: PRT
<213> ORGANISM: Homo sapiens

<400> SEQUENCE: 313

Leu Leu Leu Asp Thr Val Thr Met Gln Val
1               5                   10

<210> SEQ ID NO 314
<211> LENGTH: 9
<212> TYPE: PRT
<213> ORGANISM: Homo sapiens

<400> SEQUENCE: 314

Ser Leu Phe Glu Trp Phe His Pro Leu
1               5

<210> SEQ ID NO 315
<211> LENGTH: 9
<212> TYPE: PRT
```

<213> ORGANISM: Homo sapiens

<400> SEQUENCE: 315

Lys Leu Ser Trp Asp Leu Ile Tyr Leu
1               5

<210> SEQ ID NO 316
<211> LENGTH: 9
<212> TYPE: PRT
<213> ORGANISM: Homo sapiens

<400> SEQUENCE: 316

Ala Leu Ala Glu Leu Leu His Gly Ala
1               5

<210> SEQ ID NO 317
<211> LENGTH: 9
<212> TYPE: PRT
<213> ORGANISM: Homo sapiens

<400> SEQUENCE: 317

Asn Leu Ala Glu Glu Leu Glu Gly Val
1               5

<210> SEQ ID NO 318
<211> LENGTH: 9
<212> TYPE: PRT
<213> ORGANISM: Homo sapiens

<400> SEQUENCE: 318

Ser Ile Ile Glu Tyr Leu Pro Thr Leu
1               5

<210> SEQ ID NO 319
<211> LENGTH: 9
<212> TYPE: PRT
<213> ORGANISM: Homo sapiens

<400> SEQUENCE: 319

Ala Leu Ser Ser Ser Gln Ala Glu Val
1               5

<210> SEQ ID NO 320
<211> LENGTH: 9
<212> TYPE: PRT
<213> ORGANISM: Homo sapiens

<400> SEQUENCE: 320

Lys Ile Ile Gly Ile Met Glu Glu Val
1               5

<210> SEQ ID NO 321
<211> LENGTH: 9
<212> TYPE: PRT
<213> ORGANISM: Homo sapiens

<400> SEQUENCE: 321

Tyr Leu Pro Thr Phe Phe Leu Thr Val
1               5

<210> SEQ ID NO 322
<211> LENGTH: 9
<212> TYPE: PRT
<213> ORGANISM: Homo sapiens

<400> SEQUENCE: 322

Ser Leu His Phe Leu Ile Leu Tyr Val
1               5

<210> SEQ ID NO 323
<211> LENGTH: 9
<212> TYPE: PRT
<213> ORGANISM: Homo sapiens

<400> SEQUENCE: 323

Val Val Asp Lys Thr Leu Leu Leu Val
1               5

<210> SEQ ID NO 324
<211> LENGTH: 9
<212> TYPE: PRT
<213> ORGANISM: Homo sapiens

<400> SEQUENCE: 324

Ser Leu Ala Asn Asn Val Thr Ser Val
1               5

<210> SEQ ID NO 325
<211> LENGTH: 11
<212> TYPE: PRT
<213> ORGANISM: Homo sapiens

<400> SEQUENCE: 325

Val Leu Val Asp Asp Gly Ile Lys Val Val
1               5                   10

<210> SEQ ID NO 326
<211> LENGTH: 9
<212> TYPE: PRT
<213> ORGANISM: Homo sapiens

<400> SEQUENCE: 326

Ala Leu Ser Gly Thr Leu Ser Gly Val
1               5

<210> SEQ ID NO 327
<211> LENGTH: 11
<212> TYPE: PRT
<213> ORGANISM: Homo sapiens

<400> SEQUENCE: 327

Ala Leu Ala Asp Lys Glu Leu Leu Pro Ser Val
1               5                   10

<210> SEQ ID NO 328
<211> LENGTH: 9
<212> TYPE: PRT
<213> ORGANISM: Homo sapiens

<400> SEQUENCE: 328

Ser Leu Ser Gln Glu Leu Val Gly Val
1               5

<210> SEQ ID NO 329
<211> LENGTH: 9
<212> TYPE: PRT
<213> ORGANISM: Homo sapiens

<400> SEQUENCE: 329

Val Leu Ala Pro Arg Val Leu Arg Ala
1               5

<210> SEQ ID NO 330
<211> LENGTH: 9
<212> TYPE: PRT
<213> ORGANISM: Homo sapiens

<400> SEQUENCE: 330

Lys Met Phe Phe Leu Ile Asp Lys Val
1               5

<210> SEQ ID NO 331
<211> LENGTH: 9
<212> TYPE: PRT
<213> ORGANISM: Homo sapiens

<400> SEQUENCE: 331

Ala Leu Ser Gln Val Thr Leu Leu Leu
1               5

<210> SEQ ID NO 332
<211> LENGTH: 9
<212> TYPE: PRT
<213> ORGANISM: Homo sapiens

<400> SEQUENCE: 332

Ala Val Val Glu Phe Leu Thr Ser Val
1               5

<210> SEQ ID NO 333
<211> LENGTH: 9
<212> TYPE: PRT
<213> ORGANISM: Homo sapiens

<400> SEQUENCE: 333

Arg Ile Pro Ala Tyr Phe Val Thr Val
1               5

<210> SEQ ID NO 334
<211> LENGTH: 11
<212> TYPE: PRT
<213> ORGANISM: Homo sapiens

<400> SEQUENCE: 334

Val Leu Leu Asp Lys Ile Lys Asn Leu Gln Val
1               5                   10

<210> SEQ ID NO 335
<211> LENGTH: 9
<212> TYPE: PRT
<213> ORGANISM: Homo sapiens

<400> SEQUENCE: 335

Lys Leu Ala Ser Met Leu Glu Thr Leu
1               5

<210> SEQ ID NO 336
<211> LENGTH: 9
<212> TYPE: PRT
<213> ORGANISM: Homo sapiens

<400> SEQUENCE: 336

Tyr Val Asp Pro Val Ile Thr Ser Ile
1               5

```
<210> SEQ ID NO 337
<211> LENGTH: 9
<212> TYPE: PRT
<213> ORGANISM: Homo sapiens

<400> SEQUENCE: 337

Phe Leu Val Asp Gly Ser Ser Ala Leu
1               5

<210> SEQ ID NO 338
<211> LENGTH: 9
<212> TYPE: PRT
<213> ORGANISM: Homo sapiens

<400> SEQUENCE: 338

Ser Leu Asn Lys Trp Ile Phe Thr Val
1               5

<210> SEQ ID NO 339
<211> LENGTH: 10
<212> TYPE: PRT
<213> ORGANISM: Homo sapiens

<400> SEQUENCE: 339

Glu Leu Ala Gly Ile Gly Ile Leu Thr Val
1               5                   10

<210> SEQ ID NO 340
<211> LENGTH: 9
<212> TYPE: PRT
<213> ORGANISM: Homo sapiens

<400> SEQUENCE: 340

Tyr Leu Leu Pro Ala Ile Val His Ile
1               5
```